(12) United States Patent
Kadoma et al.

(10) Patent No.: US 12,295,260 B2
(45) Date of Patent: May 6, 2025

(54) ORGANIC COMPOUND, LIGHT-EMITTING DEVICE, LIGHT-EMITTING APPARATUS, ELECTRONIC DEVICE, AND LIGHTING DEVICE

(71) Applicant: Semiconductor Energy Laboratory Co., Ltd., Kanagawa-ken (JP)

(72) Inventors: Hiroshi Kadoma, Kanagawa (JP); Satoshi Seo, Kanagawa (JP); Takumu Okuyama, Kanagawa (JP); Naoaki Hashimoto, Kanagawa (JP); Yusuke Takita, Kanagawa (JP); Tsunenori Suzuki, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 893 days.

(21) Appl. No.: 17/439,527

(22) PCT Filed: Mar. 11, 2020

(86) PCT No.: PCT/IB2020/052075
§ 371 (c)(1),
(2) Date: Sep. 15, 2021

(87) PCT Pub. No.: WO2020/194097
PCT Pub. Date: Oct. 1, 2020

(65) Prior Publication Data
US 2022/0158100 A1    May 19, 2022

(30) Foreign Application Priority Data

Mar. 22, 2019 (JP) .................................. 2019-055331

(51) Int. Cl.
*H01L 51/00* (2006.01)
*C07D 401/10* (2006.01)
(Continued)

(52) U.S. Cl.
CPC ......... *H10K 85/654* (2023.02); *C07D 401/10* (2013.01); *C07D 403/10* (2013.01); *H10K 85/6572* (2023.02); *H10K 50/16* (2023.02)

(58) Field of Classification Search
None
See application file for complete search history.

(56) References Cited

U.S. PATENT DOCUMENTS 5,077,142 A    12/1991 Sakon et al.
7,227,313 B2    6/2007 Huiberts et al.
(Continued)

FOREIGN PATENT DOCUMENTS

CN    102791659 A    11/2012
EP    2 084 138 A    8/2009
(Continued)

OTHER PUBLICATIONS

International Search Report (Application No. PCT/IB2020/052075) Dated Jun. 16, 2020.
(Continued)

*Primary Examiner* — Tae H Yoon
(74) *Attorney, Agent, or Firm* — Husch Blackwell LLP

(57) ABSTRACT

A quinoxaline derivative that is a novel organic compound is provided. A quinoxaline derivative represented by General Formula (G1) has a structure in which a quinoxaline skeleton is bonded to the 9-position of an anthracene skeleton, the 10-position of the anthracene skeleton is bonded to a heteroaromatic ring, and the 3-position of the heteroaromatic ring is nitrogen.

(Continued)

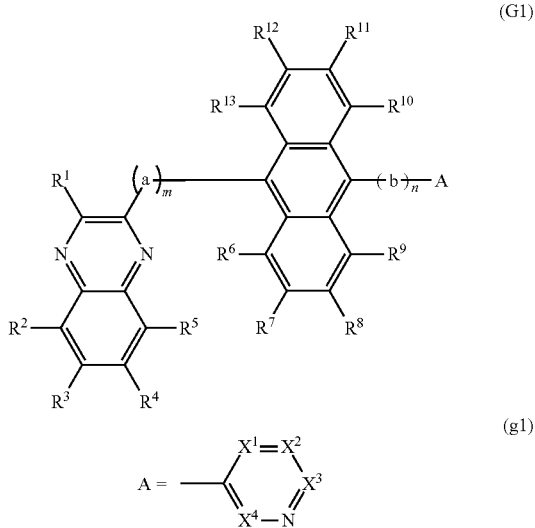

In General Formula (G1) shown above, a and b each independently represent a substituted or unsubstituted arylene group having 6 to 13 carbon atoms in a ring. In addition, m and n are each independently 0, 1, or 2.

24 Claims, 35 Drawing Sheets

(51) Int. Cl.
  *C07D 403/10* (2006.01)
  *H10K 85/60* (2023.01)
  *H10K 50/16* (2023.01)

(56) References Cited

U.S. PATENT DOCUMENTS

| | | |
|---|---|---|
| 7,612,204 B2 | 11/2009 | Egawa et al. |
| 7,799,894 B2 | 9/2010 | Morita et al. |
| 2005/0118454 A1 | 6/2005 | Nakaya et al. |
| 2005/0186446 A1 | 8/2005 | Shitagaki et al. |
| 2006/0051613 A1 | 3/2006 | Tomita et al. |
| 2006/0194076 A1 | 8/2006 | Nariyuki |
| 2008/0036369 A1 | 2/2008 | Tokuda et al. |
| 2008/0091012 A1 | 4/2008 | Egawa et al. |
| 2009/0140641 A1 | 6/2009 | Nomura et al. |
| 2009/0140642 A1 | 6/2009 | Kadoma et al. |
| 2009/0184633 A1 | 7/2009 | Kadoma et al. |
| 2009/0203704 A1 | 8/2009 | Kadoma et al. |
| 2010/0120778 A1 | 5/2010 | Hu et al. |
| 2012/0217449 A1 | 8/2012 | Spreitzer et al. |
| 2013/0032764 A1 | 2/2013 | Buesing et al. |

FOREIGN PATENT DOCUMENTS

| | | | |
|---|---|---|---|
| JP | 07-142169 A | | 6/1995 |
| JP | 2003-040873 A | | 2/2003 |
| JP | 2004-2297 A | * | 1/2004 |
| JP | 2004-200162 A | | 7/2004 |
| JP | 2006-016384 A | | 1/2006 |
| JP | 2008-094776 A | | 4/2008 |
| JP | 2008-110968 A | | 5/2008 |
| JP | 2010-182699 A | | 8/2010 |
| JP | 4979333 B2 | | 7/2012 |
| JP | 2013-510104 | | 3/2013 |
| JP | 2013-523788 | | 6/2013 |
| JP | 2015-003903 A | | 1/2015 |
| JP | 5837125 B2 | | 12/2015 |
| JP | 2016-106094 A | | 6/2016 |
| KR | 2012-0115249 A | | 10/2012 |
| KR | 2018-0059955 A | | 6/2018 |
| TW | 201134917 | | 10/2011 |
| WO | WO 2008/047589 A1 | | 4/2008 |
| WO | WO 2011/054442 A2 | | 5/2011 |
| WO | WO 2011/120626 A1 | | 10/2011 |

OTHER PUBLICATIONS

Written Opinion (Application No. PCT/IB2020/052075) Dated Jun. 16, 2020.

Thomas, K. et al., "Quinoxalines Incorporating Triarylamines: Potential Electroluminescent Materials With Tunable Emission Characteristics," Chemistry of Materials, 2002, vol. 14, No. 6, pp. 2796-2802.

Xiao, L. et al., Highly Efficient Electron-transporting Phenanthroline Derivatives for Electroluminescent Devices, Chemistry Letters, Jun. 1, 2007, vol. 36, No. 6, pp. 802-803, The Chemical Society of Japan.

Thomas, K. et al., "Chromophore-Labeled Quinoxaline Derivatives as Efficient Electroluminescent Materials," Chemistry of Materials, 2005, vol. 17, No. 7, pp. 1860-1866.

Krueger, H. et al., "Some New Electron-Affine Polymers for Organic Photovoltaics," Proceedings of SPIE, 2004, vol. 5215, pp. 141-152.

Taiwanese Office Action (Application No. 109108925) Dated Oct. 31, 2023.

* cited by examiner

4000

4200

ORGANIC COMPOUND, LIGHT-EMITTING DEVICE, LIGHT-EMITTING APPARATUS, ELECTRONIC DEVICE, AND LIGHTING DEVICE

TECHNICAL FIELD

Embodiments of the present invention relate to an organic compound, a light-emitting element, a light-emitting device, a display module, a lighting module, a display device, a light-emitting apparatus, an electronic device, and a lighting device. Note that one embodiment of the present invention is not limited to the above technical field. The technical field of one embodiment of the invention disclosed in this specification and the like relates to an object, a method, or a manufacturing method. One embodiment of the present invention relates to a process, a machine, manufacture, or a composition of matter. Specifically, examples of the technical field of one embodiment of the present invention disclosed in this specification include a semiconductor device, a display device, a liquid crystal display device, a light-emitting apparatus, a lighting device, a power storage device, a memory device, an imaging device, a driving method thereof, and a manufacturing method thereof.

BACKGROUND ART

A light-emitting device including an EL layer between a pair of electrodes (also referred to as an organic EL device or a light-emitting element) has characteristics such as thinness, light weight, high-speed response to input signals, and low power consumption; thus, a display including such a light-emitting device has attracted attention as a next-generation flat panel display.

In a light-emitting device, voltage application between a pair of electrodes causes, in an EL layer, recombination of electrons and holes injected from the electrodes, which brings a light-emitting substance (organic compound) contained in the EL layer into an excited state. Light is emitted when the light-emitting substance returns to the ground state from the excited state. The excited state can be a singlet excited state (S*) and a triplet excited state (T*). Light emission from a singlet excited state is referred to as fluorescence, and light emission from a triplet excited state is referred to as phosphorescence. The statistical generation ratio thereof in the light-emitting device is considered to be S*: T*=1:3. Since the spectrum of light emitted from a light-emitting substance depends on the light-emitting substance, the use of different types of organic compounds as light-emitting substances makes it possible to obtain light-emitting devices which exhibit various colors.

In order to improve element characteristics of such a light-emitting device, improvement of an element structure, development of a material, and the like have been actively carried out (see Patent Document 1, for example).

REFERENCE

Patent Document

[Patent Document 1] Japanese Published Patent Application No. 2010-182699

DISCLOSURE OF INVENTION

Thus, in one embodiment of the present invention, a novel organic compound is provided. In another embodiment of the present invention, a quinoxaline derivative that is a novel organic compound is provided. An object of another embodiment of the present invention is to provide a novel light-emitting device. An object of another embodiment of the present invention is to provide a light-emitting device with high emission efficiency. An object of another embodiment of the present invention is to provide a light-emitting device having a long lifetime. An object of another embodiment of the present invention is to provide a light-emitting device having low driving voltage.

An object of another embodiment of the present invention is to provide a light-emitting apparatus, an electronic device, and a display device each having high reliability. An object of another embodiment of the present invention is to provide a light-emitting apparatus, an electronic device, and a display device each with low power consumption.

It is only necessary that at least one of the above-described objects be achieved in the present invention.

One embodiment of the present invention is a quinoxaline derivative which is an organic compound represented by General Formula (G1) shown below. The quinoxaline derivative represented by General Formula (G1) shown below has a structure in which the 2-position or 3-position of a quinoxaline skeleton is bonded to the 9-position of an anthracene skeleton, and a heteroaromatic ring bonded to the 10-position of the anthracene skeleton has nitrogen (N) at the 3-position from the position bonded to the anthracene skeleton. In General Formula (G1) shown below, the quinoxaline skeleton may be bonded to the anthracene skeleton through an arylene group, and the anthracene skeleton may be bonded to the heteroaromatic ring through an arylene group.

[Chemical Formula 1]

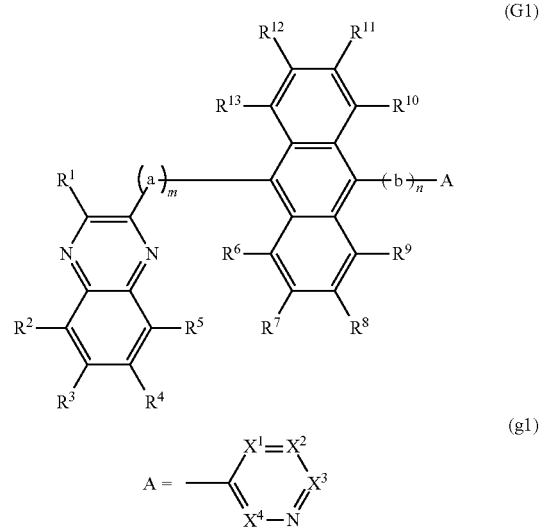

In General Formula (G1) shown above, a and b each independently represent a substituted or unsubstituted arylene group having 6 to 13 carbon atoms in a ring. In addition, m and n are each independently 0, 1, or 2. Note that two arylene groups a when m is 2 or two arylene groups b when n is 2 may be the same or different. Furthermore, $R^1$ to $R^{13}$ each independently represent hydrogen, an alkyl group having 1 to 6 carbon atoms, a substituted or unsubstituted cyclic alkyl group having 3 to 7 carbon atoms in a ring, or a substituted or unsubstituted aryl group having 6 to 13 carbon atoms in a ring. Moreover, A is represented by General Formula (g1). Furthermore, $X^1$ to $X^4$ each independently represent N or $CR^{14}$. Note that $R^{14}$ represents hydrogen, an alkyl group having 1 to 6 carbon atoms, a substituted or unsubstituted cyclic alkyl group having 3 to 7 carbon atoms in a ring, or a substituted or unsubstituted aryl group having 6 to 13 carbon atoms in a ring.

Another embodiment of the present invention is a quinoxaline derivative which is an organic compound represented by General Formula (G2) shown below.

[Chemical Formula 2]

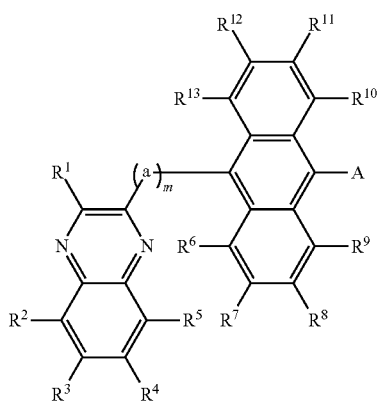
(G2)

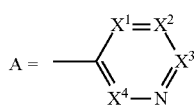
(g1)

In General Formula (G2) shown above, a represents a substituted or unsubstituted arylene group having 6 to 13 carbon atoms in a ring. In addition, m is 0, 1, or 2. Note that two arylene groups a when m is 2 may be the same or different. Furthermore, $R^1$ to $R^{13}$ each independently represent hydrogen, an alkyl group having 1 to 6 carbon atoms, a substituted or unsubstituted cyclic alkyl group having 3 to 7 carbon atoms in a ring, or a substituted or unsubstituted aryl group having 6 to 13 carbon atoms in a ring. Moreover, A is represented by General Formula (g1). Furthermore, $X^1$ to $X^4$ each independently represent N or $CR^{14}$. Note that $R^{14}$ represents hydrogen, an alkyl group having 1 to 6 carbon atoms, a substituted or unsubstituted cyclic alkyl group having 3 to 7 carbon atoms in a ring, or a substituted or unsubstituted aryl group having 6 to 13 carbon atoms in a ring.

Another embodiment of the present invention is a quinoxaline derivative which is an organic compound represented by General Formula (G3) shown below.

[Chemical Formula 3]

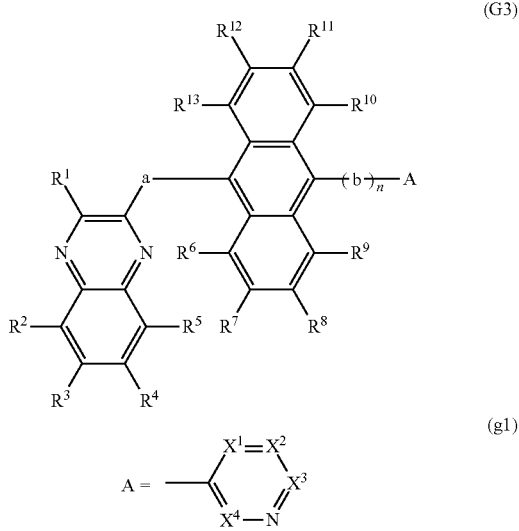
(G3)

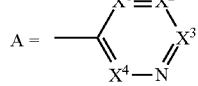
(g1)

In General Formula (G3) shown above, a and b each independently represent a substituted or unsubstituted arylene group having 6 to 13 carbon atoms in a ring. In addition, n is 0, 1, or 2. Note that two arylene groups b when n is 2 may be the same or different. Furthermore, $R^1$ to $R^{13}$ each independently represent hydrogen, an alkyl group having 1 to 6 carbon atoms, a substituted or unsubstituted cyclic alkyl group having 3 to 7 carbon atoms in a ring, or a substituted or unsubstituted aryl group having 6 to 13 carbon atoms in a ring. Moreover, A is represented by General Formula (g1). Furthermore, $X^1$ to $X^4$ each independently represent N or $CR^{14}$. Note that $R^{14}$ represents hydrogen, an alkyl group having 1 to 6 carbon atoms, a substituted or unsubstituted cyclic alkyl group having 3 to 7 carbon atoms in a ring, or a substituted or unsubstituted aryl group having 6 to 13 carbon atoms in a ring.

Another embodiment of the present invention is a quinoxaline derivative which is an organic compound represented by General Formula (G4) shown below.

[Chemical Formula 4]

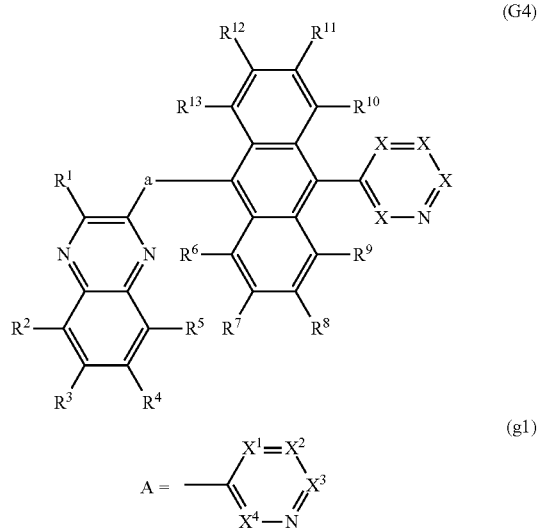
(G4)

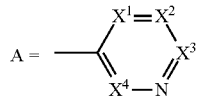
(g1)

In General Formula (G4) shown above, a represents a substituted or unsubstituted arylene group having 6 to 13 carbon atoms in a ring. Furthermore, $R^1$ to $R^{13}$ each independently represent hydrogen, an alkyl group having 1 to 6 carbon atoms, a substituted or unsubstituted cyclic alkyl group having 3 to 7 carbon atoms in a ring, or a substituted or unsubstituted aryl group having 6 to 13 carbon atoms in a ring. Moreover, A is represented by General Formula (g1). Furthermore, $X^1$ to $X^4$ each independently represent N or $CR^{14}$. Note that $R^{14}$ represents hydrogen, an alkyl group having 1 to 6 carbon atoms, a substituted or unsubstituted cyclic alkyl group having 3 to 7 carbon atoms in a ring, or a substituted or unsubstituted aryl group having 6 to 13 carbon atoms in a ring.

Another embodiment of the present invention is an organic compound in which a in General Formula (G4) shown above represents a substituted or unsubstituted phenylene group.

Another embodiment of the present invention is an organic compound in which General Formula (g1) shown above is represented by any one of General Formulae (g1-1) to (g1-3).

[Chemical Formulae 5]

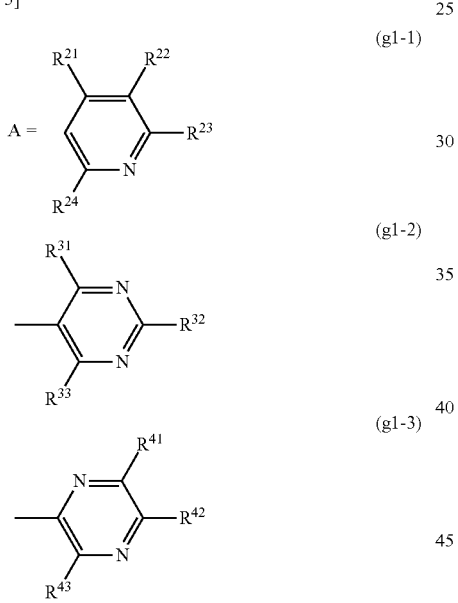

In General Formulae (g1-1) to (g1-3) shown above, $R^{21}$ to $R^{24}$, $R^{31}$ to $R^{33}$, and $R^{41}$ to $R^{43}$ each represent hydrogen, an alkyl group having 1 to 6 carbon atoms, a substituted or unsubstituted cyclic alkyl group having 3 to 7 carbon atoms in a ring, or a substituted or unsubstituted aryl group having 6 to 13 carbon atoms in a ring.

Another embodiment of the present invention is an organic compound in which General Formula (g1) shown above is represented by any one of General Formulae (g1-4) to (g1-6) shown below.

[Chemical Formulae 6]

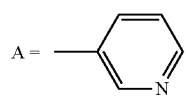

(g1-4)

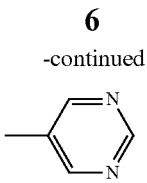

(g1-5)

(g1-6)

Another embodiment of the present invention is an organic compound represented by Structural Formula (100), Structural Formula (101), Structural Formula (102), Structural Formula (135), Structural Formula (147), or Structural Formula (175).

[Chemical Formulae 7]

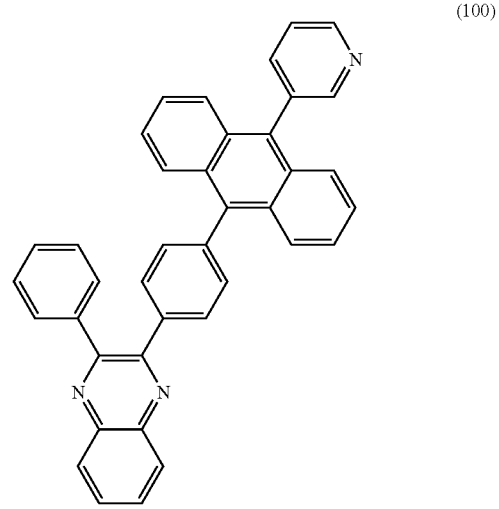

(100)

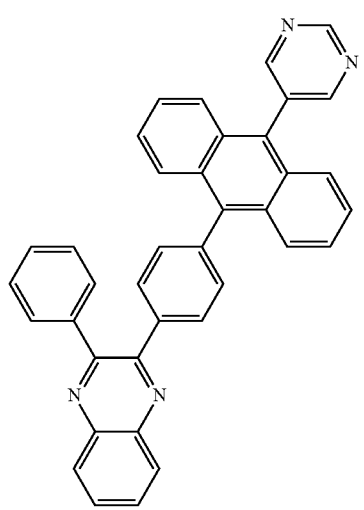

(101)

(102)
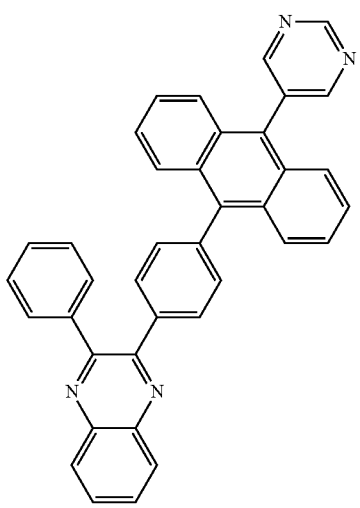

(135)
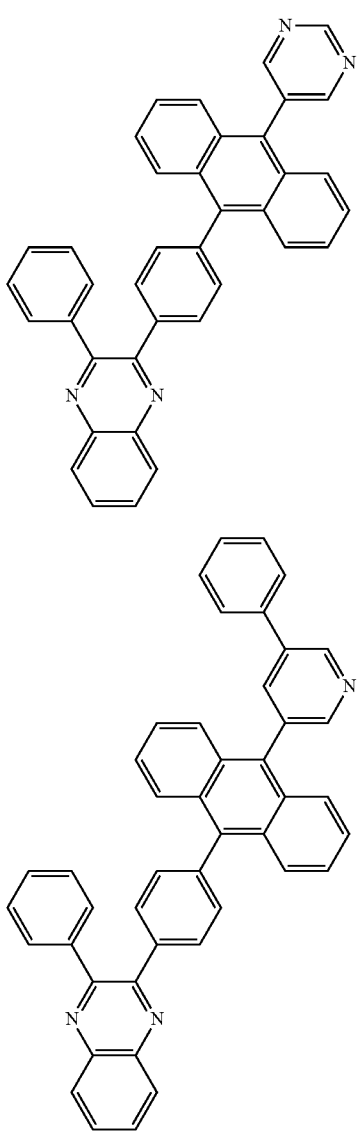

(147)

(175)
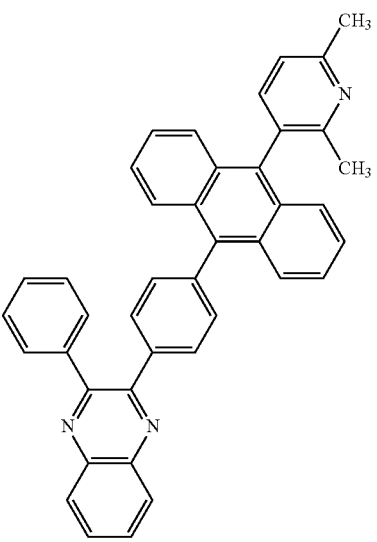

Another embodiment of the present invention is a light-emitting device using the above-described organic compound of one embodiment of the present invention. The present invention also includes a light-emitting device containing a guest material as well as the above-described organic compound. The present invention also includes a light-emitting device containing a phosphorescent material as well as the above-described organic compound. In addition to the above light-emitting devices, a light-emitting apparatus including a transistor, a substrate, and the like is also included in the scope of the invention. Furthermore, in addition to the light-emitting apparatus, an electronic device and a lighting device that include a microphone, a camera, an operation button, an external connection portion, a housing, a cover, a support, a speaker, or the like are also included in the scope of the invention.

The light-emitting apparatus in this specification includes, in its category, an image display device and a light source (e.g., a lighting device) each of which includes a light-emitting device. In addition, the light-emitting apparatus includes the following in its category: a module in which a connector such as a flexible printed circuit (FPC) or a tape carrier package (TCP) is attached to a light-emitting apparatus; a module in which a printed wiring board is provided at the end of a TCP; and a module in which an integrated circuit (IC) is directly mounted on a light-emitting device by a chip on glass (COG) method.

One embodiment of the present invention can provide a novel organic compound. Another embodiment of the present invention can provide a quinoxaline derivative that is a novel organic compound. Another embodiment of the present invention can provide a novel light-emitting device. Another embodiment of the present invention can provide a light-emitting device having a long lifetime. Another embodiment of the present invention can provide a light-emitting device with high emission efficiency.

Another embodiment of the present invention can provide a light-emitting apparatus, an electronic device, and a display device each having high reliability. Another embodiment of the present invention can provide a light-emitting apparatus, an electronic device, and a display device each with low power consumption.

Note that the description of these effects does not preclude the existence of other effects. One embodiment of the present invention does not necessarily achieve all the effects listed above. Other effects will be apparent from and can be derived from the description of the specification, the drawings, the claims, and the like.

BEST MODE FOR CARRYING OUT THE INVENTION

Figure 1A:
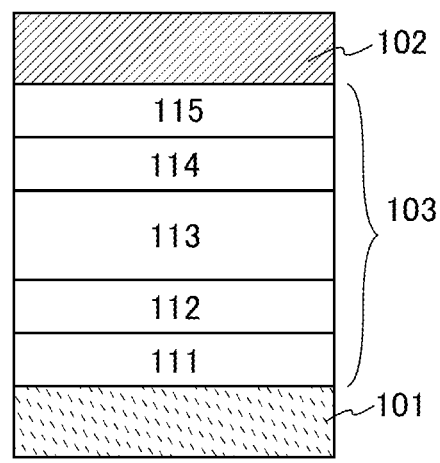
FIGS. 1A and 1B illustrate structures of light-emitting devices.

Embodiments of the present invention will be described in detail below with reference to the drawings. Note that the present invention is not limited to the following description, and it will be readily appreciated by those skilled in the art that modes and details of the present invention can be modified in various ways without departing from the spirit and scope of the present invention. Therefore, the present invention should not be construed as being limited to the description in the following embodiments.

Embodiment 1

In this embodiment, organic compounds of embodiments of the present invention will be described.

An organic compound of one embodiment of the present invention is a quinoxaline derivative represented by General Formula (G1) shown below. As represented by General Formula (G1) shown below, the organic compound of one embodiment of the present invention has a structure in which the 2-position or 3-position of a quinoxaline skeleton is bonded to the 9-position of an anthracene skeleton, and a heteroaromatic ring bonded to the 10-position of the anthracene skeleton has nitrogen (N) at the 3-position from the position bonded to the anthracene skeleton. The 2-position or 3-position of the quinoxaline skeleton may be bonded to the 9-position of the anthracene skeleton through an arylene group. In addition, the 10-position of the anthracene skeleton may be bonded to the heteroaromatic ring through an arylene group.

[Chemical Formula 8]

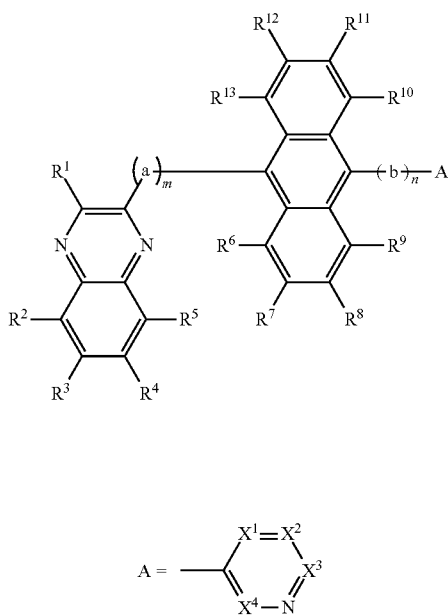

(G1)

(g1)

In General Formula (G1) shown above, a and b each independently represent a substituted or unsubstituted arylene group having 6 to 13 carbon atoms in a ring. In addition, m and n are each independently 0, 1, or 2. Note that two arylene groups a when m is 2 or two arylene groups b when n is 2 may be the same or different. Furthermore, $R^1$ to $R^{13}$ each independently represent hydrogen, an alkyl group having 1 to 6 carbon atoms, a substituted or unsubstituted cyclic alkyl group having 3 to 7 carbon atoms in a ring, or a substituted or unsubstituted aryl group having 6 to 13 carbon atoms in a ring. Moreover, A is represented by General Formula (g1). Furthermore, $X^1$ to $X^4$ each independently represent N or $CR^{14}$. Note that $R^{14}$ represents hydrogen, an alkyl group having 1 to 6 carbon atoms, a substituted or unsubstituted cyclic alkyl group having 3 to 7 carbon atoms in a ring, or a substituted or unsubstituted aryl group having 6 to 13 carbon atoms in a ring.

In General Formula (G1) shown above, the quinoxaline skeleton has a high electron-transport property and the anthracene skeleton has a high stability to holes. The heteroaromatic ring having N at the 3-position from the position bonded to the anthracene skeleton can increase the property of electron injection from an electrode.

Another embodiment of the present invention is an organic compound represented by General Formula (G2) shown below. A heteroaromatic ring directly bonded to the 10-position of an anthracene skeleton has N at the 3-position from the position bonded to the anthracene skeleton.

[Chemical Formula 9]

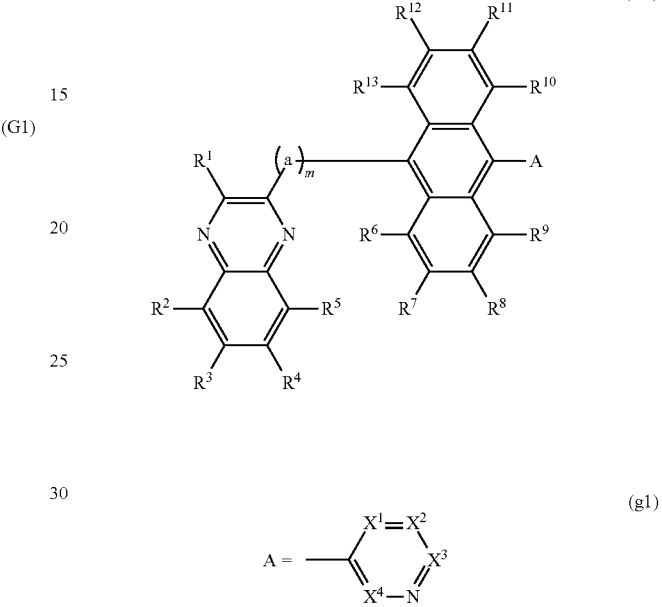

(G2)

(g1)

In General Formula (G2) shown above, a represents a substituted or unsubstituted arylene group having 6 to 13 carbon atoms in a ring. In addition, m is 0, 1, or 2. Note that two arylene groups a when m is 2 may be the same or different. Furthermore, $R^1$ to $R^{13}$ each independently represent hydrogen, an alkyl group having 1 to 6 carbon atoms, a substituted or unsubstituted cyclic alkyl group having 3 to 7 carbon atoms in a ring, or a substituted or unsubstituted aryl group having 6 to 13 carbon atoms in a ring. Moreover, A is represented by General Formula (g1). Furthermore, $X^1$ to $X^4$ each independently represent N or $CR^{14}$. Note that $R^{14}$ represents hydrogen, an alkyl group having 1 to 6 carbon atoms, a substituted or unsubstituted cyclic alkyl group having 3 to 7 carbon atoms in a ring, or a substituted or unsubstituted aryl group having 6 to 13 carbon atoms in a ring.

In General Formula (G2) shown above, the heteroaromatic ring directly bonded to the 10-position of the anthracene skeleton has N at the 3-position from the position bonded to the anthracene skeleton, so that electrons can easily transfer to a quinoxaline skeleton which has a LUMO orbit in the same molecule; therefore the electron-transport property is improved, which is preferable.

Another embodiment of the present invention is an organic compound represented by General Formula (G3) shown below. The 2-position or 3-position of a quinoxaline skeleton is bonded to the 9-position of an anthracene skeleton through one arylene group and a heteroaromatic ring bonded to the 10-position of the anthracene skeleton has N at the 3-position from the position bonded to the anthracene skeleton.

[Chemical Formula 10]

(G3)

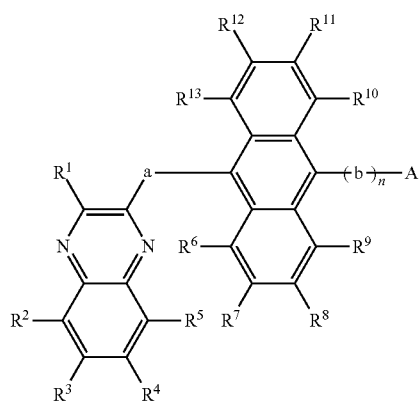

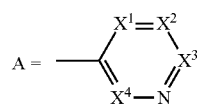
(g1)

In General Formula (G3) shown above, a and b each independently represent a substituted or unsubstituted arylene group having 6 to 13 carbon atoms in a ring. In addition, n is 0, 1, or 2. Note that two arylene groups b when n is 2 may be the same or different. Furthermore, $R^1$ to $R^{13}$ each independently represent hydrogen, an alkyl group having 1 to 6 carbon atoms, a substituted or unsubstituted cyclic alkyl group having 3 to 7 carbon atoms in a ring, or a substituted or unsubstituted aryl group having 6 to 13 carbon atoms in a ring. Moreover, A is represented by General Formula (g1). Furthermore, $X^1$ to $X^4$ each independently represent N or $CR^{14}$. Note that $R^{14}$ represents hydrogen, an alkyl group having 1 to 6 carbon atoms, a substituted or unsubstituted cyclic alkyl group having 3 to 7 carbon atoms in a ring, or a substituted or unsubstituted aryl group having 6 to 13 carbon atoms in a ring.

In General Formula (G3) shown above, the 2-position or 3-position of the quinoxaline skeleton is bonded to the 9-position of the anthracene skeleton through one arylene group, so that the steric hindrance around the quinoxaline skeleton is reduced and thus the electron-transport property is improved, which is preferable. Note that the reduction in the steric hindrance in a molecule allows smooth electron transfer, whereby the electron-transport property is improved. In view of electron transfer in a molecule, electrons in one molecule are appropriately distant from each other so that the electrons easily transfer to the quinoxaline skeleton having a LUMO orbit, which is preferable.

Another embodiment of the present invention is an organic compound represented by General Formula (G4) shown below. The 2-position or 3-position of a quinoxaline skeleton is directly bonded to the 9-position of an anthracene skeleton through one arylene group and a heteroaromatic ring bonded to the 10-position of the anthracene skeleton has N at the 3-position from the position bonded to the anthracene skeleton.

[Chemical Formula 11]

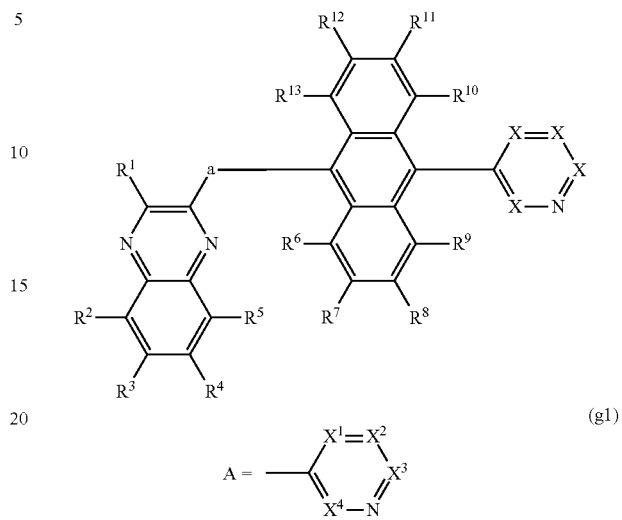

In General Formula (G4) shown above, a represents a substituted or unsubstituted arylene group having 6 to 13 carbon atoms in a ring. Furthermore, $R^1$ to $R^{13}$ each independently represent hydrogen, an alkyl group having 1 to 6 carbon atoms, a substituted or unsubstituted cyclic alkyl group having 3 to 7 carbon atoms in a ring, or a substituted or unsubstituted aryl group having 6 to 13 carbon atoms in a ring. Moreover, A is represented by General Formula (g1). Furthermore, $X^1$ to $X^4$ each independently represent N or $CR^{14}$. Note that $R^{14}$ represents hydrogen, an alkyl group having 1 to 6 carbon atoms, a substituted or unsubstituted cyclic alkyl group having 3 to 7 carbon atoms in a ring, or a substituted or unsubstituted aryl group having 6 to 13 carbon atoms in a ring.

In General Formula (G4) shown above, the 2-position or 3-position of the quinoxaline skeleton is bonded to the 9-position of the anthracene skeleton through one arylene group, so that the steric hindrance around the quinoxaline skeleton is reduced, which is preferable. Note that the reduction in the steric hindrance in a molecule allows smooth electron transfer, whereby the electron-transport property is improved. In view of electron transfer in a molecule, since the organic compound has, in addition to the above structure, a structure in which the heteroaromatic ring directly bonded to the 10-position of the anthracene skeleton has N at the 3-position from the position bonded to the anthracene skeleton, electrons in one molecule are appropriately distant from each other so that the electrons easily transfer to the quinoxaline skeleton having a LUMO orbit, which is preferable.

Another embodiment of the present invention is an organic compound in which a in General Formula (G4) shown above represents a substituted or unsubstituted phenylene group. Note that a represents a substituted or unsubstituted phenylene group, so that the steric hindrance around the quinoxaline skeleton is reduced and thus the electron-transport property is improved, which is preferable. Moreover, electrons in one molecule are appropriately distant from each other so that the electrons easily transfer to the quinoxaline skeleton having a LUMO orbit, which is preferable.

Another embodiment of the present invention is an organic compound in which General Formula (g1) shown above is represented by any one of General Formulae (g1-1) to (g1-3) shown below.

[Chemical Formulae 12]

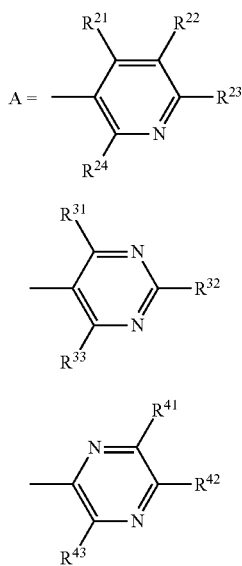

(g1-1)

(g1-2)

(g1-3)

In General Formulae (g1-1) to (g1-3) shown above, $R^{21}$ to $R^{24}$, $R^{31}$ to $R^{33}$, and $R^{41}$ to $R^{43}$ each represent hydrogen, an alkyl group having 1 to 6 carbon atoms, a substituted or unsubstituted cyclic alkyl group having 3 to 7 carbon atoms in a ring, or a substituted or unsubstituted aryl group having 6 to 13 carbon atoms in a ring.

Another embodiment of the present invention is an organic compound in which General Formula (g1) shown above is represented by any one of General Formulae (g1-4) to (g1-6) shown below.

[Chemical Formulae 13]

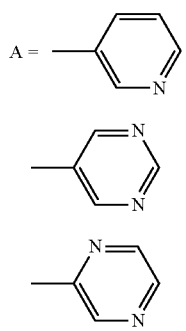

(g1-4)

(g1-5)

(g1-6)

Note that substitution in the organic compounds represented by General Formulae (G1) to (G4) shown above is preferably substitution by a substituent such as an alkyl group having 1 to 6 carbon atoms, e.g., a methyl group, an ethyl group, an n-propyl group, an isopropyl group, a sec-butyl group, a tert-butyl group, an n-pentyl group, or an n-hexyl group, or substitution by a substituent such as an aryl group having 6 to 13 carbon atoms, e.g., a phenyl group, an o-tolyl group, an m-tolyl group, a p-tolyl group, a 1-naphthyl group, a 2-naphthyl group, a 2-biphenyl group, a 3-biphenyl group, a 4-biphenyl group, a fluoren-2-yl group, or a fluoren-4-yl group. These substituents may be bonded to each other to form a ring. For example, in the case where the aryl group is a fluoren-2-yl group having two phenyl groups as substituents at the 9-position, the phenyl groups may be bonded to each other to form a spiro-9,9'-bifluoren-2-yl group. More specifically, a phenyl group, a tolyl group, a xylyl group, a biphenyl group, an indenyl group, a naphthyl group, a fluorenyl group, and the like can be given.

In each of the organic compounds represented by General Formulae (G1) to (G4) shown above, specific examples of the arylene group having 6 to 13 carbon atoms in a ring in the formulae include a phenylene group, a naphthalenediyl group, a biphenyldiyl group, and a fluorenediyl group.

In the organic compounds represented by General Formulae (G1) to (G4) shown above, specific examples of the alkyl group having 1 to 6 carbon atoms which is represented by any of $R^1$ to $R^{13}$, $R^{14}$, $R^{21}$ to $R^{24}$, $R^{31}$ to $R^{33}$, and $R^{41}$ to $R^{43}$ in the formulae include a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a sec-hexyl group, a tert-hexyl group, a neohexyl group, a 3-methylpentyl group, a 2-methylpentyl group, a 2-ethylbutyl group, a 1,2-dimethylbutyl group, and a 2,3-dimethylbutyl group.

In the organic compounds represented by General Formulae (G1) to (G4) shown above, specific examples of the cyclic alkyl group having 3 to 7 carbon atoms in a ring which is represented by any of $R^1$ to $R^{13}$, $R^{14}$, $R^{21}$ to $R^{24}$, $R^{31}$ to $R^{33}$ and $R^{41}$ to $R^{43}$ in the formulae include a cyclopropyl group, a cyclobutyl group, a cyclopentyl group, a cyclohexyl group, and a cycloheptyl group.

In the organic compounds represented by General Formulae (G1) to (G4) shown above, specific examples of the aryl group having 6 to 13 carbon atoms in a ring which is represented by any of $R^1$ to $R^{13}$, $R^{14}$, $R^{21}$ to $R^{24}$, $R^{31}$ to $R^{33}$ and $R^{41}$ to $R^{43}$ in the formulae include a phenyl group, a biphenyl group, a naphthyl group, an indenyl group, and a fluorenyl group.

Next, specific structural formulae of the aforementioned organic compounds of embodiments of the present invention are shown below.

[Chemical Formulae 14]

(100)

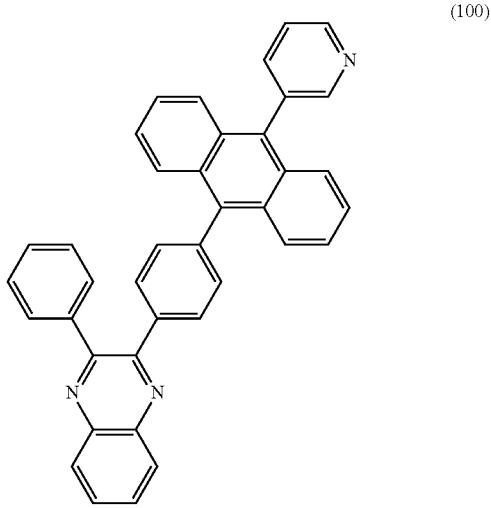

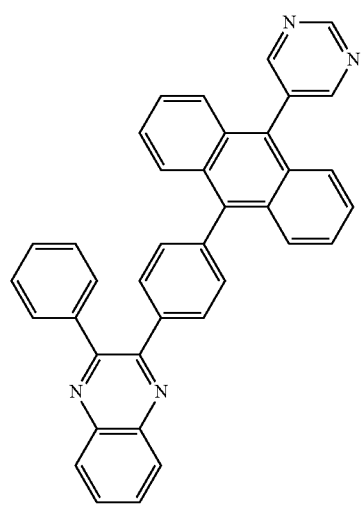
(101)
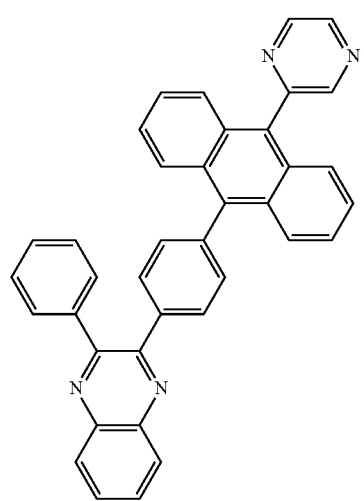
(102)
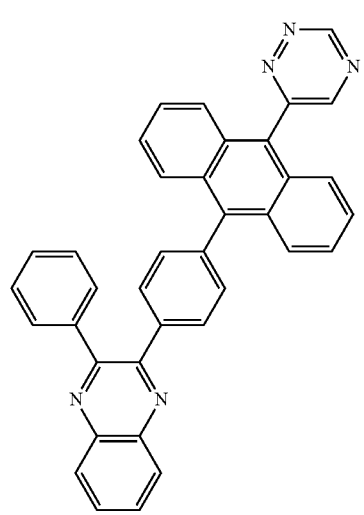
(103)
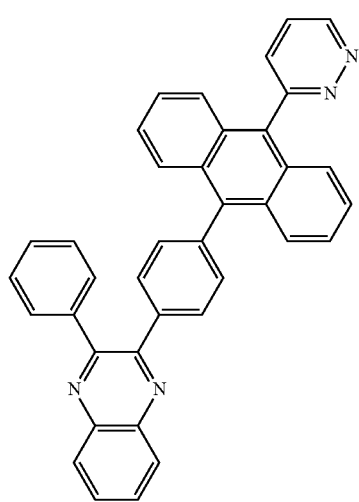
(104)
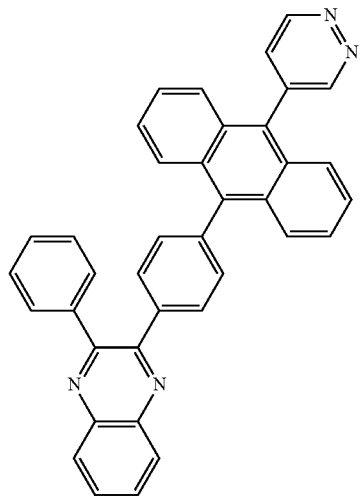
(105)
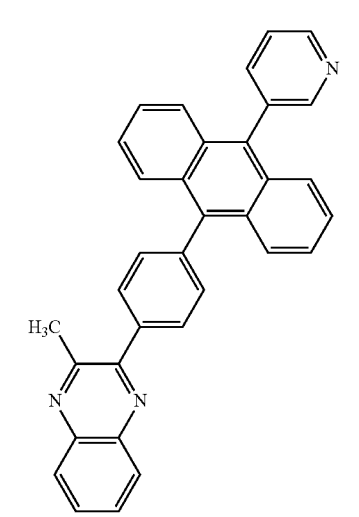
(106)

(107)
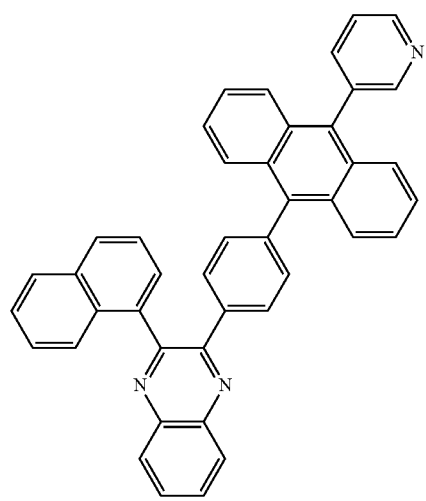
(108)
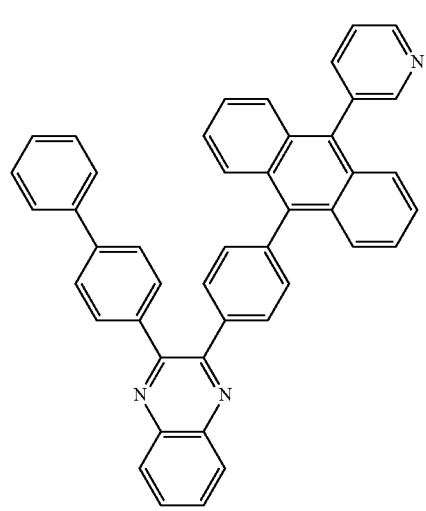
(109)
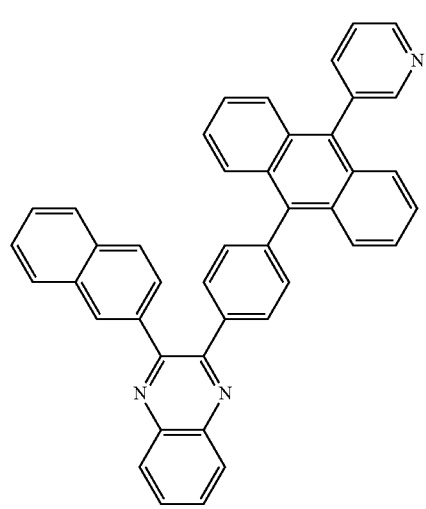
(110)
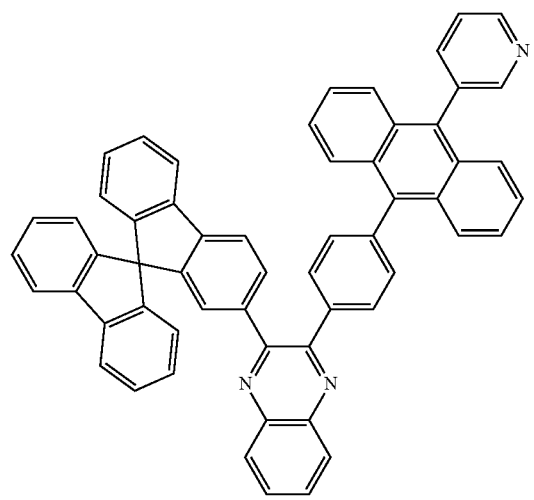
[Chemical Formulae 15]
(111)
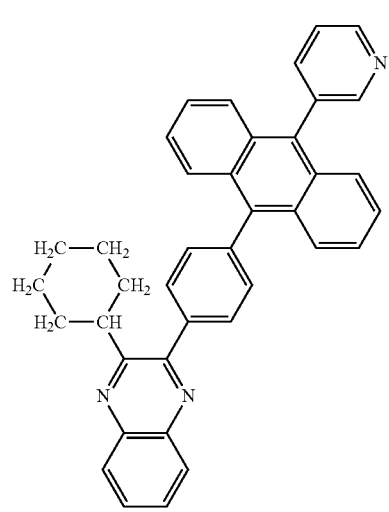
(112)
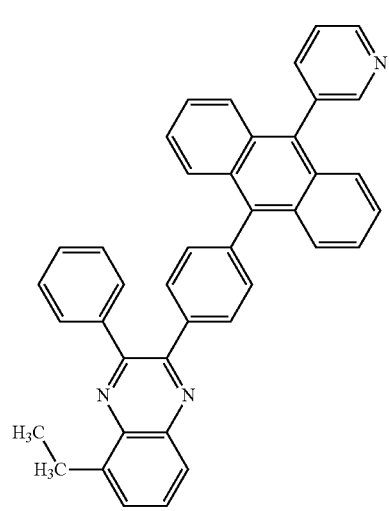

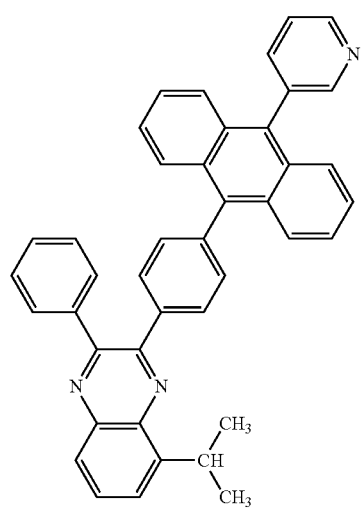
(113)
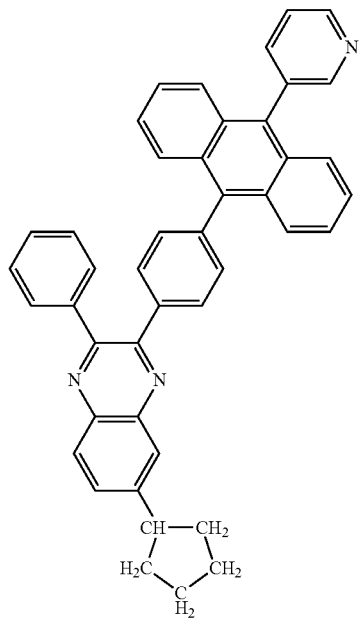
(115)
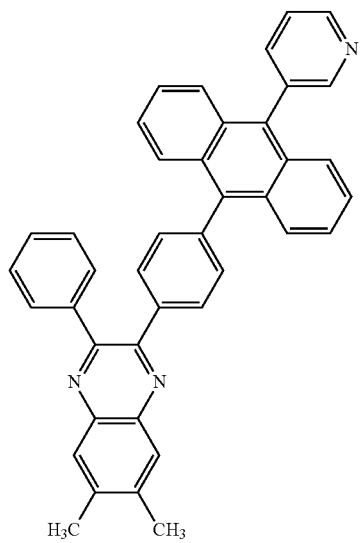
(116)
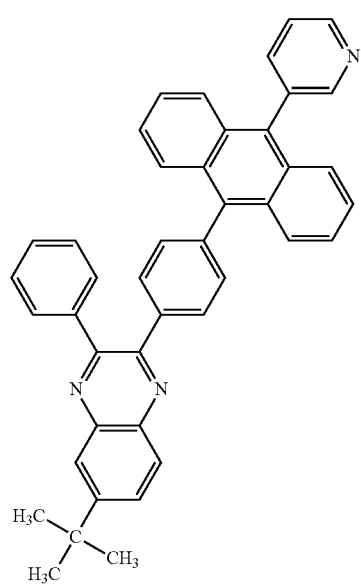
(114)
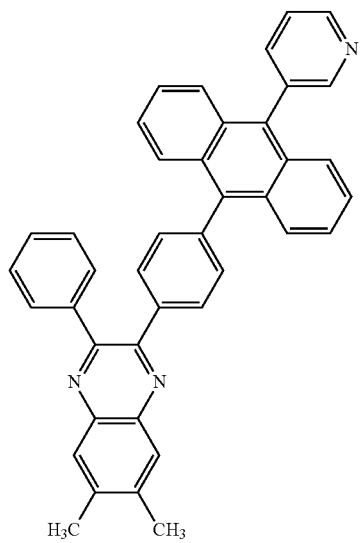
(117)

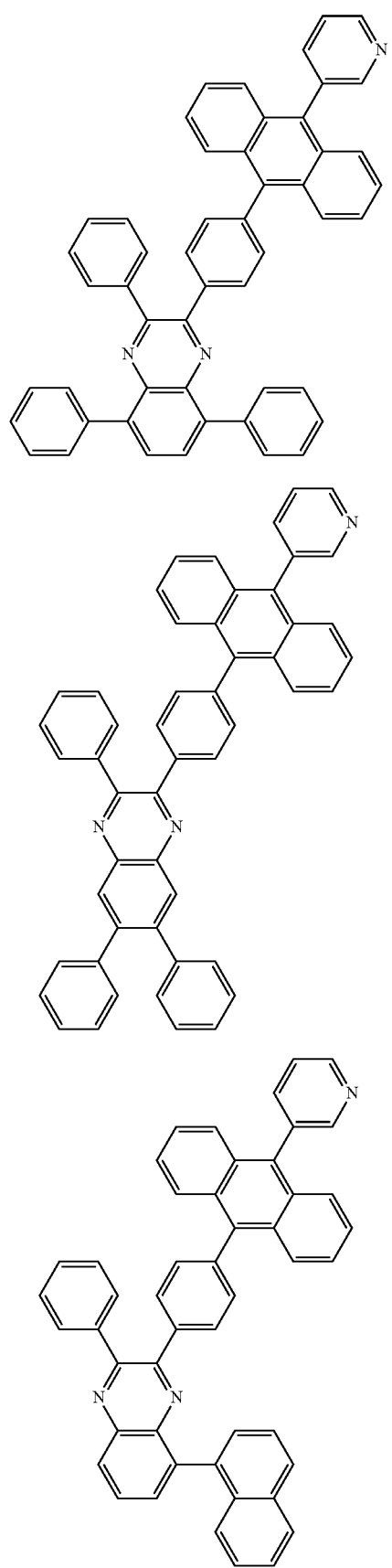
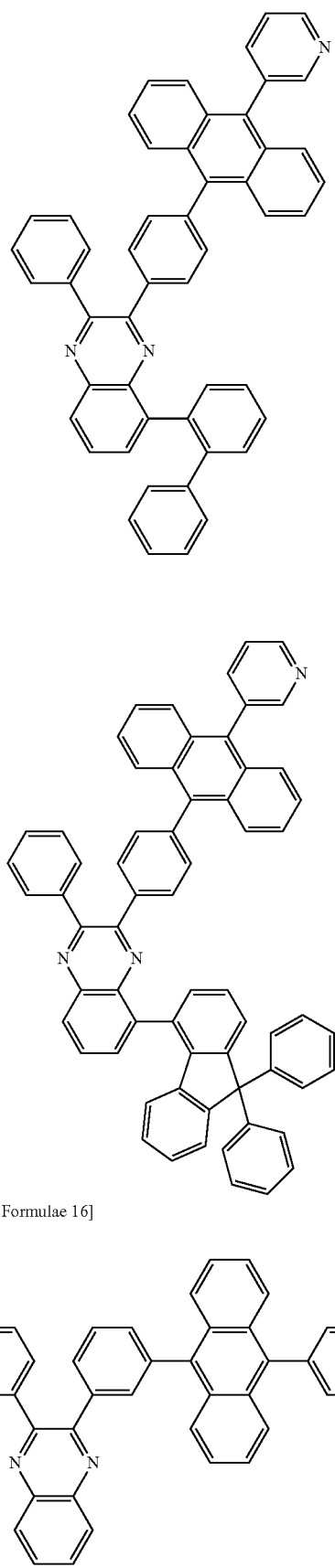
[Chemical Formulae 16]

(124)
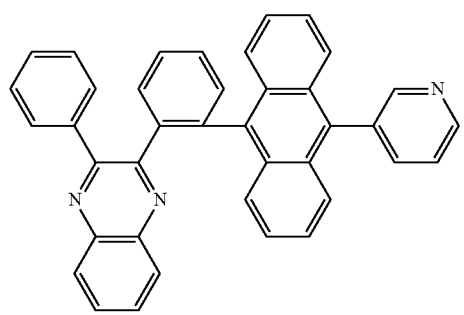
(125)
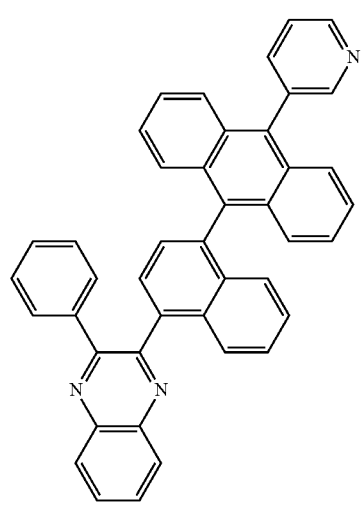
(126)
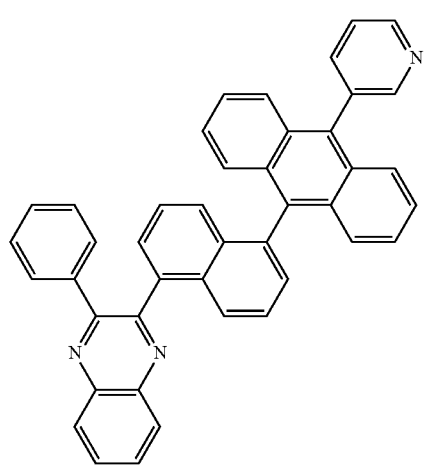
(127)
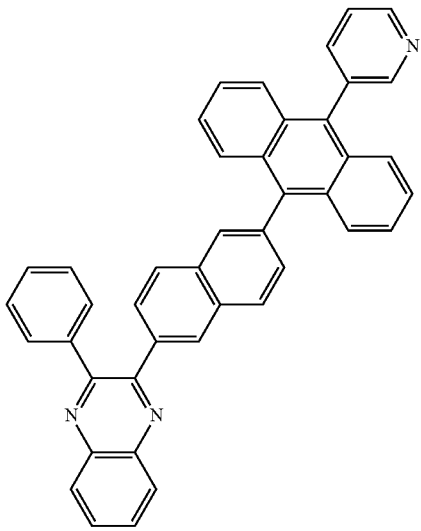
(128)
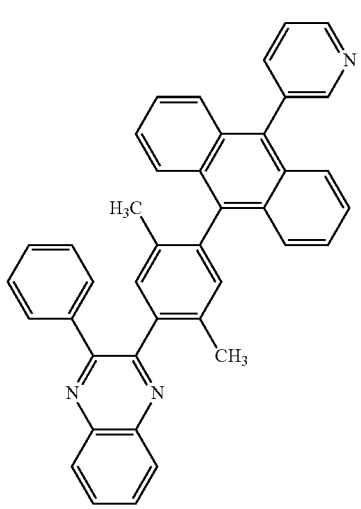
(129)
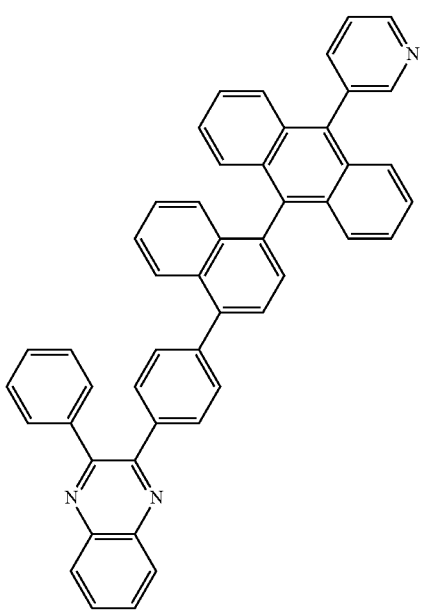

[Chemical Formulae 17]
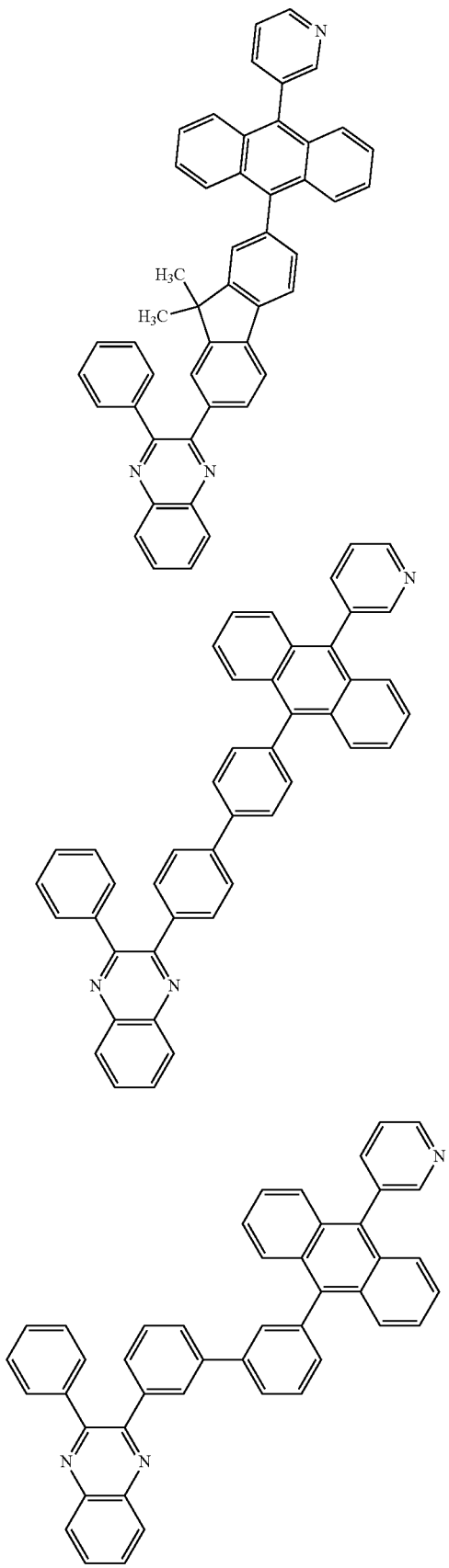
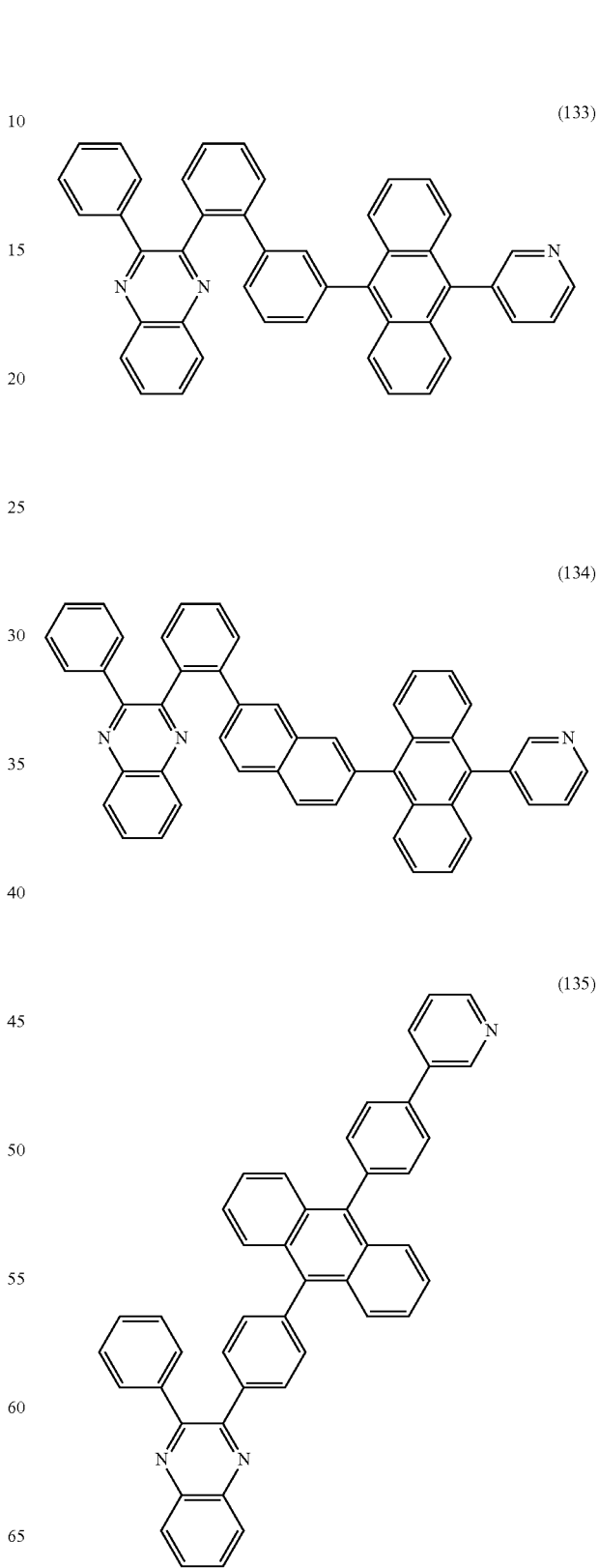

-continued
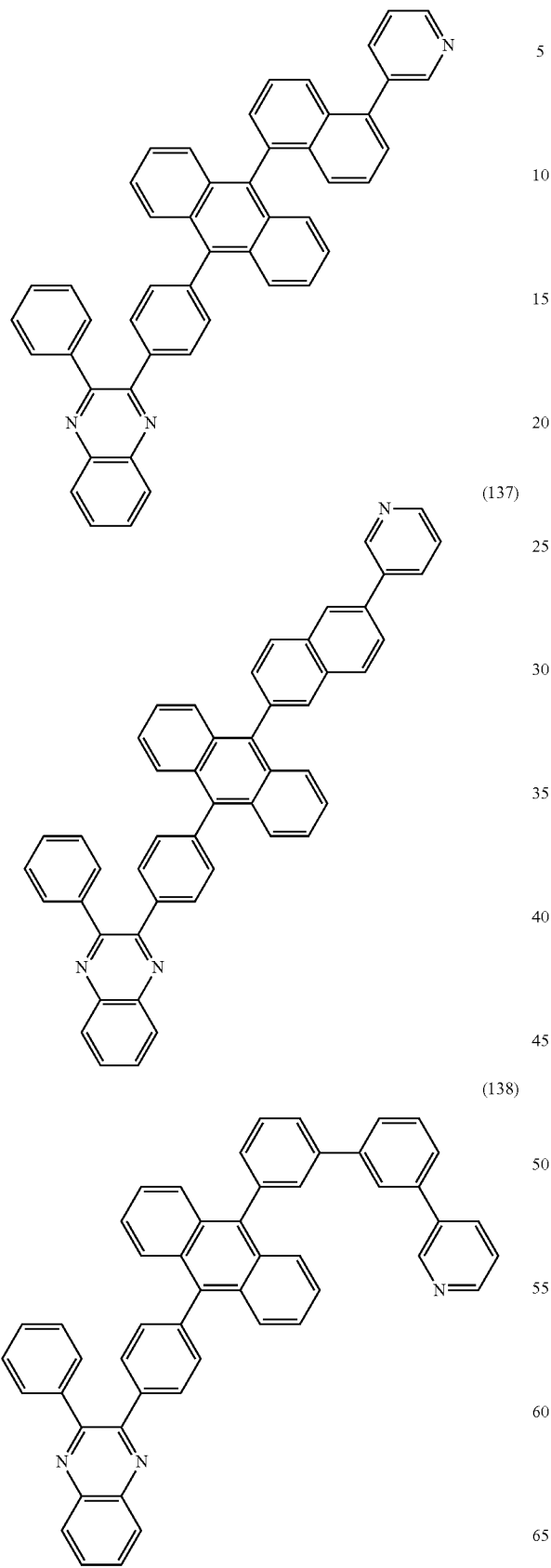
(136)
(137)
(138)
(139)
(140)

[Chemical Formulae 18]
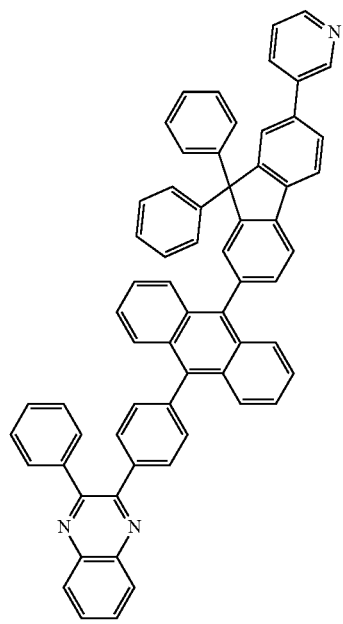
(141)
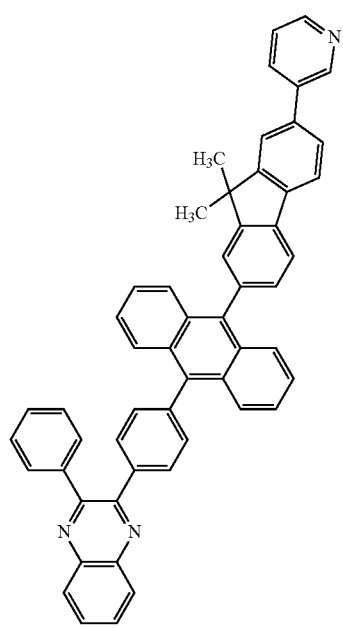
(142)
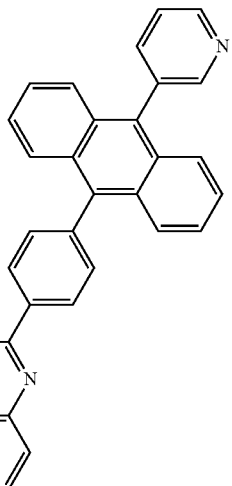
(143)
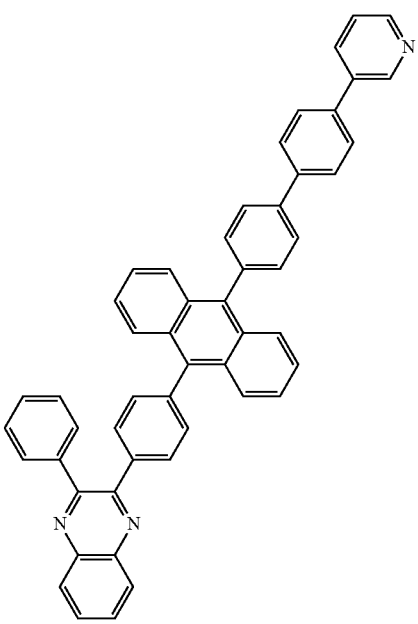
(144)

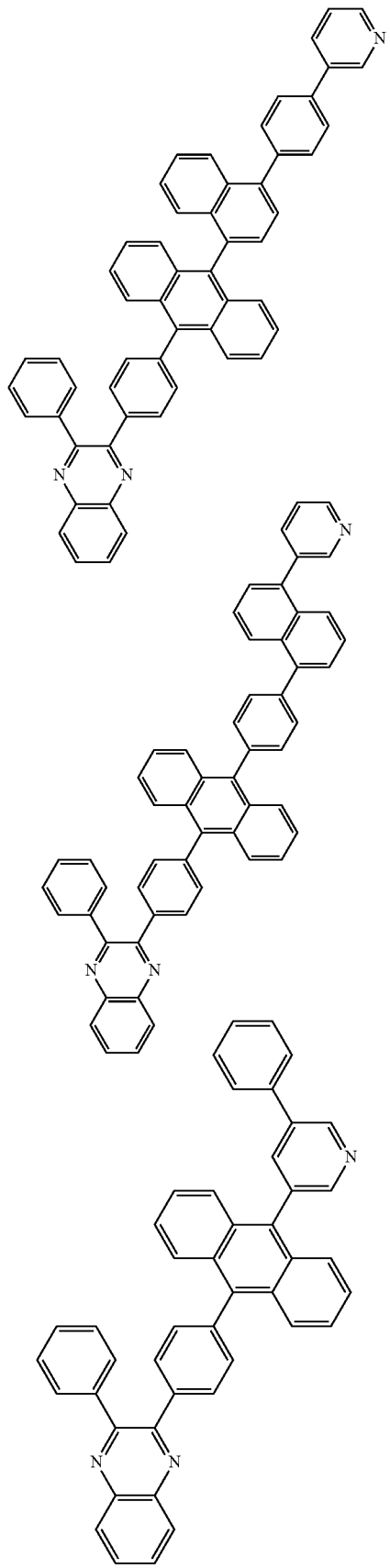
(145)
(146)
(147)
(148)
(149)

(150)
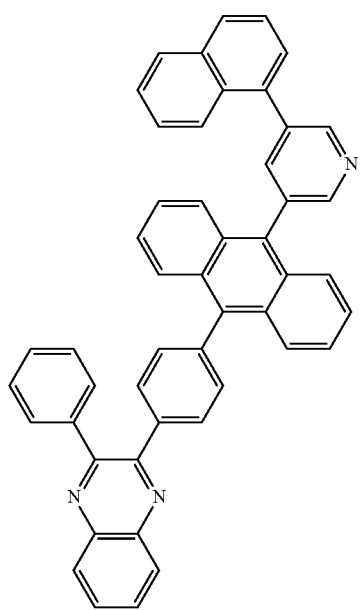
[Chemical Formulae 19]
(151)
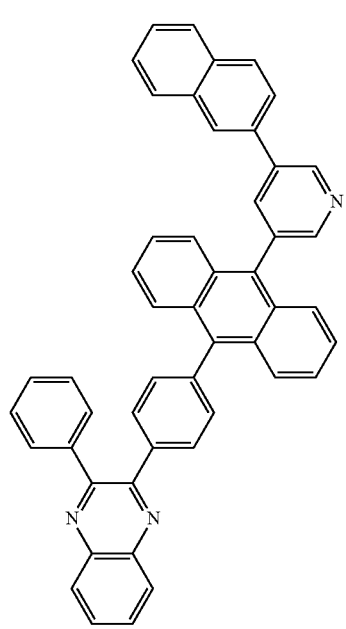
(152)
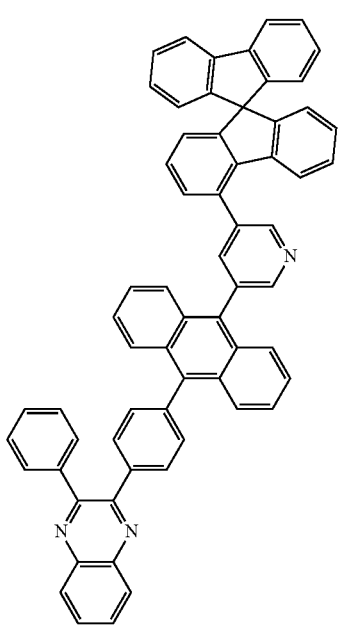
(153)
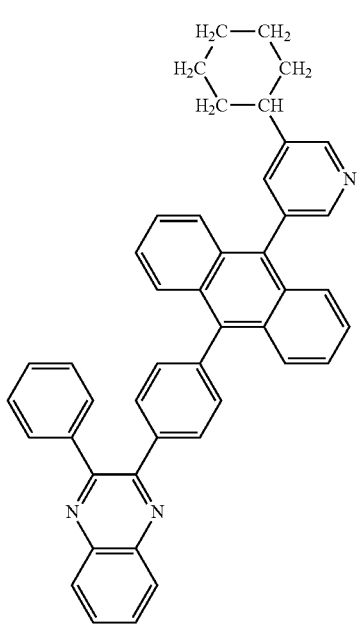

(154)
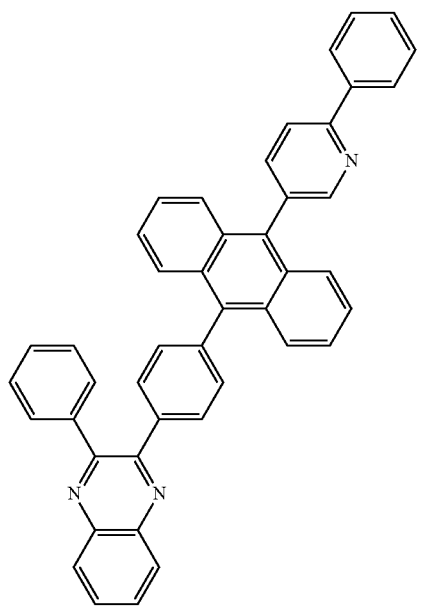
(155)
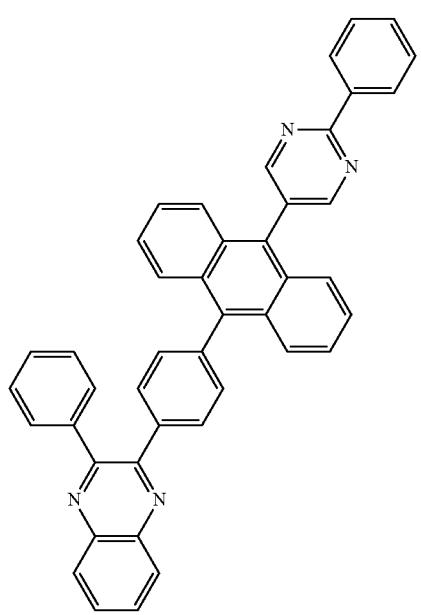
(156)
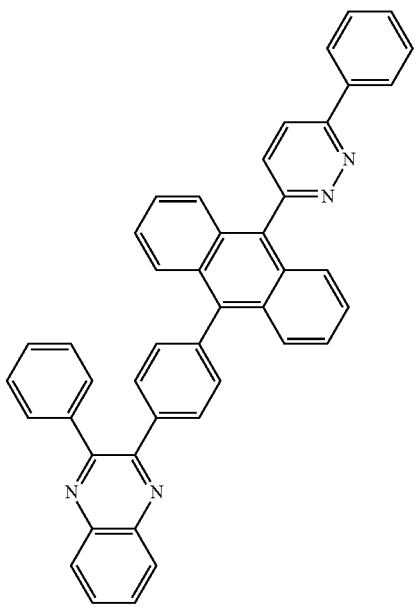
(157)
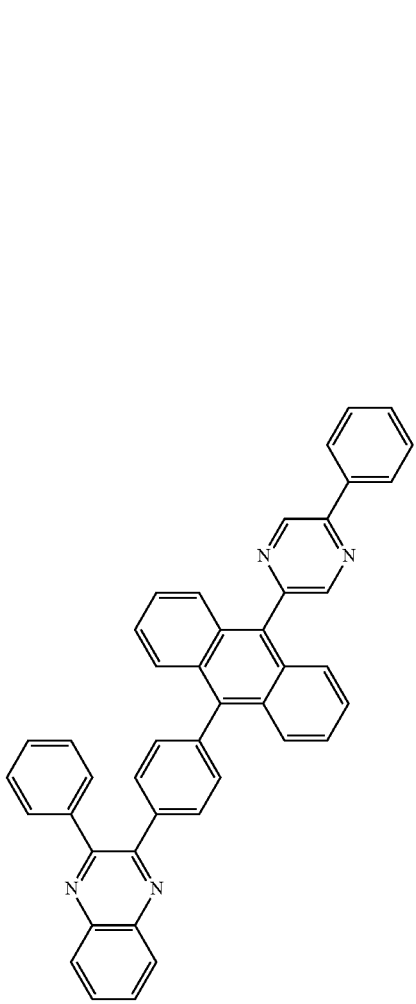

(158)
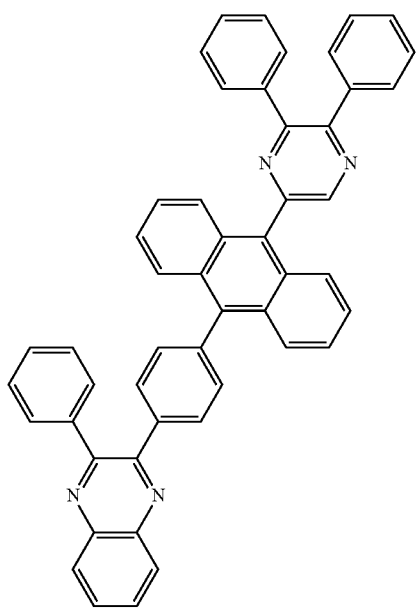
(159)
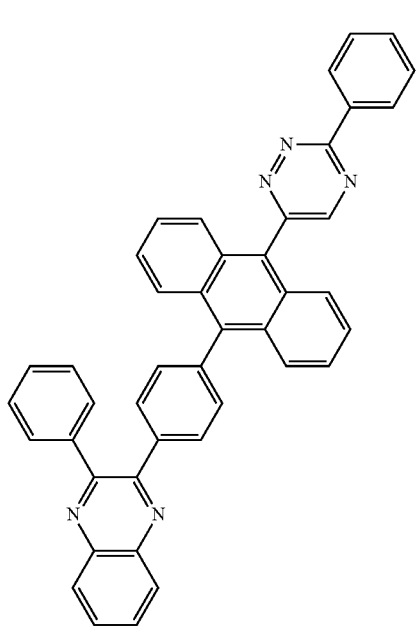
(161)
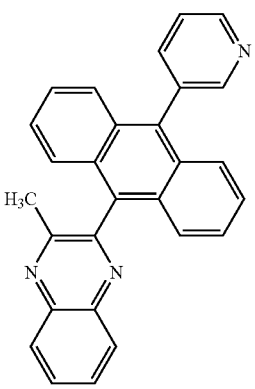
(162)
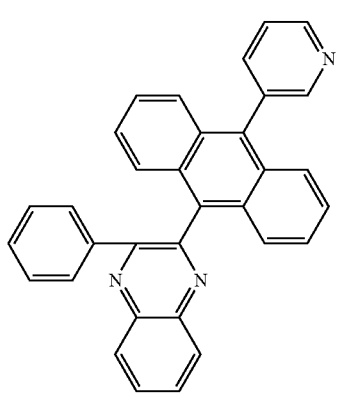
[Chemical Formulae 20]
(163)
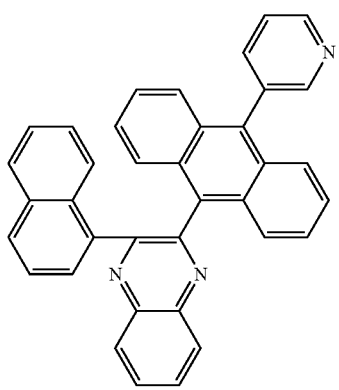
(160)
(164)
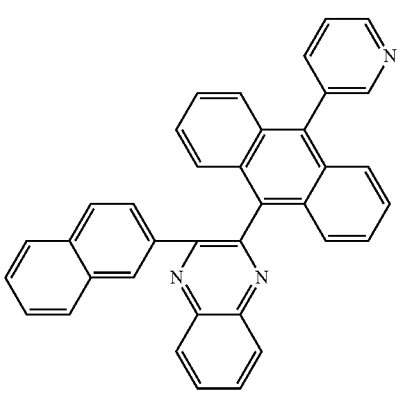

-continued
(165)
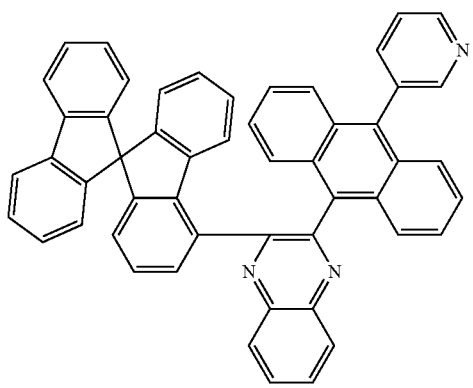
(166)
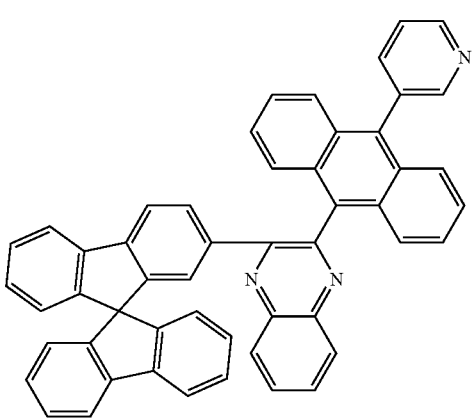
(167)
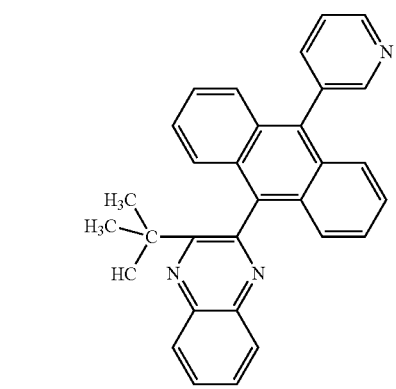
(168)
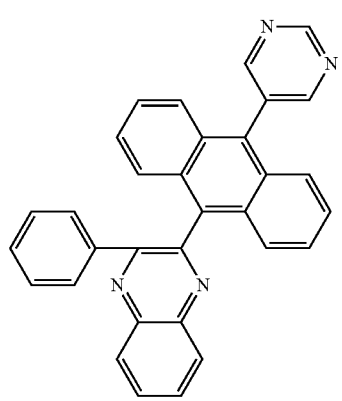
(169)
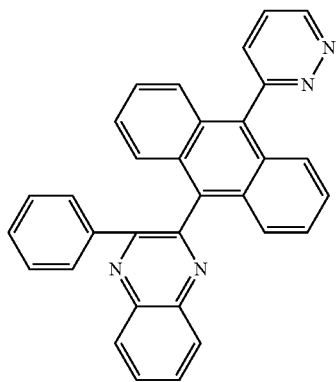
(170)
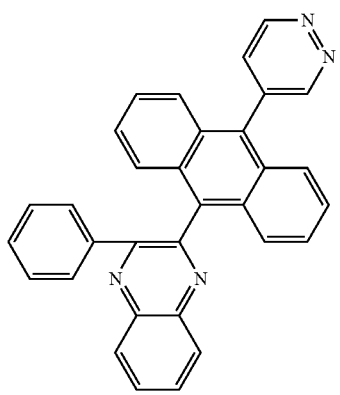
(171)
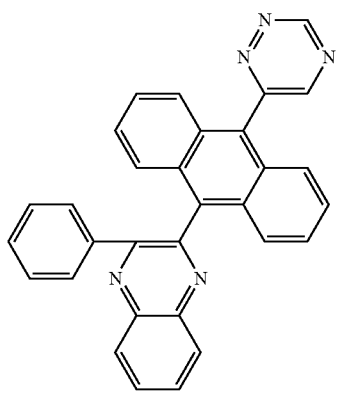
(172)
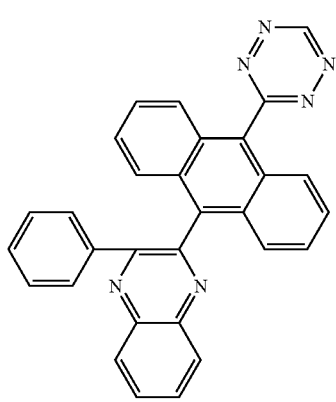

-continued

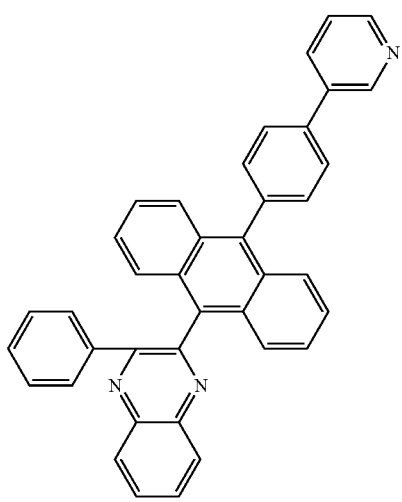

(173)

(174)

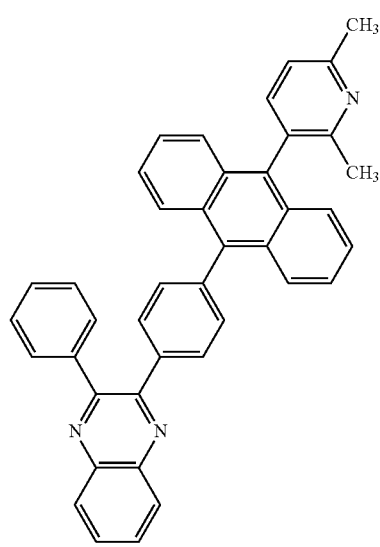

(175)

The organic compounds represented by Structural Formulae (100) to (175) shown above are examples of the organic compound of one embodiment of the present invention represented by any one of General Formulae (G1) to (G4) shown above. Note that the organic compound of one embodiment of the present invention is not limited to these examples.

Next, an example of a method for synthesizing the organic compound of one embodiment of the present invention represented by General Formula (G1) shown below will be described.

[Chemical Formula 21]

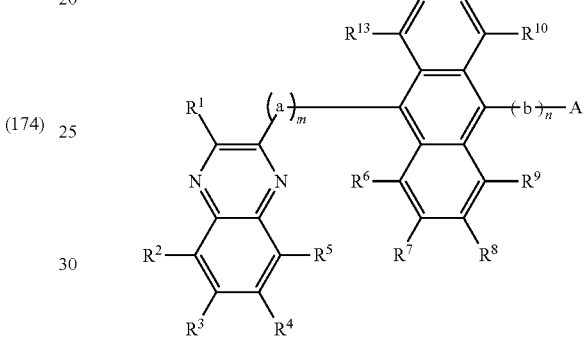

(G1)

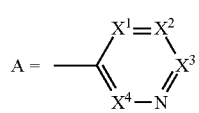

(g1)

In General Formula (G1), a and b each independently represent a substituted or unsubstituted arylene group having 6 to 13 carbon atoms in a ring. In addition, m and n are each independently 0, 1, or 2. Note that two arylene groups a when m is 2 or two arylene groups b when n is 2 may be the same or different. Furthermore, $R^1$ to $R^{13}$ each independently represent hydrogen, an alkyl group having 1 to 6 carbon atoms, a substituted or unsubstituted cyclic alkyl group having 3 to 7 carbon atoms in a ring, or a substituted or unsubstituted aryl group having 6 to 13 carbon atoms in a ring. Moreover, A is represented by General Formula (g1). Furthermore, $X^1$ to $X^4$ each independently represent N or $CR^{14}$. Note that $R^{14}$ represents hydrogen, an alkyl group having 1 to 6 carbon atoms, a substituted or unsubstituted cyclic alkyl group having 3 to 7 carbon atoms in a ring, or a substituted or unsubstituted aryl group having 6 to 13 carbon atoms in a ring.

As shown in Synthesis Scheme (A-1) shown below, an organoboron compound or a boronic acid of a quinoxaline derivative (Compound 1) is coupled with a halide of an anthracene derivative or an anthracene derivative having a triflate group as a substituent (Compound 2) by the Suzuki-Miyaura reaction, whereby the organic compound represented by General Formula (G1) can be obtained.

[Chemical Formulae 22]

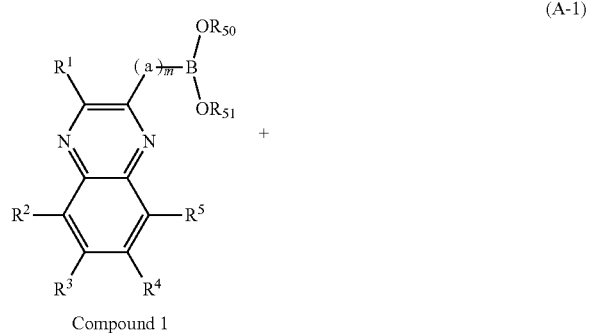

Compound 1

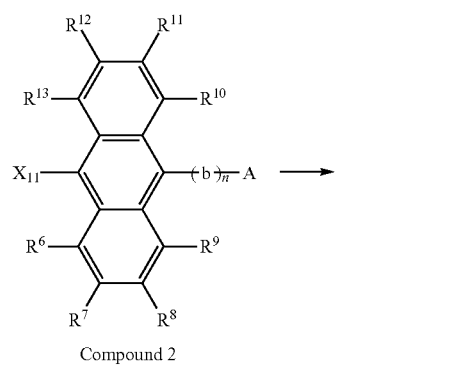

Compound 2

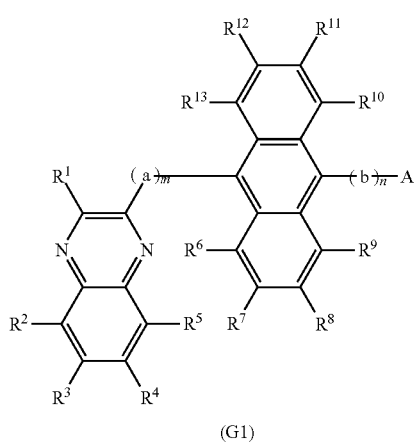

(G1)

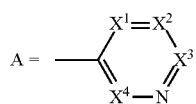

(g1)

In Synthesis Scheme (A-1), a and b each independently represent a substituted or unsubstituted arylene group having 6 to 13 carbon atoms in a ring. In addition, m and n are each independently 0, 1, or 2. Note that two arylene groups a when m is 2 or two arylene groups b when n is 2 may be the same or different. Furthermore, $R^1$ to $R^{14}$ each independently represent hydrogen, an alkyl group having 1 to 6 carbon atoms, a substituted or unsubstituted cyclic alkyl group having 3 to 7 carbon atoms in a ring, or a substituted or unsubstituted aryl group having 6 to 13 carbon atoms in a ring. Moreover, A is represented by General Formula (g1). Furthermore, $X^1$ to $X^4$ each independently represent N or $CR^{14}$. Note that $R^{14}$ represents hydrogen, an alkyl group having 1 to 6 carbon atoms, a substituted or unsubstituted cyclic alkyl group having 3 to 7 carbon atoms in a ring, or a substituted or unsubstituted aryl group having 6 to 13 carbon atoms in a ring.

In Synthesis Scheme (A-1), $R^{50}$ and $R^{51}$ may be bonded to each other to form a ring. In addition, $X^{11}$ represents halogen or a triflate group.

Examples of a palladium catalyst that can be used in Synthesis Scheme (A-1) include, but are not limited to, palladium(II) acetate, tetrakis(triphenylphosphine)palladium(0), and bis(triphenylphosphine)palladium(II) dichloride.

Examples of a ligand of the palladium catalyst that can be used in Synthesis Scheme (A-1) include, but are not limited to, tri(ortho-tolyl)phosphine, triphenylphosphine, and tricyclohexylphosphine.

Examples of a base that can be used in Synthesis Scheme (A-1) include, but are not limited to, organic bases such as sodium tert-butoxide and inorganic bases such as potassium carbonate and sodium carbonate.

Examples of a solvent that can be used in Synthesis Scheme (A-1) include, but not limited to, a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; and a mixed solvent of water and an ether such as ethylene glycol dimethyl ether. In particular, a mixed solvent of toluene and water, a mixed solvent of toluene, ethanol, and water, or a mixed solvent of water and an ether such as ethylene glycol dimethyl ether is preferred.

The Suzuki-Miyaura coupling reaction shown in Synthesis Scheme (A-1) may be replaced with a cross coupling reaction using an organoaluminum compound, an organozirconium compound, an organozinc compound, an organotin compound, or the like as well as the organoboron compound or boronic acid represented by Compound 1. However, the present invention is not limited thereto.

In the Suzuki-Miyaura coupling reaction shown above, an organoboron compound or a boronic acid of the anthracene derivative may be coupled with a halide of the quinoxaline derivative or the quinoxaline derivative having a triflate group as a substituent. Specifically, as shown in Synthesis Scheme (A-2) shown below, an organoboron compound or a boronic acid of an anthracene derivative (Compound 3) is coupled with a halide of a heteroaromatic compound derivative or a heteroaromatic compound derivative having a triflate group as a substituent (Compound 4) by the Suzuki-Miyaura reaction, whereby the organic compound represented by General Formula (G1) can be obtained.

[Chemical Formulae 23]

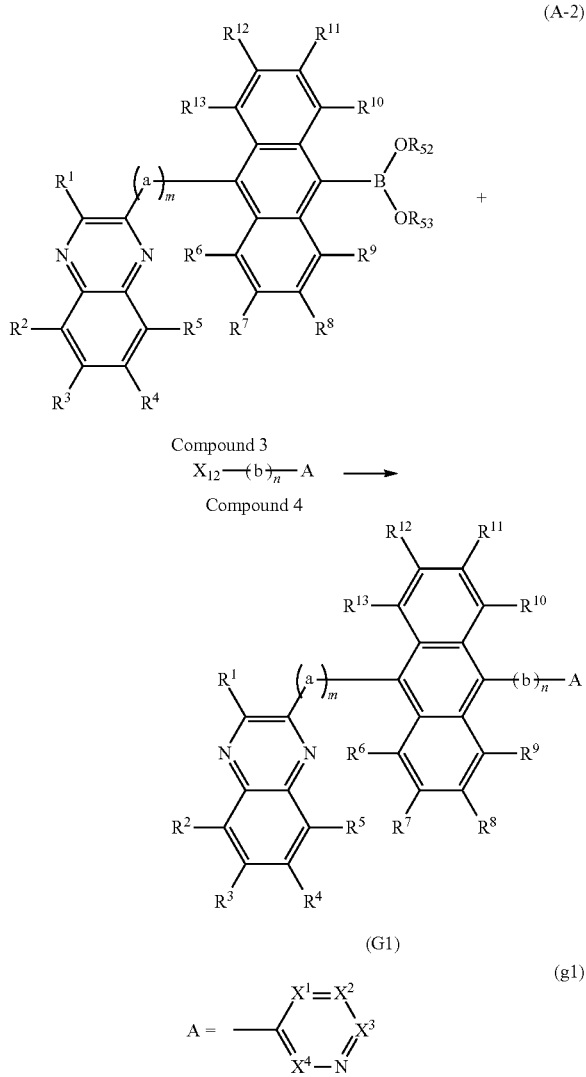

In Synthesis Scheme (A-2) shown above, a and b each independently represent a substituted or unsubstituted arylene group having 6 to 13 carbon atoms in a ring. In addition, m and n are each independently 0, 1, or 2. Note that two arylene groups a when m is 2 or two arylene groups b when n is 2 may be the same or different. Furthermore, $R^1$ to $R^{13}$ each independently represent hydrogen, an alkyl group having 1 to 6 carbon atoms, a substituted or unsubstituted cyclic alkyl group having 3 to 7 carbon atoms in a ring, or a substituted or unsubstituted aryl group having 6 to 13 carbon atoms in a ring. Moreover, A is represented by General Formula (g1). Furthermore, $X^1$ to $X^4$ each independently represent N or $CR^{14}$. Note that $R^{14}$ represents hydrogen, an alkyl group having 1 to 6 carbon atoms, a substituted or unsubstituted cyclic alkyl group having 3 to 7 carbon atoms in a ring, or a substituted or unsubstituted aryl group having 6 to 13 carbon atoms in a ring.

In Synthesis Scheme (A-2), $R^{52}$ and $R^{53}$ may be bonded to each other to form a ring. In addition, $X^{12}$ represents halogen or a triflate group.

Examples of a palladium catalyst that can be used in Synthesis Scheme (A-2) include, but are not limited to, palladium(II) acetate, tetrakis(triphenylphosphine)palladium(0), and bis(triphenylphosphine)palladium(II) dichloride. Examples of a ligand of the palladium catalyst that can be used in Synthesis Scheme (A-2) include, but are not limited to, tri(ortho-tolyl)phosphine, triphenylphosphine, and tricyclohexylphosphine.

Examples of a base that can be used in Synthesis Scheme (A-2) include, but are not limited to, organic bases such as sodium tert-butoxide and inorganic bases such as potassium carbonate and sodium carbonate.

Examples of a solvent that can be used in Synthesis Scheme (A-2) include, but not limited to, a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; and a mixed solvent of water and an ether such as ethylene glycol dimethyl ether. In particular, a mixed solvent of toluene and water, a mixed solvent of toluene, ethanol, and water, or a mixed solvent of water and an ether such as ethylene glycol dimethyl ether is preferred.

The Suzuki-Miyaura coupling reaction shown in Synthesis Scheme (A-2) may be replaced with a cross coupling reaction using an organoaluminum compound, an organozirconium compound, an organozinc compound, an organotin compound, or the like as well as the organoboron compound or boronic acid represented by Compound 3. However, the present invention is not limited thereto.

Embodiment 2

In this embodiment, light-emitting devices of embodiments of the present invention will be described.

<Structure Example of Light-Emitting Device>

FIG. 1A illustrates an example of a light-emitting device including an EL layer that includes a light-emitting layer between a pair of electrodes. Specifically, an EL layer 103 is interposed between a first electrode 101 and a second electrode 102. For example, in the case where the first electrode 101 is an anode, the EL layer 103 has a structure in which a hole-injection layer 111, a hole-transport layer 112, a light-emitting layer 113, an electron-transport layer 114, and an electron-injection layer 115 are stacked as functional layers in this order.

Embodiments of the present invention also include light-emitting devices having other structures, such as a light-emitting device that can be driven at low voltage by having a structure (tandem structure) in which a plurality of EL layers are provided between a pair of electrodes and a charge-generation layer is provided between the EL layers, and a light-emitting device having a micro-optical resonator (microcavity) structure between a pair of electrodes and thus having improved optical characteristics. The charge-generation layer has a function of injecting electrons into one of the adjacent EL layers and injecting holes into the other of the EL layers when a voltage is applied between the first electrode 101 and the second electrode 102.

At least one of the first electrode 101 and the second electrode 102 of the light-emitting device is a light-transmitting electrode (e.g., a transparent electrode or a transflective electrode). In the case where the light-transmitting electrode is a transparent electrode, the transparent electrode has a visible light transmittance higher than or equal to 40%. In the case where the light-transmitting electrode is a transflective electrode, the transflective electrode has a visible light reflectance higher than or equal to 20% and lower than or equal to 80%, preferably higher than or equal to 40% and lower than or equal to 70%. These electrodes preferably have a resistivity of $1\times10^{-2}$ Ωcm or less.

Furthermore, when one of the first electrode 101 and the second electrode 102 is a reflective electrode in the light-emitting device of one embodiment of the present invention, the visible light reflectance of the reflective electrode is higher than or equal to 40% and lower than or equal to 100%, preferably higher than or equal to 70% and lower than or equal to 100%. This electrode preferably has a resistivity of $1\times10^{-2}$ Ω/cm or less.

<First Electrode and Second Electrode>

As materials for the first electrode 101 and the second electrode 102, any of the following materials can be used in an appropriate combination as long as the above functions of the electrodes can be fulfilled. For example, a metal, an alloy, an electrically conductive compound, a mixture of these, and the like can be used as appropriate. Specifically, an In—Sn oxide (also referred to as ITO), an In—Si—Sn oxide (also referred to as ITSO), an In—Zn oxide, or an In—W—Zn oxide can be used. In addition, it is possible to use a metal such as aluminum (Al), titanium (Ti), chromium (Cr), manganese (Mn), iron (Fe), cobalt (Co), nickel (Ni), copper (Cu), gallium (Ga), zinc (Zn), indium (In), tin (Sn), molybdenum (Mo), tantalum (Ta), tungsten (W), palladium (Pd), gold (Au), platinum (Pt), silver (Ag), yttrium (Y), or neodymium (Nd) or an alloy containing an appropriate combination of any of these metals. It is also possible to use a Group 1 element or a Group 2 element in the periodic table that is not described above (e.g., lithium (Li), cesium (Cs), calcium (Ca), or strontium (Sr)), a rare earth metal such as europium (Eu) or ytterbium (Yb), an alloy containing an appropriate combination of any of these elements, graphene, or the like.

For fabrication of these electrodes, a sputtering method or a vacuum evaporation method can be used.

<Hole-Injection Layer>

The hole-injection layer 111 is a layer including an organic acceptor material and a hole-transport material, preferably a hole-transport material with a deep HOMO level. The organic acceptor material exhibits an electron-accepting property with respect to the hole-transport material with a deep HOMO level. The hole-transport material with a deep HOMO level has a relatively deep HOMO level which is higher than or equal to −5.7 eV and lower than or equal to −5.4 eV. The hole-transport material with a relatively deep HOMO level facilitates hole injection into the hole-transport layer 112.

As the organic acceptor material, organic compounds having an electron-withdrawing group (in particular, a cyano group or a halogen group such as a fluoro group) can be used, for example. A substance that exhibits an electron-accepting property with respect to the hole-transport material is selected from such organic compounds as appropriate. Examples of such an organic compound include 7,7,8,8-tetracyano-2,3,5,6-tetrafluoroquinodimethane (abbreviation: F4-TCNQ), chloranil, 2,3,6,7,10,11-hexacyano-1,4,5,8,9,12-hexaazatriphenylene (abbreviation: HAT-CN), 1,3,4,5,7,8-hexafluorotetracyano-naphthoquinodimethane (abbreviation: F6-TCNNQ), and 2-(7-dicyanomethylene-1,3,4,5,6,8,9,10-octafluoro-7H-pyren-2-ylidene)malononitrile. A compound in which electron-withdrawing groups are bonded to a condensed aromatic ring having a plurality of heteroatoms, such as HAT-CN, is preferred because it is thermally stable. A [3]radialene derivative having an electron-withdrawing group (in particular, a cyano group or a halogen group such as a fluoro group) has a very high electron-accepting property and thus is preferred. Specific examples include α,α',α"-1,2,3-cyclopropanetriylidenetris [4-cyano-2,3,5,6-tetrafluorobenzeneacetonitrile], α,α',α"-1,2,3-cyclopropanetriylidenetris[2,6-dichloro-3,5-difluoro-4-(trifluoromethyl)benzeneacetonitrile], and α,α',α"-1,2,3-cyclopropanetriylidenetris[2,3,4,5,6-pentafluorobenzeneacetonitrile].

The hole-transport material with a deep HOMO level is preferably a hole-transport material having any of a carbazole skeleton, a dibenzofuran skeleton, a dibenzothiophene skeleton, and an anthracene skeleton. In particular, an aromatic amine having a substituent that includes a dibenzofuran ring or a dibenzothiophene ring, an aromatic monoamine that includes a naphthalene ring, or an aromatic monoamine in which a 9-fluorenyl group is bonded to nitrogen of amine through an arylene group may be used.

As the hole-transport material with a deep HOMO level, it is preferable to use a substance having a hole mobility higher than or equal to $1\times10^{-6}$ cm$^2$/Vs in the case where the square root of the electric field strength [V/cm] is 600. Note that other substances can also be used as long as the substances have a hole-transport property higher than an electron-transport property. Note that the substances preferably have an N,N-bis(4-biphenyl)amino group because a light-emitting device having a long lifetime can be fabricated.

Specific examples of the hole-transport material with a deep HOMO level include N-(4-biphenyl)-6,N-diphenylbenzo[b]naphtho[1,2-d]furan-8-amine (abbreviation: BnfABP), N,N-bis(4-biphenyl)-6-phenylbenzo[b]naphtho[1,2-d]furan-8-amine (abbreviation: BBABnf), 4,4'-bis(6-phenylbenzo[b]naphtho[1,2-d]furan-8-yl)-4"-phenyltriphenylamine (abbreviation: BnfBB1BP), N,N-bis(4-biphenyl)benzo[b]naphtho[1,2-d]furan-6-amine (abbreviation: BBABnf(6)), N,N-bis(4-biphenyl)benzo[b]naphtho[1,2-d]furan-8-amine (abbreviation: BBABnf(8)), N,N-bis(4-biphenyl)benzo[b]naphtho[2,3-d]furan-4-amine (abbreviation: BBABnf(II)(4)), N,N-bis[4-(dibenzofuran-4-yl)phenyl]-4-amino-p-terphenyl (abbreviation: DBfBB1TP), N-[4-(dibenzothiophen-4-yl)phenyl]-N-phenyl-4-biphenylamine (abbreviation: ThBA1BP), 4-(2-naphthyl)-4',4"-diphenyltriphenylamine (abbreviation: BBAβNB), 4-[4-(2-naphthyl)phenyl]-4',4"-diphenyltriphenylamine (abbreviation: BBAβNBi), 4,4'-diphenyl-4"-(6; 1'-binaphthyl-2-yl)triphenylamine (abbreviation: BBAαNβNB), 4,4'-diphenyl-4"-(7;1'-binaphthyl-2-yl)triphenylamine (abbreviation: BBAαNβNB-03), 4,4'-diphenyl-4"-(7-phenyl)naphthyl-2-yltriphenylamine (abbreviation: BBAPβNB-03), 4,4'-diphenyl-4"-(6;2-binaphthyl-2-yl)triphenylamine (abbreviation: BBA(βN2)B), 4,4'-diphenyl-4"-(7;2'-binaphthyl-2-yl)triphenylamine (abbreviation: BBA(βN2)B-03), 4,4'-diphenyl-4"-(4;2'-binaphthyl-1-yl)triphenylamine (abbreviation: BBAβNαNB), 4,4'-diphenyl-4"-(5;2'-binaphthyl-1-yl)triphenylamine (abbreviation: BBAβNαNB-02), 4-(4-biphenylyl)-4'-(2-naphthyl)-4"-phenyltriphenylamine (abbreviation: TPBiAβNB), 4-(3-biphenylyl)-4'-[4-(2-naphthyl)phenyl]-4"-phenyltriphenylamine (abbreviation: mTPBiAlβNBi), 4-(4-biphenylyl)-4'-[4-(2-naphthyl)phenyl]-4"-phenyltriphenylamine (abbreviation: TPBiAβNBi), 4-phenyl-4'-(1-naphthyl)-triphenylamine (abbreviation: αNBA1BP), 4,4'-bis(1-naphthyl)triphenylamine (abbreviation: αNBB1BP), 4,4'-diphenyl-4"-[4'-(carbazol-9-yl)biphenyl-4-yl]triphenylamine (abbreviation: YGTBi1BP), 4'-[4-(3-phenyl-9H-carbazol-9-yl)phenyl]tris(1,1'-biphenyl-4-yl) amine (abbreviation: YGTBi1BP-02), 4-[4'-(carbazol-9-yl) biphenyl-4-yl]-4'-(2-naphthyl)-4"-phenyltriphenylamine (abbreviation: YGTBiβNB), N-[4-(9-phenyl-9H-carbazol- 3-yl)phenyl]-N-[4-(1-naphthyl)phenyl]-9,9'-spirobi[9H-fluoren]-2-amine (abbreviation: PCBNBSF), N,N-bis(4-biphenylyl)-9,9'-spirobi[9H-fluoren]-2-amine (abbreviation: BBASF), N,N-bis(1,1'-biphenyl-4-yl)-9,9'-spirobi[9H-fluoren]-4-amine (abbreviation: BBASF(4)), N-(1,1'-biphenyl-2-yl)-N-(9,9-dimethyl-9H-fluoren-2-yl)-9,9'-spirobi[9H-fluoren]-4-amine (abbreviation: oFBiSF), N-(4-biphenyl)-N-(9,9-dimethyl-9H-fluoren-2-yl)dibenzofuran-4-amine (abbreviation: FrBiF), N-[4-(1-naphthyl)phenyl]-N-[3-(6-phenyldibenzofuran-4-yl)phenyl]-1-naphthylamine (abbreviation: mPDBfBNBN), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-[4-(9-phenylfluoren-9-yl)phenyl]triphenylamine (abbreviation: BPAFLBi), 4-phenyl-4'-(9-phenyl-9H-carbazol-3-yl)triphenylamine (abbreviation: PCBA1BP), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), N-phenyl-N-[4-(9-phenyl-9H-carbazol-3-yl)phenyl]spiro-9,9'-bifluoren-2-amine (abbreviation: PCBASF), and N-(1,1'-biphenyl-4-yl)-9,9-dimethyl-N-[4-(9-phenyl-9H-carbazol-3-yl)phenyl]-9H-fluoren-2-amine (abbreviation: PCBBiF).

The hole-injection layer 111 can be formed by any of known deposition methods such as a vacuum evaporation method.

<Hole-Transport Layer>

The hole-transport layer 112 transports holes injected from the first electrode 101 through the hole-injection layer 111, to the light-emitting layer 113.

The hole-transport layer 112 can be formed using the above-described hole-transport material. The hole-transport layer 112 may have a stacked-layer structure. Note that in the case where the hole-transport layer 112 has a stacked-layer structure, a layer on the light-emitting layer side may function as an electron-blocking layer.

It is preferable that materials be selected so that the HOMO level of the hole-transport material used in the hole-transport layer 112 is deeper than that of the hole-transport material used in the hole-injection layer 111 and a difference between the HOMO levels is less than or equal to 0.2 eV. It is more preferable that the hole-transport materials are the same material, which leads to smooth hole injection.

In the case where the hole-transport layer 112 has a stacked-layer structure, the HOMO level of the hole-transport material used in the hole-transport layer formed on the light-emitting layer 113 side is preferably deeper than that of the hole-transport material used in the hole-transport layer formed on the hole-injection layer 111 side. It is preferable that the materials be selected so that a difference between the HOMO levels is less than or equal to 0.2 eV. Owing to the above-described relation between the HOMO levels of the hole-transport materials used for the hole-injection layer 111 and the hole-transport layer 112 having a stacked-layer structure, holes are injected into each layer smoothly, which prevents an increase in driving voltage and deficiency of holes in the light-emitting layer 113.

Preferably, the hole-transport materials used for the hole-injection layer 111 and the hole-transport layer 112 having a stacked-layer structure each have a hole-transport skeleton. A carbazole skeleton, a dibenzofuran skeleton, a dibenzothiophene skeleton, and an anthracene skeleton, with which the HOMO levels of the hole-transport materials do not become too shallow, are preferably used as the hole-transport skeleton. The hole-transport materials used for adjacent layers in the hole-injection layer 111 and the hole-transport layer 112 having a stacked-layer structure preferably have the same hole-transport skeleton, in which case holes can be injected smoothly. In particular, a dibenzofuran skeleton is preferably used as the hole-transport skeleton.

The hole-transport materials used for adjacent layers in the hole-injection layer 111 and the hole-transport layer 112 having a stacked-layer structure are preferably the same, in which case holes can be injected more smoothly from a layer into an adjacent layer in the cathode direction.

<Light-Emitting Layer>

In the light-emitting device of one embodiment of the present invention, the light-emitting layer 113 may have a single-layer structure or a stacked-layer structure of a plurality of light-emitting layers. In the case where a plurality of light-emitting layers are stacked, the light-emitting layers are preferably formed to have functions different from each other.

The light-emitting layer 113 includes a light-emitting substance (guest material) and a host material in which the light-emitting substance is dispersed.

As the light-emitting substance (guest material), a substance emitting fluorescence (fluorescent substance), a substance emitting phosphorescence (phosphorescent substance), a substance exhibiting thermally activated delayed fluorescence (thermally activated delayed fluorescence (TADF) material), other light-emitting substances, or the like can be used. As an organic compound (host material), various carrier-transport materials such as the TADF material can be used in addition to electron-transport materials and hole-transport materials. Specifically, one or more kinds of materials appropriately selected from the materials described in this specification or known materials can be used as the hole-transport materials, the electron-transport materials, or the like, for example.

Examples of the fluorescent substance that can be used as a guest material in the light-emitting layer 113 are as follows. Other fluorescent substances can also be used.

The examples include 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N-diphenyl-N,N-bis[4-(9-phenyl-9H-fluoren-9-yl)phenyl]pyrene-1,6-diamine (abbreviation: 1,6FLPAPrn), s(3-methylphenyl)-N,N-bis[3-(9-phenyl-9H-fluoren-9-yl)phenyl]pyrene-1,6-diamine (abbreviation: 1, 6mMemFLPAPrn), N,N-bis[4-(9H-carbazol-9-yl)phenyl]-N,N-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenyl amine (abbreviation: PCBAPA), N,N''-(2-tert-butylanthracene-9,10-diyldi-4,1-phenylene)bis[N,N,N-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenedi amine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2- anthryl)-N,N,N-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H, 5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H, 5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H, 5H-benzo[4]quinolizin-9-yl)ethenyl]-4H-pyran-4-ylidene}propanedinitrile (abbreviation: BisDCJTM), N,N'-diphenyl-N,N'-(1,6-pyrene-diyl)bis[(6-phenylbenzo[b]naphtho[1,2-d]furan)-8-amine](abbreviation:1,6BnfAPrn-03), 3,10-bis[N-(9-phenyl-9H-carbazol-2-yl)-N-phenylamino]naphtho[2,3-b;6,7-b']bisbenzofuran (abbreviation: 3,10PCA2Nbf(IV)-02), and 3,10-bis[N-(dibenzofuran-3-yl)-N-phenylamino]naphtho[2,3-b; 6,7-b'] bisbenzofuran (abbreviation: 3,10FrA2Nbf(IV)-02). Condensed aromatic diamine compounds typified by pyrenediamine compounds such as 1,6FLPAPrn, 1,6mMemFLPAPrn, and 1,6BnfAPrn-03 are particularly preferred because of their high hole-trapping properties, high emission efficiency, and high reliability.

Examples of the phosphorescent substance that can be used as a guest material in the light-emitting layer 113 are as follows.

The examples include an organometallic iridium complex having a 4H-triazole skeleton, such as tris{2-[5-(2-methylphenyl)-4-(2,6-dimethylphenyl)-4H-1,2,4-triazol-3-yl-κN2]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), and tris[4-(3-biphenyl)-5-isopropyl-3-phenyl-4H-1,2,4-triazolato]iridium(III) (abbreviation: [Ir(iPrptz-3b)$_3$]); an organometallic iridium complex having a 1H-triazole skeleton, such as tris[3-methyl-1-(2-methylphenyl)-5-phenyl-1H-1,2,4-triazolato]iridium(III) (abbreviation: [Ir(Mptzl-mp)$_3$]) and tris(1-methyl-5-phenyl-3-propyl-1H-1,2,4-triazolato)iridium(III) (abbreviation: [Ir(Prptzl-Me)$_3$]); an organometallic iridium complex having an imidazole skeleton, such as fac-tris[1-(2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]); and an organometallic iridium complex in which a phenylpyridine derivative having an electron-withdrawing group is a ligand, such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^{2'}$}iridium(III) picolinate (abbreviation: [Ir(CF$_3$ppy)$_2$(pic)]), and bis[2-(4',6'-difluorophenyl)pyridinato-N,C$^{2'}$]iridium(III) acetylacetonate (abbreviation: FIr(acac)). These compounds emit blue phosphorescence and have an emission peak at 440 nm to 520 nm.

Other examples include organometallic iridium complexes having a pyrimidine skeleton, such as tris(4-methyl-6-phenylpyrimidinato)iridium(III) (abbreviation: [Ir(mppm)$_3$]), tris(4-tert-butyl-6-phenylpyrimidinato)iridium(III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), and (acetylacetonato)bis(4,6-diphenylpyrimidinato)iridium(III) (abbreviation: [Ir(dppm)$_2$(acac)]); organometallic iridium complexes having a pyrazine skeleton, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having a pyridine skeleton, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), and bis(2-phenylquinolinato-N,C$^{2'}$)iridium(III) acetylacetonate (abbreviation: [Ir(pq)$_2$(acac)]); and a rare earth metal complex such as tris(acetylacetonato)(monophenanthroline)terbium(III) (abbreviation: [Tb(acac)$_3$(Phen)]). These are mainly compounds that emit green phosphorescence and have an emission peak at 500 nm to 600 nm. Note that organometallic iridium complexes having a pyrimidine skeleton have distinctively high reliability and emission efficiency and thus are especially preferable.

Other examples include organometallic iridium complexes having a pyrimidine skeleton, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), and bis[4,6-di(naphthalen-1-yl)pyrimidinato(dipivaloylmethanato)iridium(III) (abbreviation: [Ir(d1npm)$_2$(dpm)]); organometallic iridium complexes having a pyrazine skeleton, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), and (acetylacetonato)bis[2,3-bis(4-fluorophenyl)quinoxalinato]iridium(III) (abbreviation: [Ir(Fdpq)$_2$(acac)]); organometallic iridium complexes having a pyridine skeleton, such as tris(1-phenylisoquinolinato-N,C$^{2'}$)iridium(III) (abbreviation: [Ir(piq)$_3$]) and bis(1-phenylisoquinolinato-N,C$^{2'}$)iridium(III) acetylacetonate (abbreviation: [Ir(piq)$_2$(acac)]); platinum complexes such as 2,3,7,8,12,13,17,18-octaethyl-21H,23H-porphyrinplatinum(II) (abbreviation: [PtOEP]); and rare earth metal complexes such as tris(1,3-diphenyl-1,3-propanedionato) (monophenanthroline)europium(III) (abbreviation: [Eu(DBM)$_3$(Phen)]) and tris[1-(2-thenoyl)-3,3,3-trifluoroacetonato (monophenanthroline)europium(III) (abbreviation: [Eu(TTA)$_3$(Phen)]). These compounds emit red phosphorescence and have an emission peak at 600 nm to 700 nm. Furthermore, the organometallic iridium complexes having a pyrazine skeleton can provide red light emission with favorable chromaticity.

Besides the above-described materials, known phosphorescent substances can also be used.

Examples of the TADF material that can be used as the guest material in the light-emitting layer 113 are as follows.

Examples of the TADF material include a fullerene, a derivative thereof, an acridine, a derivative thereof, and an eosin derivative. Furthermore, a metal-containing porphyrin, such as a porphyrin containing magnesium (Mg), zinc (Zn), cadmium (Cd), tin (Sn), platinum (Pt), indium (In), or palladium (Pd), can be given. Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride complex (PtCl$_2$OEP), which are represented by the following structural formulae.

[Chemical Formulae 24]

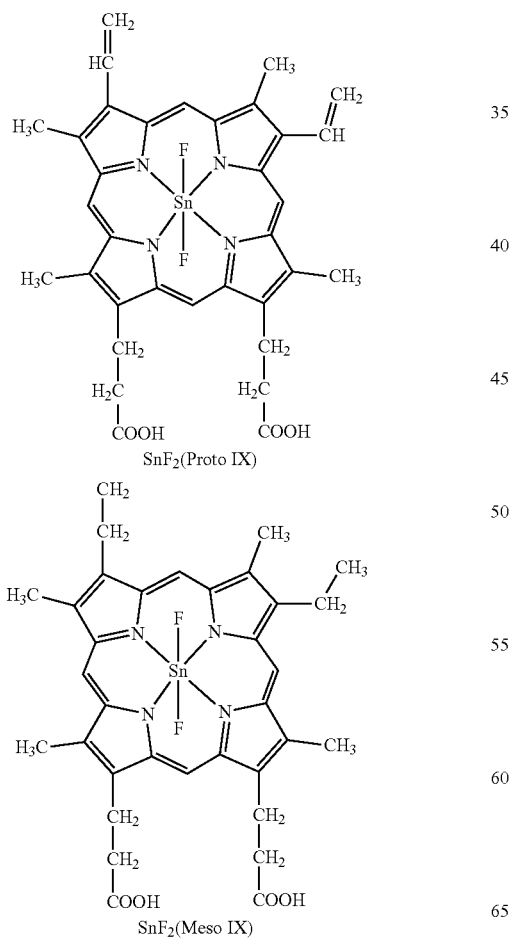

SnF$_2$(Proto IX)

SnF$_2$(Meso IX)

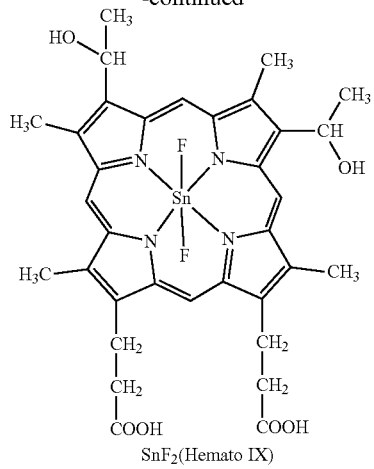

SnF$_2$(Hemato IX)

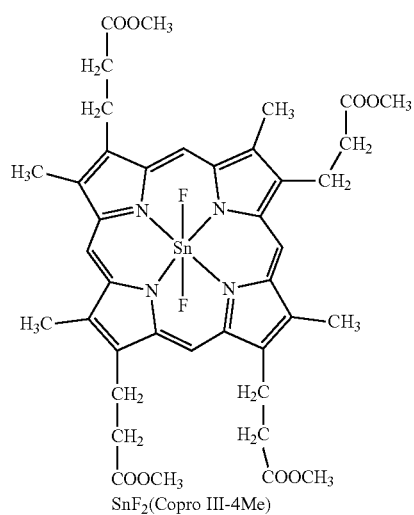

SnF$_2$(Copro III-4Me)

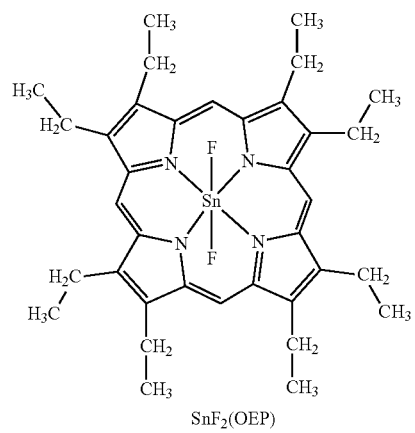

SnF$_2$(OEP)

[Chemical Formulae 25]

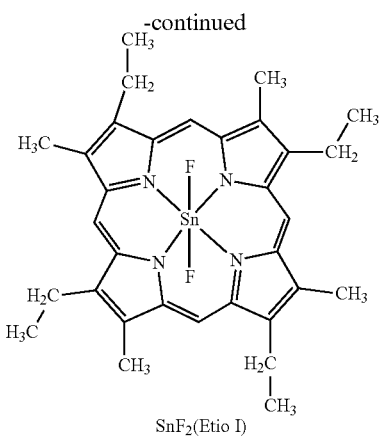

SnF₂(Etio I)

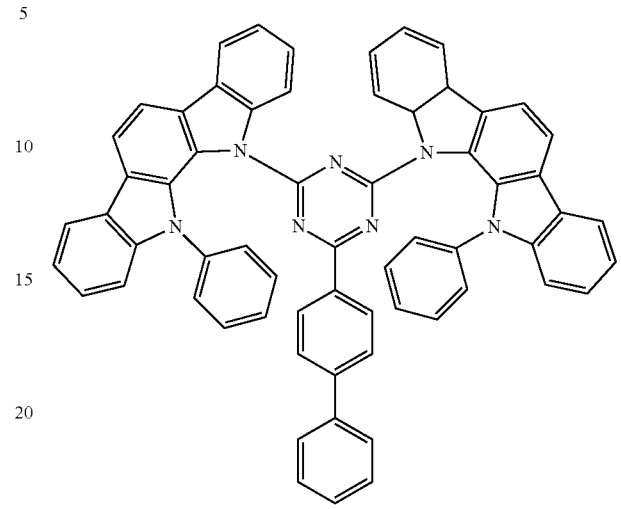

PIC-TRZ

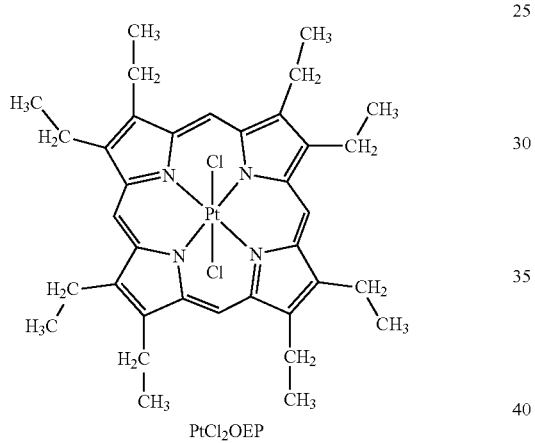

PtCl₂OEP

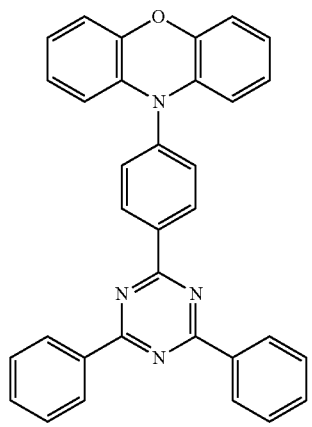

PXZ-TRZ

In addition, a heterocyclic compound having one or both of a π-electron rich heteroaromatic ring and a π-electron deficient heteroaromatic ring that is represented by the following structural formulae, such as 2-(biphenyl-4-yl)-4,6-bis(12-phenylindolo[2,3-a]carbazol-11-yl)-1,3,5-triazine (abbreviation: PIC-TRZ), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), 10-phenyl-10H,10′H-spiro[acridin-9,9′-anthracen]-10′-one (abbreviation: ACRSA), 4-(9′-phenyl-3,3′-bi-9H-carbazol-9-yl)benzofuro[3,2-d]pyrimidine (abbreviation: 4PCCzBfpm), 4-[4-(9′-phenyl-3,3′-bi-9H-carbazol-9-yl)phenyl]benzofuro[3,2-d]pyrimidine (abbreviation: 4PCCzPBfpm), or 9-[3-(4,6-diphenyl-1,3,5-triazin-2-yl)phenyl]-9′-phenyl-2,3′-bi-9H-carbazole (abbreviation: mPCCzPTzn-02) may be used.

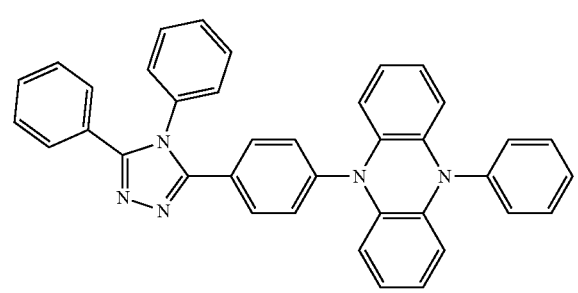

PPZ-3TPT

PCCzPTzn

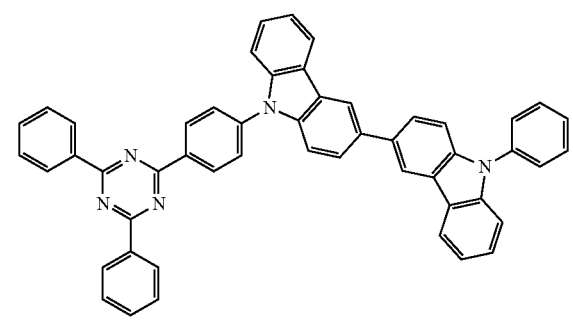

ACRSA

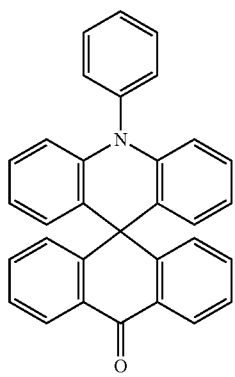

mPCCzPTzn-02

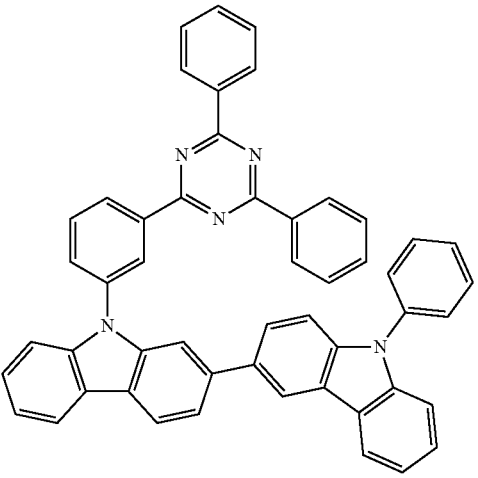

ACRXTN

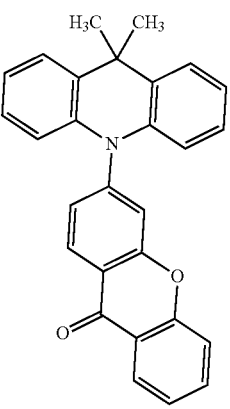

4PCCzBfpm

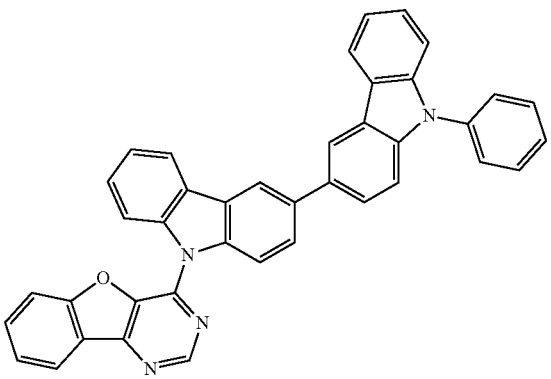

DMAC-DPS

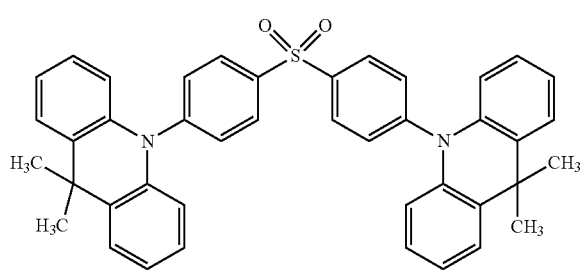

4PCCzPBfpm

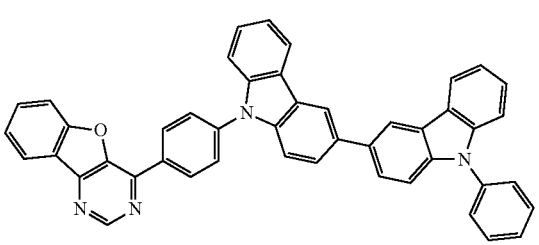

Such a heterocyclic compound is preferred because of having excellent electron-transport and hole-transport properties owing to a π-electron rich heteroaromatic ring and a π-electron deficient heteroaromatic ring. Among skeletons having the π-electron deficient heteroaromatic ring, a pyridine skeleton, a diazine skeleton (a pyrimidine skeleton, a pyrazine skeleton, and a pyridazine skeleton), and a triazine skeleton are preferred because of their high stability and reliability. In particular, a benzofuropyrimidine skeleton, a benzothienopyrimidine skeleton, a benzofuropyrazine skeleton, and a benzothienopyrazine skeleton are preferred because of their high accepting properties and reliability.

Among skeletons having the π-electron rich heteroaromatic ring, an acridine skeleton, a phenoxazine skeleton, a phenothiazine skeleton, a furan skeleton, a thiophene skeleton, and a pyrrole skeleton have high stability and reliability; therefore, at least one of these skeletons is preferably included. As a furan skeleton, a dibenzofuran skeleton is preferable. As a thiophene skeleton, a dibenzothiophene skeleton is preferable. As a pyrrole skeleton, an indole skeleton, a carbazole skeleton, an indolocarbazole skeleton, a bicarbazole skeleton, and a 3-(9-phenyl-9H-carbazol-3-yl)-9H-carbazole skeleton are particularly preferable.

Note that a substance in which the π-electron rich heteroaromatic ring is directly bonded to the π-electron deficient heteroaromatic ring is particularly preferred because the electron-donating property of the π-electron rich heteroaromatic ring and the electron-accepting property of the π-electron deficient heteroaromatic ring are both improved, the energy difference between the S1 level and the T1 level becomes small, and thus thermally activated delayed fluorescence can be obtained with high efficiency. Note that an aromatic ring to which an electron-withdrawing group such as a cyano group is bonded may be used instead of the π-electron deficient heteroaromatic ring. As a π-electron rich skeleton, an aromatic amine skeleton, a phenazine skeleton, or the like can be used. As a π-electron deficient skeleton, a xanthene skeleton, a thioxanthene dioxide skeleton, an oxadiazole skeleton, a triazole skeleton, an imidazole skeleton, an anthraquinone skeleton, a skeleton containing boron such as phenylborane or boranthrene, an aromatic ring or a heteroaromatic ring having a cyano group or a nitrile group such as benzonitrile or cyanobenzene, a carbonyl skeleton such as benzophenone, a phosphine oxide skeleton, a sulfone skeleton, or the like can be used.

As described above, a π-electron deficient skeleton and a π-electron rich skeleton can be used instead of at least one of the π-electron deficient heteroaromatic ring and the π-electron rich heteroaromatic ring.

Note that a TADF material is a material having a small difference between the Si level and the Ti level and a function of converting triplet excitation energy into singlet excitation energy by reverse intersystem crossing. Thus, a TADF material can upconvert triplet excitation energy into singlet excitation energy (i.e., reverse intersystem crossing) using a small amount of thermal energy and efficiently generate a singlet excited state. In addition, the triplet excitation energy can be converted into luminescence.

An exciplex whose excited state is formed of two kinds of substances has an extremely small difference between the S1 level and the T1 level and functions as a TADF material capable of converting triplet excitation energy into singlet excitation energy.

A phosphorescent spectrum observed at a low temperature (e.g., 77 K to 10 K) is used for an index of the T1 level. When the level of energy with a wavelength of the line obtained by extrapolating a tangent to the fluorescent spectrum at a tail on the short wavelength side is the Si level and the level of energy with a wavelength of the line obtained by extrapolating a tangent to the phosphorescent spectrum at a tail on the short wavelength side is the T1 level, the difference between the S1 level and the T1 level of the TADF material is preferably smaller than or equal to 0.3 eV, further preferably smaller than or equal to 0.2 eV.

When the TADF material is used as the guest material in the light-emitting layer 113, the S1 level and the T1 level of the host material are preferably higher than the S1 level and the T1 level of the TADF material, respectively.

As the hole-transport material that can be used as the host material in the light-emitting layer 113, it is preferable to use a substance having a hole mobility higher than or equal to $1 \times 10^{-6}$ cm$^2$/Vs in the case where the square root of the electric field strength [V/cm] is 600. Examples of the substance are shown below.

Examples of the substance include compounds having an aromatic amine skeleton such as 4,4'-bis[N-(1-naphthyl)-N-phenylamino]biphenyl (abbreviation: NPB), N,N-bis(3-methylphenyl)-N,N-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), and N-phenyl-N-[4-(9-phenyl-9H-carbazol-3-yl)phenyl]spiro-9,9'-bifluoren-2-amine (abbreviation: PCBASF); compounds having a carbazole skeleton such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), and 3,3'-bis(9-phenyl-9H-carbazole) (abbreviation: PCCP); compounds having a thiophene skeleton such as 4,4',4"-(benzene-1,3,5-triyl)tri(dibenzothiophene) (abbreviation: DB T3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having a furan skeleton such as 4,4',4"-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II). Among the above materials, the compound having an aromatic amine skeleton and the compound having a carbazole skeleton are preferred because these compounds with highly reliable and have high hole-transport properties to contribute to a reduction in driving voltage. In addition, the organic compounds given as examples of the above hole-transport material can also be used.

As the electron-transport material that can be used as the host material in the light-emitting layer 113, it is preferable to use a substance having an electron mobility higher than or equal to $1 \times 10^{-6}$ cm$^2$/Vs in the case where the square root of the electric field strength [V/cm] is 600. Examples of the substance are shown below. In addition, an electron-transport material that can be used in the electron-transport layer 114, which is described later, can also be used.

Examples of the electron-transport material include metal complexes such as bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds having a polyazole skeleton, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2"-(1,3,5-benzenetriyl)tris(1-phenyl-1H-benzimidazole) (abbreviation: TPBI), and 2-[3-(dibenzothiophen-4-yl)phenyl]-1-phenyl-1H-benzimidazole (abbreviation: mDBTBIm-II); heterocyclic compounds having a diazine skeleton, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[fh]quinoxaline (abbreviation: 2mDBTBPDBq-II), 2-[3'-(9H-carbazol-9-yl)biphenyl-3-yl]dibenzo[f, h]quinoxaline (abbreviation: 2mCzBPDB q), 4,6-bis[3-(phenanthren-9-yl)phenyl]pyrimidine (abbreviation: 4,6mPnP2Pm), and 4,6-bis[3-(4-dibenzothienyl)phenyl]pyrimidine (abbreviation: 4,6mDBTP2Pm-II); and heterocyclic compounds having a pyridine skeleton, such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Among the above materials, the heterocyclic compound having a diazine skeleton and the heterocyclic compound having a pyridine skeleton have high reliability and thus are preferable. In particular, the heterocyclic compound having a diazine (pyrimidine or pyrazine) skeleton has an excellent electron-transport property to contribute to a reduction in driving voltage.

In the case where the TADF material is used as the host material in the light-emitting layer 113, the above-described materials can also be used. When the TADF material is used as the host material, triplet excitation energy generated in the TADF material is converted into singlet excitation energy by reverse intersystem crossing and transferred to the emission center substance, whereby the emission efficiency of the light-emitting device can be increased. Here, the TADF material functions as an energy donor, and the emission center substance functions as an energy acceptor. Therefore, the use of the TADF material as the host material is very effective in the case where a fluorescent substance is used as the guest material. In that case, it is preferable that the $S_1$ level of the TADF material be higher than the $S_1$ level of the fluorescent substance in order that high emission efficiency be achieved. Furthermore, the $T_1$ level of the TADF material is preferably higher than the $S_1$ level of the fluorescent substance. Therefore, the $T_1$ level of the TADF material is preferably higher than the $T_1$ level of the fluorescent substance.

A TADF material that emits light whose wavelength overlaps with the wavelength on a lowest-energy-side absorption band of the fluorescent substance is preferably used, in which case excitation energy is transferred smoothly from the TADF material to the fluorescent substance and light emission can be obtained efficiently.

In addition, in order to efficiently generate singlet excitation energy from the triplet excitation energy by reverse intersystem crossing, carrier recombination preferably occurs in the TADF material. It is also preferable that the triplet excitation energy generated in the TADF material not be transferred to the triplet excitation energy of the fluorescent substance. For that reason, the fluorescent substance preferably has a protective group around a luminophore (a skeleton which causes light emission) of the fluorescent substance. As the protective group, a substituent having no 7C bond and a saturated hydrocarbon are preferably used. Specific examples include an alkyl group having 3 to 10 carbon atoms, a substituted or unsubstituted cycloalkyl group having 3 to 10 carbon atoms, and a trialkylsilyl group having 3 to 10 carbon atoms. It is further preferable that the fluorescent substance have a plurality of protective groups. The substituents having no 7C bond are poor in carrier transport performance, whereby the TADF material and the luminophore of the fluorescent substance can be made away from each other with little influence on carrier transportation or carrier recombination. Here, the luminophore refers to an atomic group (skeleton) that causes light emission in a fluorescent substance. The luminophore is preferably a skeleton having a π bond, further preferably includes an aromatic ring, and still further preferably includes a condensed aromatic ring or a condensed heteroaromatic ring. Examples of the condensed aromatic ring or the condensed heteroaromatic ring include a phenanthrene skeleton, a stilbene skeleton, an acridone skeleton, a phenoxazine skeleton, and a phenothiazine skeleton. Specifically, a fluorescent substance having any of a naphthalene skeleton, an anthracene skeleton, a fluorene skeleton, a chrysene skeleton, a triphenylene skeleton, a tetracene skeleton, a pyrene skeleton, a perylene skeleton, a coumarin skeleton, a quinacridone skeleton, and a naphthobisbenzofuran skeleton is preferred because of its high fluorescence quantum yield.

In the case where a fluorescent substance is used as the guest material in the light-emitting layer 113, a material having an anthracene skeleton is favorably used as the host material. The use of a substance having an anthracene skeleton makes it possible to obtain a light-emitting layer with high emission efficiency and high durability. Among the substances having an anthracene skeleton, a substance having a diphenylanthracene skeleton, in particular, a substance having a 9,10-diphenylanthracene skeleton, is chemically stable and thus is preferable.

The host material preferably has a carbazole skeleton because the hole-injection and hole-transport properties are improved; further preferably, the host material has a benzocarbazole skeleton in which a benzene ring is further condensed to carbazole because the HOMO level thereof is shallower than that of carbazole by approximately 0.1 eV and thus holes enter the host material easily. In particular, the host material preferably has a dibenzocarbazole skeleton because the HOMO level thereof is shallower than that of carbazole by approximately 0.1 eV so that holes enter the host material easily, the hole-transport property is improved, and the heat resistance is increased.

Thus, a substance having both of a 9,10-diphenylanthracene skeleton, which is an anthracene skeleton, and a carbazole skeleton (or a benzocarbazole skeleton or a dibenzocarbazole skeleton) is further preferable as the host material. Note that in terms of an improvement in the hole-injection and hole-transport properties described above, instead of a carbazole skeleton, a benzofluorene skeleton or a dibenzo fluorene skeleton may be used. Examples of such a substance include 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), 9-phenyl-10-{4-(9-phenyl-9H-fluoren-9-yl)biphenyl-4'-yl}anthracene (abbreviation: FLPPA), and 9-(1-naphthyl)-10-[4-(2-naphthyl)phenyl]anthracene (abbreviation: αN-βNPAnth). Note that CzPA, cgDBCzPA, 2mBnfPPA, and PCzPA have excellent characteristics and thus are preferable.

Note that the host material may be a mixture of a plurality of kinds of substances; in the case of using a mixed host material, it is preferable to mix an electron-transport material with a hole-transport material. By mixing the electron-transport material with the hole-transport material, the transport property of the light-emitting layer 113 can be easily adjusted and a recombination region can be easily controlled. The weight ratio of the content of the hole-transport material to the content of the electron-transport material may be 1:19 to 19:1.

Note that a phosphorescent substance can be used as part of the host material in the case where the host material is formed by mixing a plurality of kinds of substances as described above. When a fluorescent substance is used as the emission center substance, a phosphorescent substance can be used as an energy donor for supplying excitation energy to the fluorescent substance.

An exciplex may be formed of these mixed materials. When these mixed materials are selected so as to form an exciplex that exhibits light emission whose wavelength overlaps with the wavelength on a lowest-energy-side absorption band of the light-emitting substance, energy can be transferred smoothly and light emission can be obtained efficiently. The use of such a structure is preferred because the driving voltage can be reduced.

Note that at least one of the materials forming an exciplex may be a phosphorescent substance. In this case, triplet excitation energy can be efficiently converted into singlet excitation energy by reverse intersystem crossing.

Combination of an electron-transport material and a hole-transport material whose HOMO level is higher than or equal to that of the electron-transport material is preferable for forming an exciplex. In addition, the LUMO level of the hole-transport material is preferably higher than or equal to that of the electron-transport material. Note that the LUMO levels and the HOMO levels of the materials can be derived from the electrochemical characteristics (the reduction potentials and the oxidation potentials) of the materials that are measured by cyclic voltammetry (CV).

The formation of an exciplex can be confirmed by a phenomenon in which the emission spectrum of the mixed film in which the hole-transport material and the electron-transport material are mixed is shifted to the longer wavelength side than the emission spectra of each of the materials (or has another peak on the longer wavelength side) observed by comparison of the emission spectra of the hole-transport material, the electron-transport material, and the mixed film of these materials, for example. Alternatively, the formation of an exciplex can be confirmed by a difference in transient response, such as a phenomenon in which the transient PL lifetime of the mixed film has more long lifetime components or has a larger proportion of delayed components than that of each of the materials, observed by comparison of transient photoluminescence (PL) of the hole-transport material, the electron-transport material, and the mixed film of the materials. The transient PL can be rephrased as transient electroluminescence (EL). That is, the formation of an exciplex can also be confirmed by a difference in transient response observed by comparison of the transient EL of the hole-transport material, the electron-transport material, and the mixed film of the materials.

<Electron-Transport Layer>

The electron-transport layer 114 transfers electrons injected from the second electrode 102 to the light-emitting layer 113 and is in contact with the light-emitting layer 113. Note that the electron-transport layer 114 includes an electron-transport material with a HOMO level higher than or equal to −6.0 eV and an organometallic complex of an alkali metal or an alkaline earth metal. The electron mobility of the electron-transport material with a HOMO level higher than or equal to −6.0 eV is preferably higher than or equal to $1\times10^{-7}$ cm$^2$/Vs and lower than or equal to $1\times10^{-5}$ cm$^2$, further preferably higher than or equal to $1\times10^{-7}$ cm$^2$/Vs and lower than or equal to $5\times10^{-5}$ cm$^2$ in the case where the square root of the electric field strength [V/cm] is 600.

Note that the electron-transport material with a HOMO level higher than or equal to −6.0 eV preferably has an anthracene skeleton, further preferably has an anthracene skeleton and a heterocyclic skeleton. Therefore, the quinoxaline derivative of one embodiment of the present invention is preferably used as the electron-transport material. In addition, some of the above-described electron-transport materials that can be used as the host material, or the above-described materials given as materials that can be used as the host material in combination with the above-described fluorescent substance can be used in the electron-transport layer 114.

The organic metal complex of an alkali metal or an alkaline earth metal is preferably an organic complex of lithium, and particularly preferably 8-hydroxyquinolinato-lithium (abbreviation: Liq).

Furthermore, the electron mobility of the electron-transport material with a HOMO level higher than or equal to −6.0 eV that is used for the electron-transport layer 114 in the case where the square root of the electric field strength [V/cm] is 600 is preferably lower than the electron mobility of the host material in the light-emitting layer 113. The amount of electrons injected into the light-emitting layer can be controlled by the reduction in the electron-transport property of the electron-transport layer, whereby the light-emitting layer can be prevented from having excess electrons.

<Electron-Injection Layer>

The electron-injection layer 115 is a layer for increasing the efficiency of electron injection from the second electrode 102 and is preferably formed using a material whose value of the LUMO level has a small difference (0.5 eV or less) from the work function of a material of the second electrode 102. Thus, the electron-injection layer 115 can be formed using an alkali metal, an alkaline earth metal, or a compound thereof, such as lithium, cesium, lithium fluoride (LiF), cesium fluoride (CsF), calcium fluoride (CaF$_2$), 8-hydroxyquinolinatolithium (abbreviation: Liq), 2-(2-pyridyl)phenolatolithium (abbreviation: LiPP), 2-(2-pyridyl)-3-pyridinolato lithium (abbreviation: LiPPy), 4-phenyl-2-(2-pyridyl) phenolato lithium (abbreviation: LiPPP), lithium oxide (LiO$_x$), or cesium carbonate. A rare earth metal compound like erbium fluoride (ErF3) can also be used.

Figure 1B:
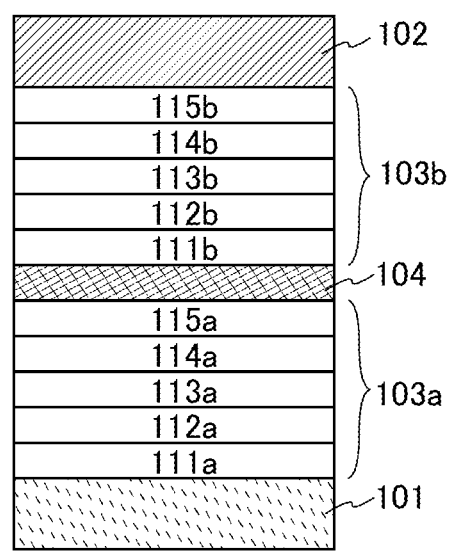

When a charge-generation layer 104 is provided between two EL layers 103a and 103b as in the light-emitting device in FIG. 1B, a structure in which a plurality of EL layers are stacked between the pair of electrodes (the structure is also referred to as a tandem structure) can be obtained. Note that in this embodiment, functions and materials of the hole-injection layer 111, the hole-transport layer 112, the light-emitting layer 113, the electron-transport layer 114, and the electron-injection layer 115 that are illustrated in FIG. 1A are the same as those of hole-injection layers 111a and 111b, hole-transport layers 112a and 112b, light-emitting layers 113a and 113b, electron-transport layers 114a and 114b, and electron-injection layers 115a and 115b that are illustrated in FIG. 1B.

<Charge-Generation Layer>

In the light-emitting device in FIG. 1B, the charge-generation layer 104 has a function of injecting electrons into the EL layer 103a on the first electrode 101 (anode) side and injecting holes into the EL layer 103b on the second electrode 102 (cathode) side when a voltage is applied between the first electrode (anode) 101 and the second electrode (cathode) 102. The charge-generation layer 104 may be either a p-type layer in which an electron acceptor (acceptor) is added to a hole-transport material or an n-type layer in which an electron donor (donor) is added to an electron-transport material. Alternatively, both of these layers may be stacked. Alternatively, the p-type layer and any one or both of an electron-relay layer and an electron-injection buffer layer, which are described later, may be combined. Note that forming the charge-generation layer 104 with the use of any of the above materials can inhibit an increase in driving voltage caused by the stack of the EL layers.

In the case where the charge-generation layer 104 is a p-type layer in which an electron acceptor is added to a hole-transport material, any of the materials described in this embodiment can be used as the hole-transport material. As the electron acceptor, it is possible to use 7,7,8,8-tetracyano-2,3,5,6-tetrafluoroquinodimethane (abbreviation: F4-TCNQ), chloranil, and the like. Other examples include oxides of metals that belong to Group 4 to Group 8 of the periodic table. Specific examples are vanadium oxide, niobium oxide, tantalum oxide, chromium oxide, molybdenum oxide, tungsten oxide, manganese oxide, and rhenium oxide.

In the case where the charge-generation layer 104 is an n-type layer in which an electron donor is added to an electron-transport material, any of the materials described in this embodiment can be used as the electron-transport material. As the electron donor, it is possible to use an alkali metal, an alkaline earth metal, a rare earth metal, metals that belong to Group 2 and Group 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. An organic compound such as tetrathianaphthacene may be used as the electron donor.

When the electron-relay layer which is preferably combined with the p-type layer as described above is provided between the electron-injection buffer layer and the p-type layer, the electron-relay layer has a function of preventing an interaction between the electron-injection buffer layer and the p-type layer and smoothly transferring electrons. The electron-relay layer includes at least an electron-transport material, and the LUMO level of the electron-transport material is preferably between the LUMO level of the electron-accepting substance in the p-type layer and the LUMO level of a substance in the electron-injection buffer layer. As a specific value of the energy level, the LUMO level of the electron-transport material in the electron-relay layer is preferably higher than or equal to $-5.0$ eV, more preferably higher than or equal to $-5.0$ eV and lower than or equal to $-3.0$ eV. Note that as the electron-transport material in the electron-relay layer, a phthalocyanine-based material or a metal complex having a metal-oxygen bond and an aromatic ligand is preferably used.

A substance having an excellent electron-injection property can be used for the electron-injection buffer layer. For example, an alkali metal, an alkaline earth metal, a rare earth metal, or a compound thereof (an alkali metal compound (including an oxide such as lithium oxide, a halide, and a carbonate such as lithium carbonate and cesium carbonate), an alkaline earth metal compound (including an oxide, a halide, and a carbonate), or a rare earth metal compound (including an oxide, a halide, and a carbonate)) can be used.

In the case where the electron-injection buffer layer includes the electron-transport material and an electron-donating substance, an organic compound such as tetrathianaphthacene (abbreviation: TTN), nickelocene, or decamethylnickelocene can be used as the electron-donating substance, as well as an alkali metal, an alkaline earth metal, a rare earth metal, a compound thereof (an alkali metal compound (including an oxide such as lithium oxide, a halide, and a carbonate such as lithium carbonate and cesium carbonate), an alkaline earth metal compound (including an oxide, a halide, and a carbonate), or a rare earth metal compound (including an oxide, a halide, and a carbonate)). As the electron-transport material, a material similar to the above-described material for the electron-transport layer can be used.

Although FIG. 1B illustrates the structure in which two EL layers 103 are stacked, three or more EL layers may be stacked with charge-generation layers each provided between two adjacent EL layers.

The above-described charge-generation layer can be used instead of the above-described electron-injection layer. In that case, the electron-injection buffer layer, the electron-relay layer, and the p-type layer are preferably stacked in this order from the anode side.

<Substrate>

The light-emitting device described in this embodiment can be formed over any of a variety of substrates. Note that the type of substrate is not limited to a certain type. Examples of the substrate include semiconductor substrates (e.g., a single crystal substrate and a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, and a base material film.

Examples of the glass substrate include a barium borosilicate glass substrate, an aluminoborosilicate glass substrate, and a soda lime glass substrate. Examples of the flexible substrate, the attachment film, and the base material film include plastics typified by polyethylene terephthalate (PET), polyethylene naphthalate (PEN), and polyether sulfone (PES); a synthetic resin such as an acrylic resin; polypropylene; polyester; polyvinyl fluoride; polyvinyl chloride; polyamide; polyimide; an aramid resin; an epoxy resin; an inorganic vapor deposition film; and paper.

For fabrication of the light-emitting device in this embodiment, a vacuum process such as an evaporation method or a solution process such as a spin coating method or an ink-jet method can be used. When an evaporation method is used, a physical vapor deposition method (PVD method) such as a sputtering method, an ion plating method, an ion beam evaporation method, a molecular beam evaporation method, or a vacuum evaporation method, a chemical vapor deposition method (CVD method), or the like can be used. Specifically, the functional layers included in the EL layers (the hole-injection layers 111, 111a, and 111b, the hole-transport layers 112, 112a, and 112b, the light-emitting layers 113, 113a, 113b, and 113c, the electron-transport layers 114, 114a, and 114b, and the electron-injection layers 115, 115a, and 115b) and the charge-generation layers 104, 104a, and 104b of the light-emitting device can be formed by an evaporation method (e.g., a vacuum evaporation method), a coating method (e.g., a dip coating method, a die coating method, a bar coating method, a spin coating method, or a spray coating method), a printing method (e.g., an ink-jet method, screen printing (stencil), offset printing (planography), flexography (relief printing), gravure printing, micro-contact printing, or nanoimprint lithography), or the like.

Note that materials that can be used for the functional layers included in the EL layers 103, 103a, and 103b (the hole-injection layers 111, 111a, and 111b, the hole-transport layers 112, 112a, and 112b, the light-emitting layers 113, 113a, 113b, and 113c, the electron-transport layers 114, 114a, and 114b, and the electron-injection layers 115, 115a, and 115b) and the charge-generation layers 104, 104a, and 104b of the light-emitting device described in this embodiment are not limited to the above materials, and other materials can be used in combination as long as the functions of the layers are fulfilled. For example, a high-molecular compound (e.g., an oligomer, a dendrimer, and a polymer), a middle molecular compound (a compound between a low molecular compound and a high-molecular compound with a molecular weight of 400 to 4000), or an inorganic compound (e.g., a quantum dot material) can be used. The quantum dot material may be a colloidal quantum dot material, an alloyed quantum dot material, a core-shell quantum dot material, a core quantum dot material, or the like.

The light-emitting device that is used in the light-emitting apparatus of one embodiment of the present invention having the above-described structure can have a long lifetime.

The structures described in this embodiment can be used in combination with any of the structures described in the other embodiments, as appropriate.

Embodiment 3

Figure 2A:
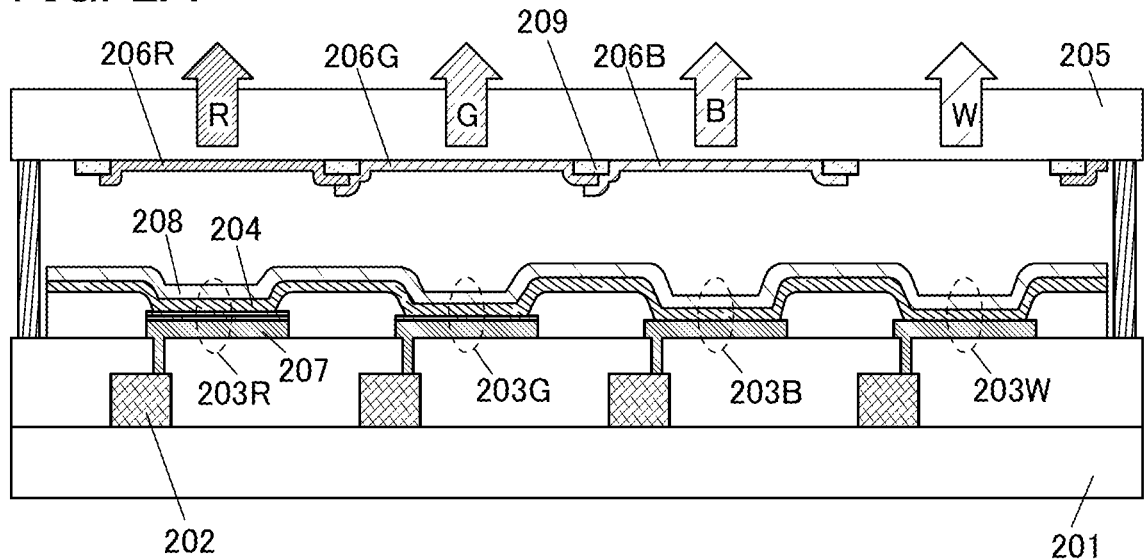
FIGS. 2A to 2C illustrate light-emitting apparatus.

In this embodiment, a light-emitting apparatus of one embodiment of the present invention will be described. Note that a light-emitting apparatus illustrated in FIG. 2A is an active-matrix light-emitting apparatus in which transistors (FETs) 202 over a first substrate 201 are electrically connected to light-emitting devices (203R, 203G, 203B, and 203W). The light-emitting devices (203R, 203G, 203B, and 203W) include a common EL layer 204 and each have a microcavity structure in which the optical path length between electrodes is adjusted according to the emission color of the light-emitting device. The light-emitting apparatus is a top-emission light-emitting apparatus in which light is emitted from the EL layer 204 through color filters (206R, 206G, and 206B) formed on a second substrate 205.

The light-emitting apparatus illustrated in FIG. 2A is fabricated such that a first electrode 207 functions as a reflective electrode and a second electrode 208 functions as a transflective electrode that both transmits and reflects light (visible light or near-infrared light). Note that description in any of the other embodiments can be referred to as appropriate for electrode materials for the first electrode 207 and the second electrode 208.

Figure 2B:
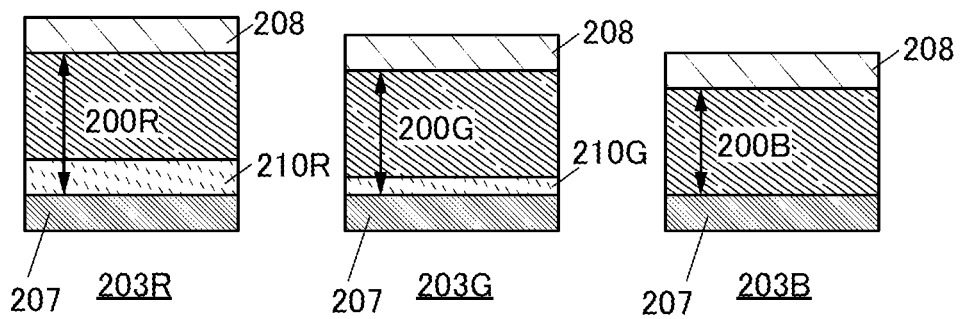

In the case where the light-emitting device 203R functions as a red light-emitting device, the light-emitting device 203G functions as a green light-emitting device, the light-emitting device 203B functions as a blue light-emitting device, and the light-emitting device 203W functions as a white light-emitting device in FIG. 2A, for example, a gap between the first electrode 207 and the second electrode 208 in the light-emitting device 203R is adjusted to have an optical path length 200R, a gap between the first electrode 207 and the second electrode 208 in the light-emitting device 203G is adjusted to have an optical path length 200G, and a gap between the first electrode 207 and the second electrode 208 in the light-emitting device 203B is adjusted to have an optical path length 200B as illustrated in FIG. 2B. Note that optical adjustment can be performed in such a manner that a conductive layer 210R is stacked over the first electrode 207 in the light-emitting device 203R and a conductive layer 210G is stacked over the first electrode 207 in the light-emitting device 203G as illustrated in FIG. 2B.

The second substrate 205 is provided with the color filters (206R, 206G, and 206B). Note that the color filters each transmit visible light in a specific wavelength range and blocks visible light in a specific wavelength range. Thus, as illustrated in FIG. 2A, the color filter 206R that transmits only light in the red wavelength range is provided in a position overlapping with the light-emitting device 203R, whereby red light emission can be obtained from the light-emitting device 203R. Furthermore, the color filter 206G that transmits only light in the green wavelength range is provided in a position overlapping with the light-emitting device 203G, whereby green light emission can be obtained from the light-emitting device 203G. Moreover, the color filter 206B that transmits only light in the blue wavelength range is provided in a position overlapping with the light-emitting device 203B, whereby blue light emission can be obtained from the light-emitting device 203B. Note that the light-emitting device 203W can emit white light without a color filter. Note that a black layer (black matrix) 209 may be provided at an end portion of each color filter. The color filters (206R, 206G, and 206B) and the black layer 209 may be covered with an overcoat layer formed using a transparent material.

Figure 2C:
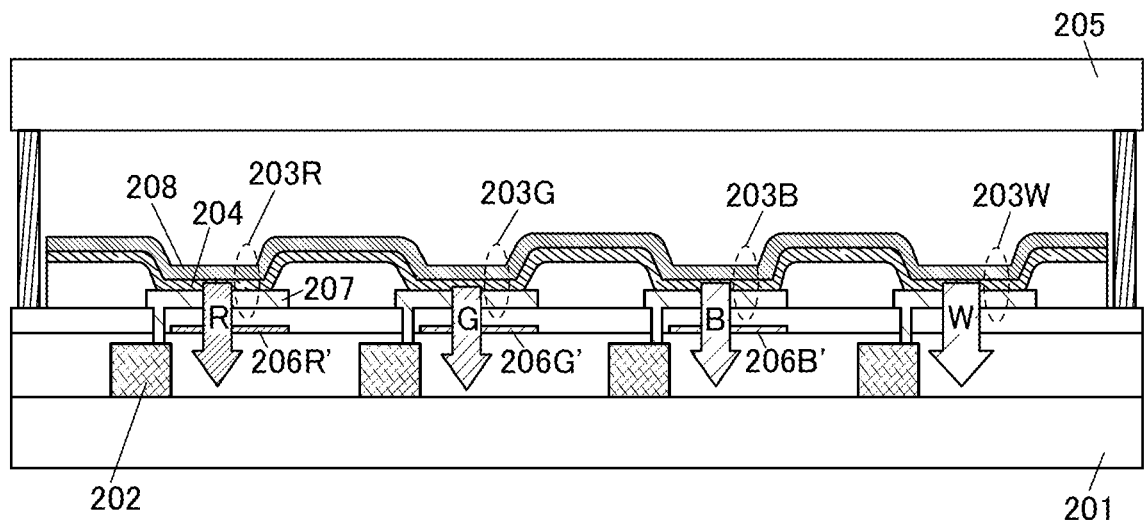

Although the light-emitting apparatus in FIG. 2A has a structure in which light is extracted from the second substrate 205 side (top emission structure), a structure in which light is extracted from the first substrate 201 side where the FETs 202 are formed (bottom emission structure) may be employed as illustrated in FIG. 2C. In the case of a bottom-emission light-emitting apparatus, the first electrode 207 is formed as a transflective electrode and the second electrode 208 is formed as a reflective electrode. As the first substrate 201, a substrate having at least a light-transmitting property is used. As illustrated in FIG. 2C, color filters (206R', 206G', and 206B') are provided closer to the first substrate 201 than the light-emitting devices (203R, 203G, and 203B) are.

In FIG. 2A, the light-emitting devices are the red light-emitting device, the green light-emitting device, the blue light-emitting device, and the white light-emitting device; however, the light-emitting devices of one embodiment of the present invention are not limited to the above, and a yellow light-emitting device or an orange light-emitting device may be used. Note that description in any of the other embodiments can be referred to as appropriate for materials that are used for the EL layers (a light-emitting layer, a hole-injection layer, a hole-transport layer, an electron-transport layer, an electron-injection layer, a charge-generation layer, and the like) to fabricate each of the light-emitting devices. In that case, a color filter needs to be appropriately selected according to the emission color of the light-emitting device.

With the above structure, a light-emitting apparatus including light-emitting devices that exhibit a plurality of emission colors can be fabricated.

The structures described in this embodiment can be used in combination with any of the structures described in the other embodiments, as appropriate.

Embodiment 4

In this embodiment, a light-emitting apparatus of one embodiment of the present invention will be described.

The use of the light-emitting device of one embodiment of the present invention allows fabrication of an active-matrix light-emitting apparatus or a passive-matrix light-emitting apparatus. Note that an active-matrix light-emitting apparatus has a structure including a combination of a light-emitting device and a transistor (FET). Thus, each of a passive-matrix light-emitting apparatus and an active-matrix light-emitting apparatus is one embodiment of the present invention. Note that any of the light-emitting devices described in other embodiments can be used in the light-emitting apparatus described in this embodiment.

In this embodiment, an active-matrix light-emitting apparatus will be described with reference to FIGS. 3A and 3B.

Figure 3A:
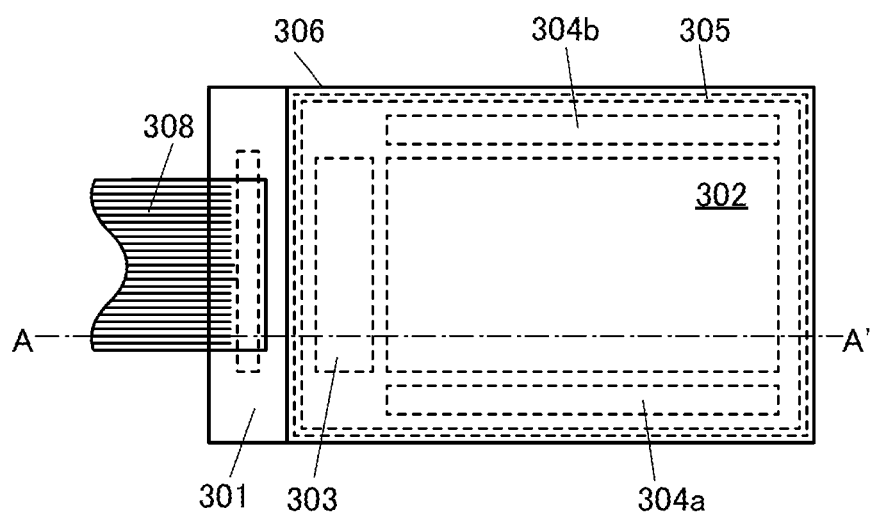
FIG. 3A is a top view illustrating a light-emitting apparatus and FIG. 3B is a cross-sectional view illustrating the light-emitting apparatus.
Figure 3B:
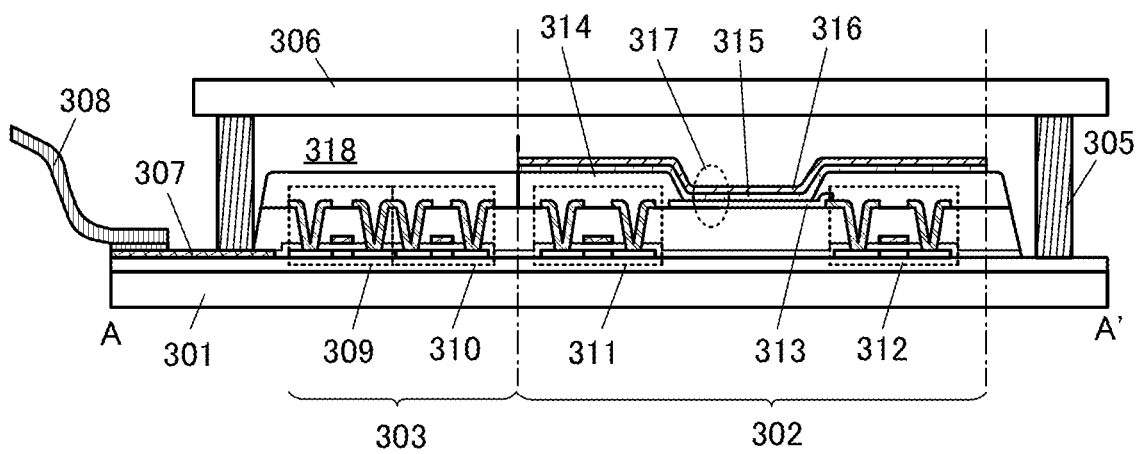

FIG. 3A is a top view illustrating the light-emitting apparatus, and FIG. 3B is a cross-sectional view taken along chain line A-A' in FIG. 3A. The active-matrix light-emitting apparatus includes a pixel portion 302, a driver circuit portion (source line driver circuit) 303, and driver circuit portions (gate line driver circuits) (304*a* and 304*b*) that are provided over a first substrate 301. The pixel portion 302 and the driver circuit portions (303, 304*a*, and 304*b*) are sealed between the first substrate 301 and a second substrate 306 with a sealant 305.

A lead wiring 307 is provided over the first substrate 301. The lead wiring 307 is electrically connected to an FPC 308 that is an external input terminal. Note that the FPC 308 transmits a signal (e.g., a video signal, a clock signal, a start signal, or a reset signal) or a potential from the outside to the driver circuit portions (303, 304*a*, and 304*b*). The FPC 308 may be provided with a printed wiring board (PWB). Note that the light-emitting apparatus provided with an FPC or a PWB is included in the category of a light-emitting apparatus.

FIG. 3B illustrates a cross-sectional structure of the light-emitting apparatus.

The pixel portion 302 includes a plurality of pixels each of which includes an FET (switching FET) 311, an FET (current control FET) 312, and a first electrode 313 electrically connected to the FET 312. Note that the number of FETs included in each pixel is not particularly limited and can be set appropriately.

As FETs 309, 310, 311, and 312, for example, a staggered transistor or an inverted staggered transistor can be used without particular limitation. A top-gate transistor, a bottom-gate transistor, or the like may be used.

Note that there is no particular limitation on the crystallinity of a semiconductor that can be used for the FETs 309, 310, 311, and 312, and an amorphous semiconductor or a semiconductor having crystallinity (a microcrystalline semiconductor, a polycrystalline semiconductor, a single crystal semiconductor, or a semiconductor partly including crystal regions) may be used. A semiconductor having crystallinity is preferably used, in which case deterioration of the transistor characteristics can be inhibited.

For the semiconductor, a Group 14 element, a compound semiconductor, an oxide semiconductor, an organic semiconductor, or the like can be used, for example. As a typical example, a semiconductor containing silicon, a semiconductor containing gallium arsenide, or an oxide semiconductor containing indium can be used.

The driver circuit portion 303 includes the FET 309 and the FET 310. The driver circuit portion 303 may be formed with a circuit including transistors having the same conductivity type (either n-channel transistors or p-channel transistors) or a CMOS circuit including an n-channel transistor and a p-channel transistor. Furthermore, a driver circuit may be provided outside.

An end portion of the first electrode 313 is covered with an insulator 314. The insulator 314 can be formed using an organic compound such as a negative photosensitive resin or a positive photosensitive resin (acrylic resin), or an inorganic compound such as silicon oxide, silicon oxynitride, or silicon nitride. The insulator 314 preferably has a curved surface with curvature at an upper end portion or a lower end portion thereof. In that case, favorable coverage with a film formed over the insulator 314 can be obtained.

An EL layer 315 and a second electrode 316 are stacked over the first electrode 313. The EL layer 315 includes a light-emitting layer, a hole-injection layer, a hole-transport layer, an electron-transport layer, an electron-injection layer, a charge-generation layer, and the like.

The structure and materials described in any of the other embodiments can be used for the components of a light-emitting device 317 described in this embodiment. Although not illustrated, the second electrode 316 is electrically connected to the FPC 308 that is an external input terminal.

Although the cross-sectional view in FIG. 3B illustrates only one light-emitting device 317, a plurality of light-emitting devices are arranged in a matrix in the pixel portion 302. Light-emitting devices that emit light of three kinds of colors (R, G, and B) are selectively formed in the pixel portion 302, whereby a light-emitting apparatus capable of displaying a full-color image can be obtained. In addition to the light-emitting devices that emit light of three kinds of colors (R, G, and B), for example, light-emitting devices that emit light of white (W), yellow (Y), magenta (M), cyan (C), and the like may be formed. For example, the light-emitting devices that emit light of some of the above colors are used in combination with the light-emitting devices that emit light of three kinds of colors (R, G, and B), whereby effects such as an improvement in color purity and a reduction in power consumption can be achieved. Alternatively, a light-emitting apparatus which is capable of displaying a full-color image may be fabricated by a combination with color filters. As color filters, red (R), green (G), blue (B), cyan (C), magenta (M), and yellow (Y) color filters and the like can be used.

When the second substrate 306 and the first substrate 301 are bonded to each other with the sealant 305, the FETs (309, 310, 311, and 312) and the light-emitting device 317 over the first substrate 301 are provided in a space 318 surrounded by the first substrate 301, the second substrate 306, and the sealant 305. Note that the space 318 may be filled with an inert gas (e.g., nitrogen or argon) or an organic substance (including the sealant 305).

An epoxy resin, glass frit, or the like can be used for the sealant 305. It is preferable to use a material that is permeable to as little moisture and oxygen as possible for the sealant 305. As the second substrate 306, a substrate that can be used as the first substrate 301 can be similarly used. Thus, any of the various substrates described in the other embodiments can be appropriately used. As the substrate, a glass substrate, a quartz substrate, or a plastic substrate made of fiber-reinforced plastic (FRP), polyvinyl fluoride (PVF), polyester, an acrylic resin, or the like can be used. In the case where glass frit is used for the sealant, the first substrate 301 and the second substrate 306 are preferably glass substrates in terms of adhesion.

Accordingly, the active-matrix light-emitting apparatus can be obtained.

In the case where the active-matrix light-emitting apparatus is provided over a flexible substrate, the FETs and the light-emitting device may be directly formed over the flexible substrate; alternatively, the FETs and the light-emitting device may be formed over a substrate provided with a separation layer and then separated at the separation layer by application of heat, force, laser, or the like to be transferred to a flexible substrate. For the separation layer, a stack including inorganic films such as a tungsten film and a silicon oxide film, or an organic resin film of polyimide or the like can be used, for example. Examples of the flexible substrate include, in addition to a substrate over which a transistor can be formed, a paper substrate, a cellophane substrate, an aramid film substrate, a polyimide film substrate, a cloth substrate (including a natural fiber (silk, cotton, or hemp), a synthetic fiber (nylon, polyurethane, or polyester), a regenerated fiber (acetate, cupro, rayon, or regenerated polyester), or the like), a leather substrate, and a rubber substrate. With the use of any of these substrates, an increase in durability, an increase in heat resistance, a reduction in weight, and a reduction in thickness can be achieved.

The light-emitting device included in the active-matrix light-emitting apparatus may emit pulsed light (with a frequency of kHz or MHz, for example) so that the light is used for display. The light-emitting device formed using any of the above organic compounds has excellent frequency characteristics; therefore, time for driving the light-emitting device can be shortened, resulting in a reduction in power consumption. Furthermore, a reduction in driving time leads to inhibition of heat generation, so that the degree of deterioration of the light-emitting device can be reduced.

The structures described in this embodiment can be used in combination with any of the structures described in the other embodiments, as appropriate.

Embodiment 5

In this embodiment, examples of a variety of electronic devices and an automobile manufactured using the light-emitting device of one embodiment of the present invention or a light-emitting apparatus including the light-emitting device of one embodiment of the present invention will be described. Note that the light-emitting apparatus can be used mainly in a display portion of the electronic device described in this embodiment.

Electronic devices illustrated in FIGS. 4A to 4E can include a housing 7000, a display portion 7001, a speaker 7003, an LED lamp 7004, operation keys 7005 (including a power switch or an operation switch), a connection terminal 7006, a sensor 7007 (a sensor having a function of measuring force, displacement, position, speed, acceleration, angular velocity, rotational frequency, distance, light, liquid, magnetism, temperature, a chemical substance, sound, time, hardness, an electric field, current, voltage, electric power, radiation, flow rate, humidity, gradient, oscillation, odor, or infrared ray), a microphone 7008, and the like.

Figure 4A:
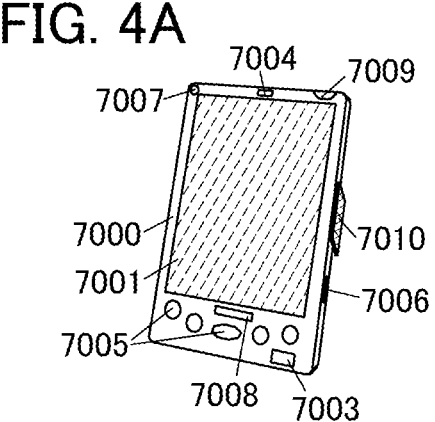
FIG. 4A illustrates a mobile computer.

FIG. 4A illustrates a mobile computer that can include a switch 7009, an infrared port 7010, and the like in addition to the above components.

Figure 4B:
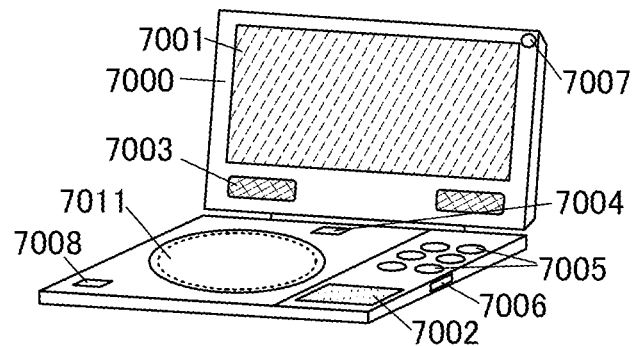
FIG. 4B illustrates a portable image reproducing device.

FIG. 4B illustrates a portable image reproducing device (e.g., a DVD player) that is provided with a recording medium and can include a second display portion 7002, a recording medium reading portion 7011, and the like in addition to the above components.

Figure 4C:
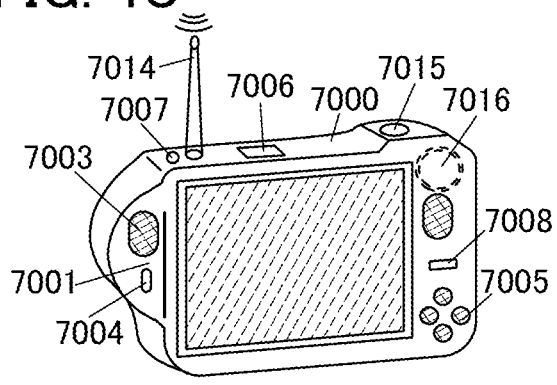
FIG. 4C illustrates a digital camera.

FIG. 4C illustrates a digital camera that has a television reception function and can include an antenna 7014, a shutter button 7015, an image receiving portion 7016, and the like in addition to the above components.

Figure 4D:
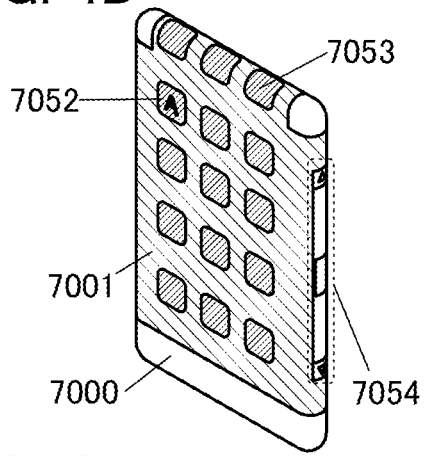
FIG. 4D illustrates a portable information terminal.

FIG. 4D illustrates a portable information terminal. The portable information terminal has a function of displaying information on three or more surfaces of the display portion 7001. Here, information 7052, information 7053, and information 7054 are displayed on different surfaces. For example, a user of the portable information terminal can check the information 7053 displayed such that it can be seen from above the portable information terminal, with the portable information terminal put in a breast pocket of his/her clothes. Thus, the user can see the display without taking out the portable information terminal from the pocket and decide whether to answer the call, for example.

Figure 4E:
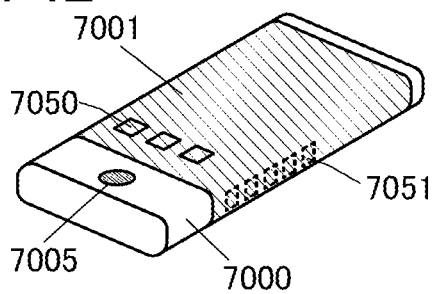
FIG. 4E illustrates a portable information terminal.

FIG. 4E illustrates a portable information terminal (e.g., a smartphone) and can include the display portion 7001, the operation key 7005, and the like in the housing 7000. Note that the portable information terminal may include a speaker 7003, a connection terminal 7006, a sensor 7007, or the like. The portable information terminal can display text and image data on its plurality of surfaces. Here, three icons 7050 are displayed. Furthermore, information 7051 indicated by dashed rectangles can be displayed on another surface of the display portion 7001. Examples of the information 7051 include notification of reception of an e-mail, an SNS message, an incoming call, or the like, the title and sender of an e-mail, an SNS message, or the like, the date, the time, remaining battery, and the reception strength of an antenna. The icon 7050 or the like may be displayed at the position where the information 7051 is displayed.

Figure 4F:
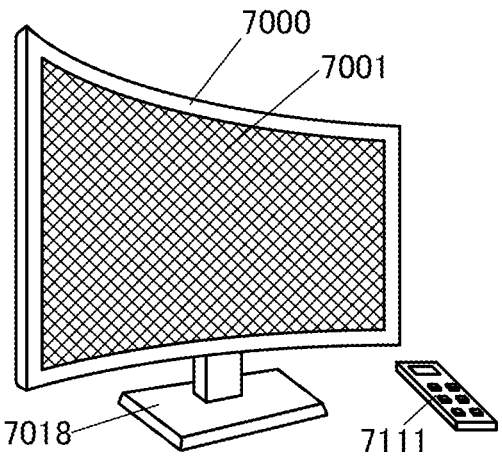
FIG. 4F illustrates a television set.

FIG. 4F illustrates a large-size television set (also referred to as TV or a television receiver) and can include the housing 7000, the display portion 7001, and the like. In addition, here, the housing 7000 is supported by a stand 7018. The television set can be operated with a separate remote controller 7111 or the like. The display portion 7001 may include a touch sensor. The television set can be operated by touching the display portion 7001 with a finger or the like. The remote controller 7111 may be provided with a display portion for displaying information output from the remote controller 7111. With operation keys or a touch panel of the remote controller 7111, channels and volume can be controlled and images displayed on the display portion 7001 can be controlled.

The electronic devices illustrated in FIGS. 4A to 4F can have a variety of functions, such as a function of displaying a variety of information (a still image, a moving image, a text image, and the like) on the display portion, a touch panel function, a function of displaying a calendar, date, time, and the like, a function of controlling processing with a variety of types of software (programs), a wireless communication function, a function of being connected to a variety of computer networks with a wireless communication function, a function of transmitting and receiving a variety of data with a wireless communication function, and a function of reading a program or data stored in a recording medium and displaying the program or data on the display portion. Furthermore, the electronic device including a plurality of display portions can have a function of displaying image data mainly on one display portion while displaying text data mainly on another display portion, a function of displaying a three-dimensional image by displaying images on a plurality of display portions with a parallax taken into account, or the like. Furthermore, the electronic device including an image receiving portion can have a function of shooting a still image, a function of shooting a moving image, a function of automatically or manually correcting a shot image, a function of storing a shot image in a recording medium (an external recording medium or a recording medium incorporated in the camera), a function of displaying a shot image on the display portion, or the like. Note that functions that can be provided for the electronic devices illustrated in FIGS. 4A to 4F are not limited to those described above, and the electronic devices can have a variety of functions.

Figure 4G:
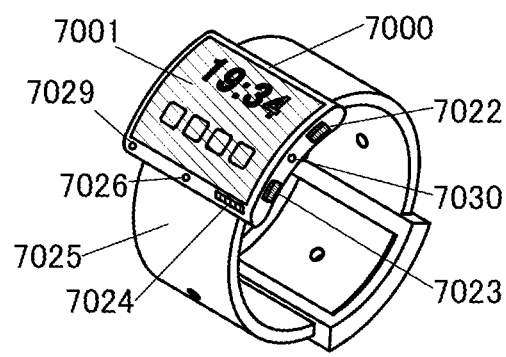
FIG. 4G illustrates a portable information terminal.

FIG. 4G illustrates a watch-type portable information terminal, which can be used as a smart watch, for example. The watch-type portable information terminal includes the housing 7000, the display portion 7001, operation buttons 7022 and 7023, a connection terminal 7024, a band 7025, a microphone 7026, a sensor 7029, a speaker 7030, and the like. The display surface of the display portion 7001 is curved, and images can be displayed on the curved display surface.

Furthermore, mutual communication between the portable information terminal and, for example, a headset capable of wireless communication can be performed, and thus hands-free calling is possible with the portable information terminal. Note that the connection terminal 7024 allows mutual data transmission with another information terminal and charging. Wireless power feeding can also be employed for the charging operation.

The display portion 7001 mounted in the housing 7000 serving as a bezel includes a non-rectangular display region. The display portion 7001 can display an icon indicating time, another icon, and the like. The display portion 7001 may be a touch panel (input/output device) including a touch sensor (input device).

The smart watch illustrated in FIG. 4G can have a variety of functions, such as a function of displaying a variety of information (a still image, a moving image, a text image, and the like) on the display portion, a touch panel function, a function of displaying a calendar, date, time, and the like, a function of controlling processing with a variety of types of software (programs), a wireless communication function, a function of being connected to a variety of computer networks with a wireless communication function, a function of transmitting and receiving a variety of data with a wireless communication function, and a function of reading a program or data stored in a recording medium and displaying the program or data on the display portion.

The housing 7000 can include a speaker, a sensor (a sensor having a function of measuring force, displacement, position, speed, acceleration, angular velocity, rotational frequency, distance, light, liquid, magnetism, temperature, a chemical substance, sound, time, hardness, an electric field, current, voltage, electric power, radiation, flow rate, humidity, gradient, oscillation, odor, or infrared rays), a microphone, and the like.

Note that the light-emitting apparatus of one embodiment of the present invention can be used in the display portion of each electronic device described in this embodiment, so that a long-lifetime electronic device can be obtained.

Figure 5A:
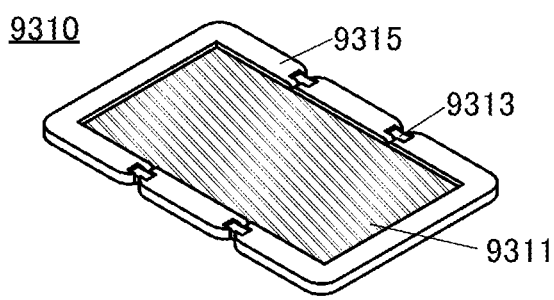
FIGS. 5A to 5C illustrate an electronic device.
Figure 5B:
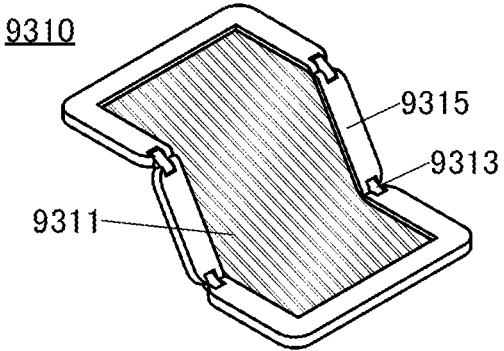
Figure 5C:
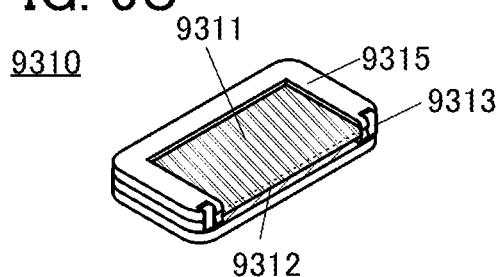

Another electronic device including the light-emitting apparatus is a foldable portable information terminal illustrated in FIGS. 5A to 5C. FIG. 5A illustrates a portable information terminal 9310 which is opened. FIG. 5B illustrates the portable information terminal 9310 which is being opened or being folded. FIG. 5C illustrates the portable information terminal 9310 which is folded. The portable information terminal 9310 is highly portable when folded. The portable information terminal 9310 is highly browsable when opened because of a seamless large display region.

A display portion 9311 is supported by three housings 9315 joined together by hinges 9313. Note that the display portion 9311 may be a touch panel (input/output device) including a touch sensor (input device). By bending the display portion 9311 at a connection portion between two housings 9315 with the use of the hinges 9313, the portable information terminal 9310 can be reversibly changed in shape from an opened state to a folded state. The light-emitting apparatus of one embodiment of the present invention can be used for the display portion 9311. In addition, a long-lifetime electronic device can be obtained. A display region 9312 in the display portion 9311 is a display region that is positioned at a side surface of the portable information terminal 9310 which is folded. On the display region 9312, information icons, file shortcuts of frequently used applications or programs, and the like can be displayed, and confirmation of information and start of application and the like can be smoothly performed.

Figure 6A:
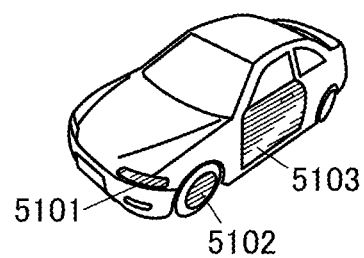
FIGS. 6A and 6B illustrate an automobile.
Figure 6B:
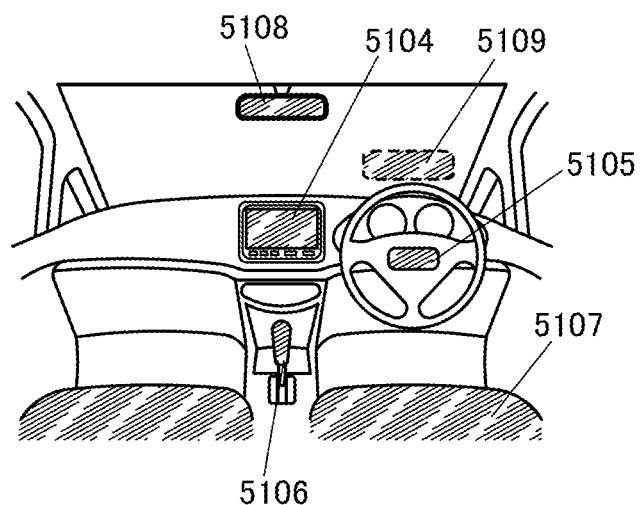

FIGS. 6A and 6B illustrate an automobile including the light-emitting apparatus. The light-emitting apparatus can be incorporated in the automobile, and specifically, can be included in lights 5101 (including lights of the rear part of the car), a wheel cover 5102, a part or whole of a door 5103, or the like on the outer side of the automobile which is illustrated in FIG. 6A. The light-emitting apparatus can also be included in a display portion 5104, a steering wheel 5105, a gear lever 5106, a seat 5107, an inner rearview mirror 5108, an windshield 5109, or the like on the inner side of the automobile which is illustrated in FIG. 6B, or in a part of a glass window.

In the above manner, the electronic devices and automobiles can be obtained using the light-emitting apparatus of one embodiment of the present invention. In that case, a long-lifetime electronic device can be obtained. Note that the light-emitting apparatus can be used for electronic devices and automobiles in a variety of fields without being limited to those described in this embodiment.

The structures described in this embodiment can be used in combination with any of the structures described in the other embodiments, as appropriate.

Embodiment 6

In this embodiment, the structure of a lighting device fabricated using the light-emitting apparatus of one embodiment of the present invention or the light-emitting device which is part of the light-emitting apparatus will be described with reference to FIGS. 7A and 7B.

Figure 7A:
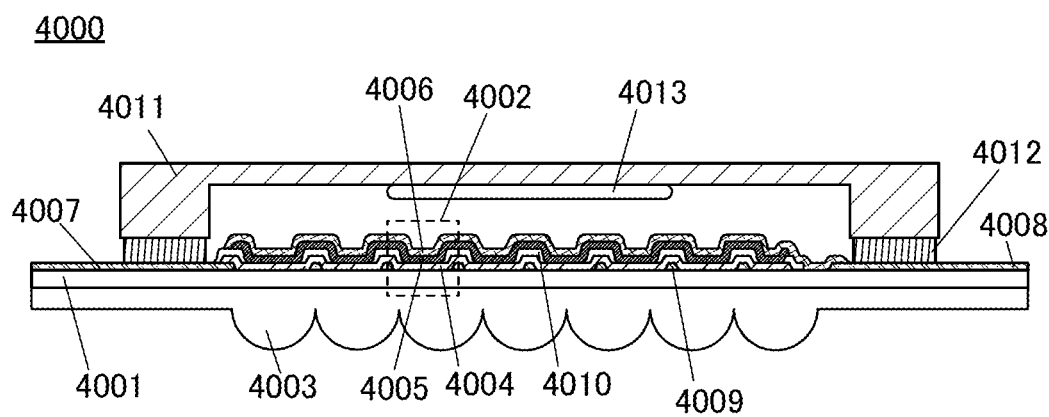
FIGS. 7A and 7B illustrate lighting devices.
Figure 7B:
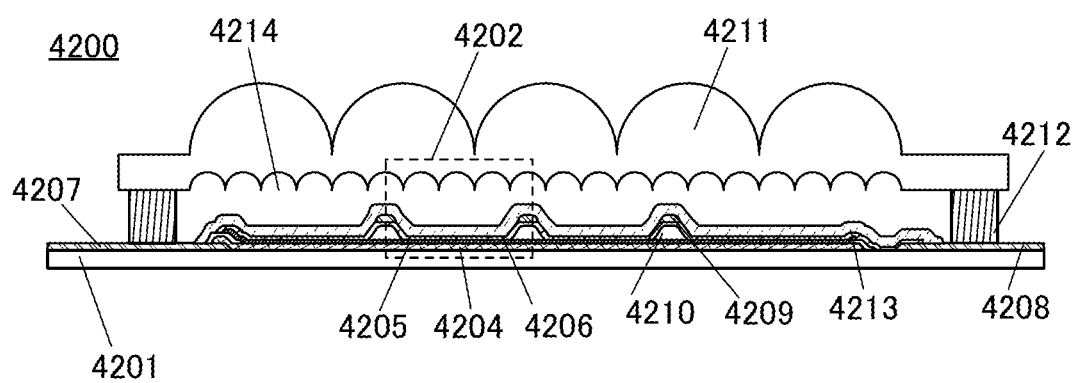

FIGS. 7A and 7B are examples of cross-sectional views of lighting devices. FIG. 7A illustrates a bottom-emission lighting device in which light is extracted from the substrate side, and FIG. 7B illustrates a top-emission lighting device in which light is extracted from the sealing substrate side.

A lighting device 4000 illustrated in FIG. 7A includes a light-emitting device 4002 over a substrate 4001. In addition, the lighting device 4000 includes a substrate 4003 with unevenness on the outside of the substrate 4001. The light-emitting device 4002 includes a first electrode 4004, an EL layer 4005, and a second electrode 4006.

The first electrode 4004 is electrically connected to an electrode 4007, and the second electrode 4006 is electrically connected to an electrode 4008. In addition, an auxiliary wiring 4009 electrically connected to the first electrode 4004 may be provided. Note that an insulating layer 4010 is formed over the auxiliary wiring 4009.

The substrate 4001 and a sealing substrate 4011 are bonded to each other with a sealant 4012. A desiccant 4013 is preferably provided between the sealing substrate 4011 and the light-emitting device 4002. The substrate 4003 has the unevenness illustrated in FIG. 7A, whereby the extraction efficiency of light emitted from the light-emitting device 4002 can be increased.

A lighting device 4200 illustrated in FIG. 7B includes a light-emitting device 4202 over a substrate 4201. The light-emitting device 4202 includes a first electrode 4204, an EL layer 4205, and a second electrode 4206.

The first electrode 4204 is electrically connected to an electrode 4207, and the second electrode 4206 is electrically connected to an electrode 4208. An auxiliary wiring 4209 electrically connected to the second electrode 4206 may be provided. An insulating layer 4210 may be provided under the auxiliary wiring 4209.

The substrate 4201 and a sealing substrate 4211 with unevenness are bonded to each other with a sealant 4212. A barrier film 4213 and a planarization film 4214 may be provided between the sealing substrate 4211 and the light-emitting device 4202. The sealing substrate 4211 has the unevenness illustrated in FIG. 7B, whereby the extraction efficiency of light emitted from the light-emitting device 4202 can be increased.

Examples of such lighting devices include a ceiling light as an indoor lighting.

Examples of the ceiling light include a direct-mount light and an embedded light. Such lighting devices are fabricated using the light-emitting apparatus and a housing or a cover in combination.

For another example, such lighting devices can be used for a foot light that lights a floor so that safety on the floor can be improved. A foot light can be effectively used in a bedroom, on a staircase, or on a passage, for example. In that case, the size or shape of the foot light can be changed in accordance with the area or structure of a room. The foot light can be a stationary lighting device fabricated using the light-emitting apparatus and a support in combination.

Such lighting devices can also be used for a sheet-like lighting device (sheet-like lighting). The sheet-like lighting, which is attached to a wall when used, is space-saving and thus can be used for a wide variety of uses. Furthermore, the area of the sheet-like lighting can be easily increased. The sheet-like lighting can also be used on a wall or housing having a curved surface.

Besides the above examples, when the light-emitting apparatus of one embodiment of the present invention or the light-emitting device which is part of the light-emitting apparatus is used as part of furniture in a room, a lighting device that functions as the furniture can be obtained.

As described above, a variety of lighting devices that include the light-emitting apparatus can be obtained. Note that these lighting devices are also embodiments of the present invention.

The structures described in this embodiment can be used in combination with any of the structures described in the other embodiments, as appropriate.

Example 1

Synthesis Example 1

This example will describe a method for synthesizing 2-phenyl-3-{4-[10-(3-pyridyl)-9-anthryl]phenyl}quinoxaline (abbreviation: PyA1PQ), the organic compound of one embodiment of the present invention represented by Structural Formula (100) in Embodiment 1. The structure of PyA1PQ is shown below.

[Chemical Formula 26]

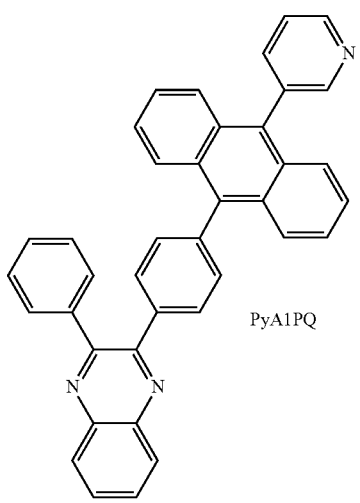

PyA1PQ
(100)

Into a 50 mL three-neck flask were added 0.74 g (2.2 mmol) of 3-(10-bromo-9-anthryl)pyridine, 0.26 g (0.85 mmol) of tri(ortho-tolyl)phosphine, 0.73 g (2.3 mmol) of 4-(3-phenylquinoxalin-2-yl)phenylboronic acid, 1.3 g (9.0 mmol) of an aqueous solution of potassium carbonate, 40 mL of ethylene glycol dimethyl ether (DME), and 4.4 mL of water. The mixture was degassed by being stirred under reduced pressure, and the air in the flask was replaced with nitrogen.

To the mixture in the flask was added 65 mg (0.29 mmol) of palladium(II) acetate, and the mixture was stirred under a nitrogen stream at 80° C. for 11 hours. After the stirring, water was added to the mixture in the flask, followed by extraction with toluene. The obtained solution of the extract was washed with saturated brine, and drying with magnesium sulfate was performed. The mixture was gravity filtered, and the filtrate was concentrated to give an oily substance. The obtained oily substance was purified twice by silica gel column chromatography, first using chloroform and then using toluene:ethyl acetate=5:1 and recrystallized with toluene/hexane, giving 0.43 g of a target yellow solid in a yield of 36%. Synthesis Scheme (a-1) is shown below.

[Chemical Formulae 27]

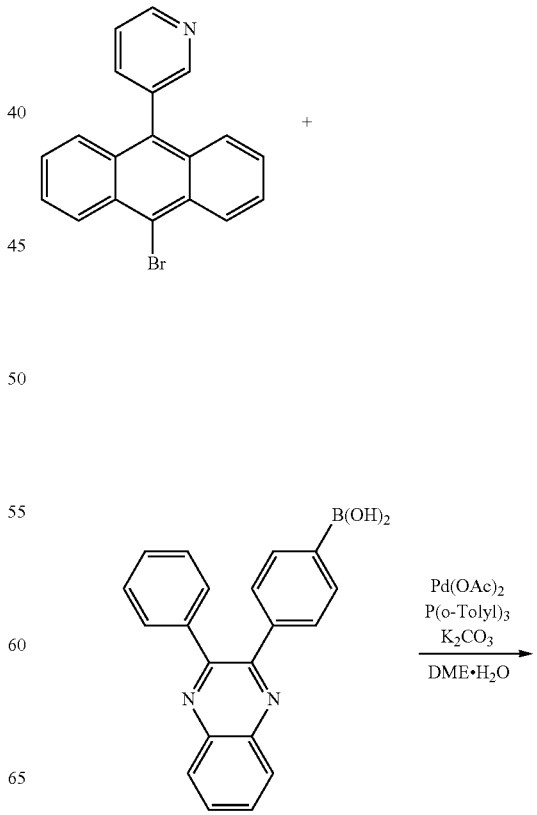

(a-1)

-continued

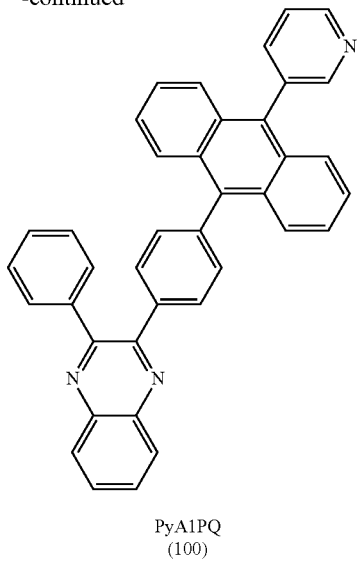

PyA1PQ
(100)

By a train sublimation method, 0.44 g of the obtained yellow solid was purified. The sublimation purification was performed under the conditions of the pressure being 10 Pa and the argon flow rate being 5.0 mL/min, by heating at 260° C. for 18 hours. After the purification, 0.35 g of a target yellow solid was obtained at a collection rate of 79%.

Figure 8:
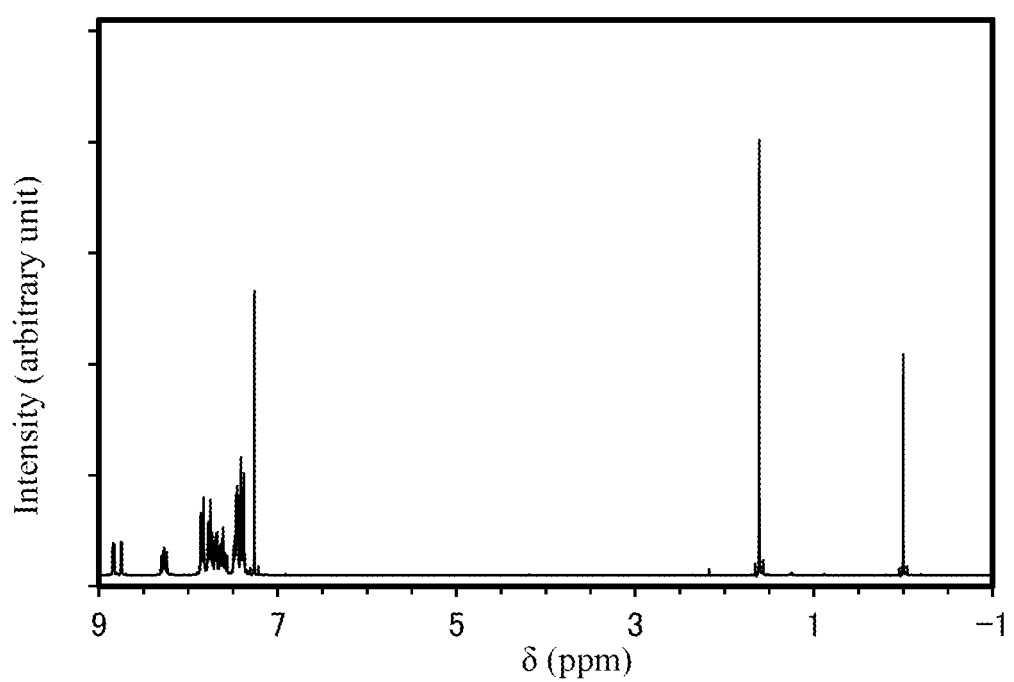
FIG. 8 shows a $^1$H-NMR chart of an organic compound represented by Structural Formula (100).

Analysis results by nuclear magnetic resonance ($^1$H-NMR) spectroscopy of the yellow solid obtained by the above reaction are shown below. A $^1$H-NMR chart is shown in FIG. 8. These results reveal that PyA1PQ, the organic compound of one embodiment of the present invention represented by Structural Formula (100) above, was obtained in this example.

$^1$H NMR (CDCl3, 300 MHz): δ=7.37-7.50 (m, 9H), 7.56-7.78 (m, 9H), 7.82-7.86 (m, 3H), 8.24-8.30 (m, 2H), 8.75 (dd, J=1.8 Hz, 0.9 Hz, 1H), 8.84 (dd, J=4.8 Hz, 1.8 Hz, 1H).

<<Physical properties of PyA1PQ>>

Next, ultraviolet-visible absorption spectra (hereinafter simply referred to as "absorption spectra") and emission spectra of PyA1PQ in a toluene solution and a solid thin film of PyA1PQ were measured.

Figure 9:
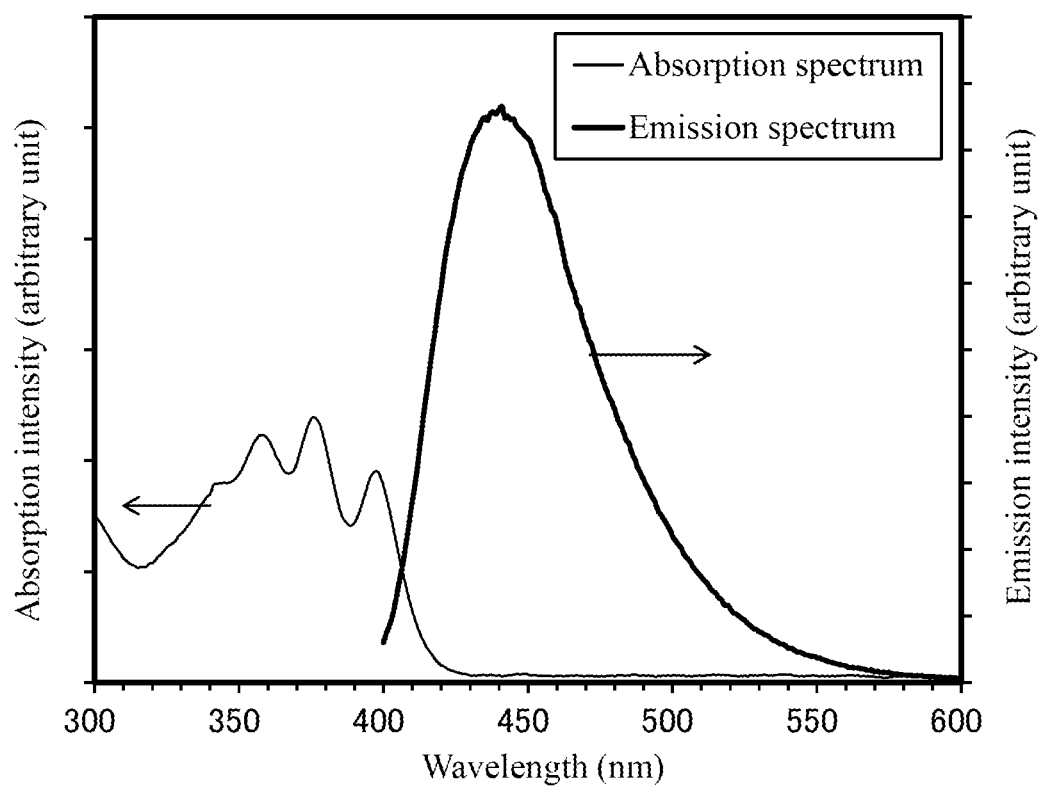
FIG. 9 shows ultraviolet-visible absorption and emission spectra of an organic compound represented by Structural Formula (100).

The absorption spectrum of PyA1PQ in the toluene solution was measured using an ultraviolet-visible spectrophotometer (V-550, produced by JASCO Corporation). The emission spectrum of PyA1PQ in the toluene solution was measured using a fluorescence spectrophotometer (FS920, produced by Hamamatsu Photonics K.K.). Note that the absorption spectrum of PyA1PQ in the toluene solution was calculated by subtraction of the measured absorption spectrum of only toluene in a quartz cell. FIG. 9 shows the obtained absorption and emission spectra of PyA1PQ in the toluene solution. The horizontal axis represents wavelength and the vertical axes represent absorption intensity and emission intensity.

From the results in FIG. 9, for the toluene solution of PyA1PQ, absorption peaks were observed at around 397 nm, 376 nm, and 358 nm, and an emission wavelength peak was observed at around 446 nm (excitation wavelength: 397 nm).

Figure 10:
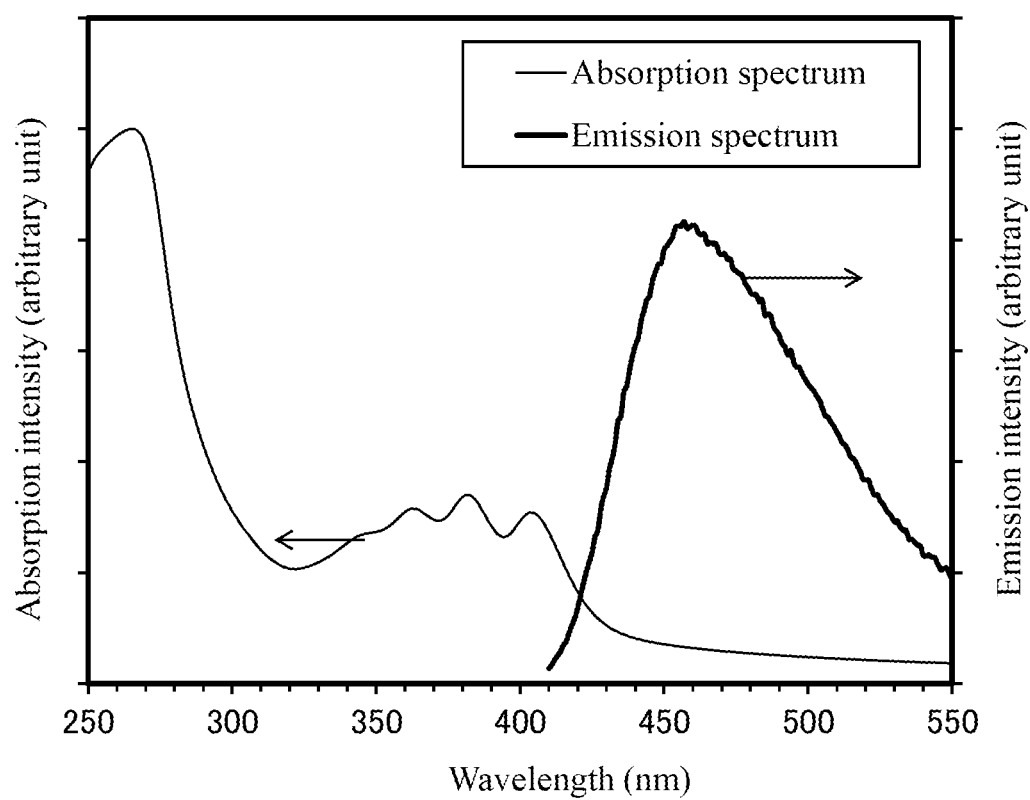
FIG. 10 shows ultraviolet-visible absorption and emission spectra of an organic compound represented by Structural Formula (100).

The solid thin film of PyA1PQ was fabricated over a quartz substrate by a vacuum evaporation method. The absorption spectrum of the solid thin film was measured using an ultraviolet-visible spectrophotometer (V-550, produced by JASCO Corporation). The emission spectrum of the solid thin film was measured using a fluorescence spectrophotometer (FS920, produced by Hamamatsu Photonics K.K.). Note that the absorption spectrum of the solid thin film was calculated by subtraction of the absorption spectrum of the quartz substrate. FIG. 10 shows the obtained absorption and emission spectra of the solid thin film of PyA1PQ. The horizontal axis represents wavelength and the vertical axes represent absorption intensity and emission intensity.

From the results in FIG. 10, for the solid thin film of PyA1PQ, absorption peaks were observed at around 404 nm, 382 nm, and 363 nm, and an emission wavelength peak was observed at around 457 nm (excitation wavelength: 394 nm).

The results reveal that PyA1PQ emits blue light. Moreover, PyA1PQ, the organic compound of one embodiment of the present invention, can be used as a host for a light-emitting substance or a substance which emits fluorescence in the visible region.

Next, the HOMO level and the LUMO level of PyA1PQ were obtained through a cyclic voltammetry (CV) measurement. The calculation method is shown below. An electrochemical analyzer (ALS model 600A or 600C, produced by BAS Inc.) was used as the measurement apparatus. A solution for the CV measurement was prepared in the following manner: tetra-n-butylammonium perchlorate (n-Bu$_4$NClO$_4$, produced by Tokyo Chemical Industry Co., Ltd., catalog No. T0836) as a supporting electrolyte was dissolved in dehydrated dimethylformamide (DMF, produced by Sigma-Aldrich Co. LLC., 99.8%, catalog No. 22705-6) as a solvent at a concentration of 100 mmol/L, and the object to be measured was dissolved therein at a concentration of 2 mmol/L.

A platinum electrode (PTE platinum electrode, produced by BAS Inc.) was used as a working electrode, another platinum electrode (Pt counter electrode for VC-3 (5 cm), produced by BAS Inc.) was used as an auxiliary electrode, and an Ag/Ag$^+$ electrode (RE7 reference electrode for a nonaqueous solvent, produced by BAS Inc.) was used as a reference electrode. Note that the measurement was performed at a room temperature (20° C. to 25° C.).

Here, the scan speed in the CV measurement was fixed to 0.1 V/sec, and an oxidation potential Ea [V] and a reduction potential Ec [V] with respect to the reference electrode were measured. The potential Ea is an intermediate potential of an oxidation-reduction wave, and the potential Ec is an intermediate potential of a reduction-oxidation wave. Since the potential energy of the reference electrode used in this example with respect to the vacuum level is −4.94 [eV], the HOMO level and the LUMO level can be calculated by the following formulae: HOMO level [eV]=−4.94−Ea, and LUMO level [eV]=−4.94−Ec.

As a result, it was found that the HOMO level of PyA1PQ was −5.91 eV and the LUMO level thereof was −3.00 eV.

Example 2

Figure 11:
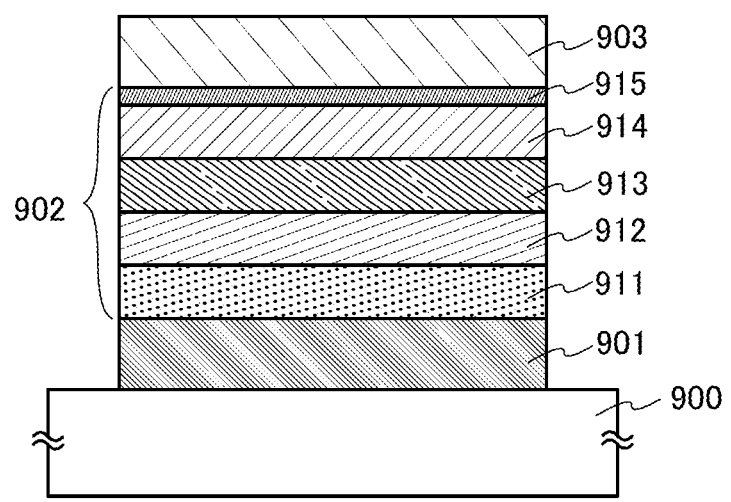
FIG. 11 illustrates a light-emitting device.

Described in this example are element structures, fabrication methods, and properties of a light-emitting device 1 which is a light-emitting device of one embodiment of the present invention and comparative light-emitting devices 2 and 3 which are light-emitting devices for comparison. The light-emitting device 1 includes 2-phenyl-3-{4-[10-(3-pyridyl)-9-anthryl]phenyl}quinoxaline (abbreviation: PyA1PQ) (Structural Formula (100)) described in Example 1 in an electron-transport layer, the comparative light-emitting device 2 includes 2,3-bis[4-(10-phenyl-9-anthryl)phenyl]quinoxaline (abbreviation; PAPQ) in an electron-transport layer, and the comparative light-emitting device 3 includes 2-phenyl-3-[4-(10-phenyl-9-anthryl)phenyl]quinoxaline (abbreviation: PA1PQ) in an electron-transport layer. Note that FIG. 11 illustrates an element structure of the light-emitting devices used in this example, and Table 1 shows specific structures. The chemical formulae of materials used in this example are shown below.

TABLE 1
| | first electrode 901 | hole-injection layer 911 | hole-transport layer 912 | light-emitting layer 913 | electron-transport layer 914 | | electron-injection layer 915 | second electrode 903 |
|---|---|---|---|---|---|---|---|---|
| light-emitting device 1 | ITSO (110 nm) | NPB:MoOx (4:1, 50 nm) | NPB (10 nm) | * | Alq (10 nm) | PyA1PQ (20 nm) | LiF (1 nm) | Al (200 nm) |
| comparative light-emitting device 2 | | | | | | PAPQ (20 nm) | | |
| comparative light-emitting device 3 | | | | | | PA1PQ (20 nm) | | |
* CzPA:PCBAPA (1:0.1, 30 nm)
[Chemical Formulae 28]
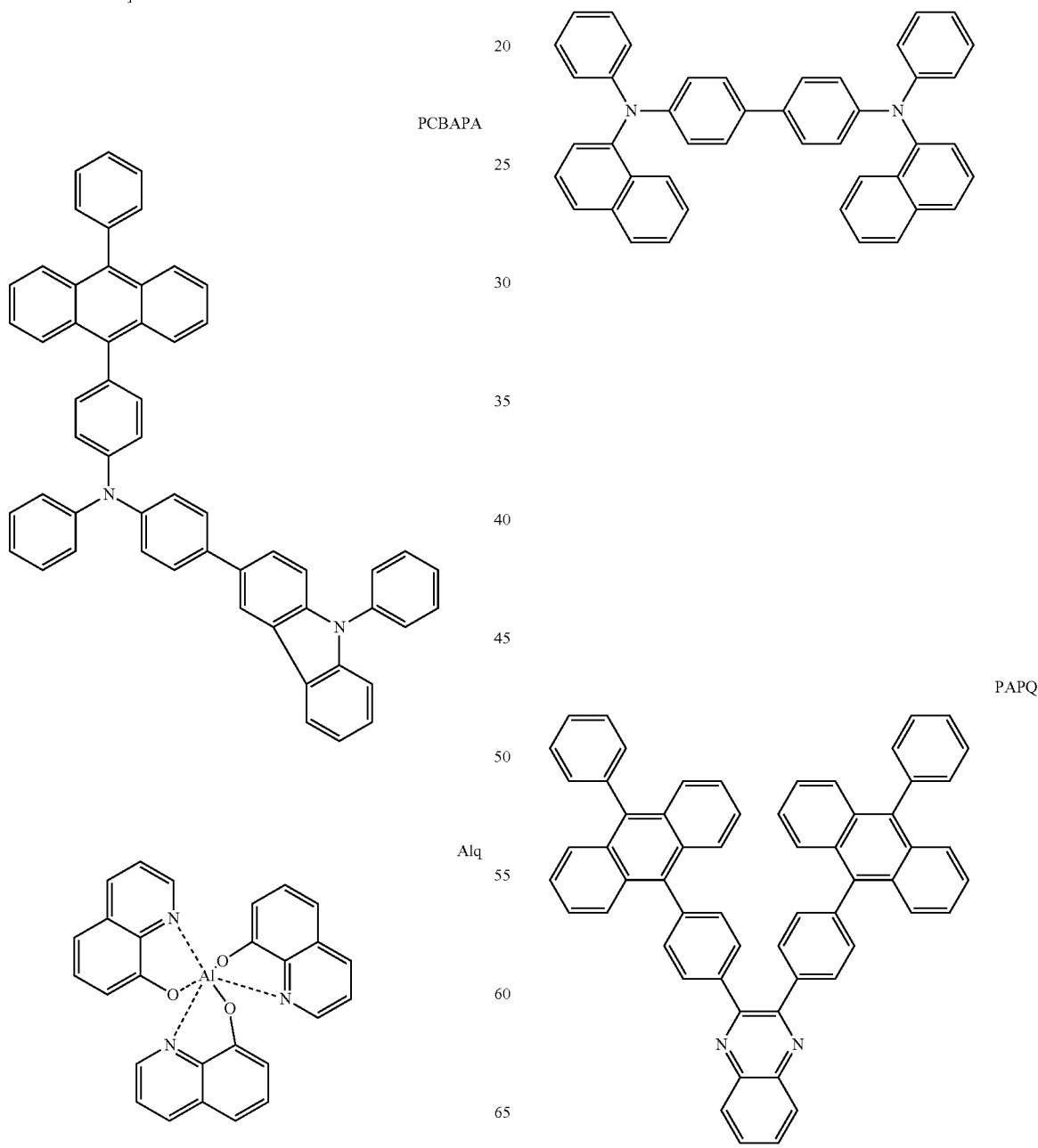

PA1PQ

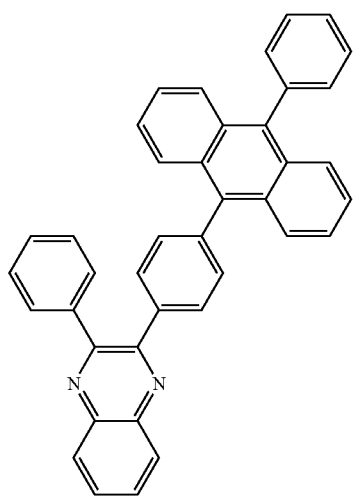

CzPA

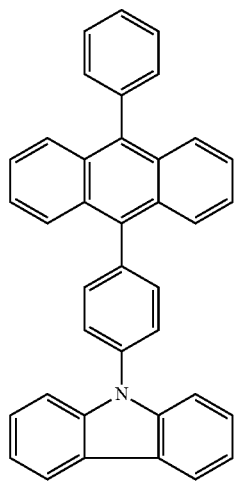

PyA1PQ

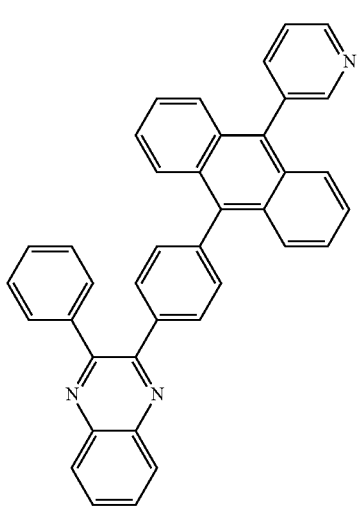

<<Fabrication of Light-Emitting Devices>>

In each of the light-emitting devices described in this example, as illustrated in FIG. 11, a hole-injection layer 911, a hole-transport layer 912, a light-emitting layer 913, an electron-transport layer 914, and an electron-injection layer 915, which constitute an EL layer 902, are stacked in this order over a first electrode 901 formed over a substrate 900, and a second electrode 903 is stacked over the electron-injection layer 915.

First, the first electrode 901 was formed over the substrate 900. The electrode area was set to 4 mm$^2$ (2 mm×2 mm). A glass substrate was used as the substrate 900. The first electrode 901 was formed to a thickness of 110 nm using indium tin oxide containing silicon oxide (ITSO) by a sputtering method.

For pretreatment, a surface of the substrate was washed with water, baking was performed at 200° C. for 1 hour, and then UV ozone treatment was performed for 370 seconds. After that, the substrate was transferred into a vacuum evaporation apparatus where the pressure had been reduced to approximately $1 \times 10^{-4}$ Pa, and was subjected to vacuum baking at 170° C. for 30 minutes in a heating chamber of the vacuum evaporation apparatus, and then the substrate was cooled down for approximately 30 minutes.

Next, the hole-injection layer 911 was formed over the first electrode 901. After the pressure in the vacuum evaporation apparatus was reduced to $1 \times 10^{-4}$ Pa, the hole-injection layer 911 was formed by co-evaporation of 4,4'-bis[N-(1-naphthyl)-N-phenylamino]biphenyl (abbreviation: NPB) and molybdenum oxide to a thickness of 50 nm in a mass ratio of NPB to molybdenum oxide was 4:1.

Then, the hole-transport layer 912 was formed over the hole-injection layer 911. The hole-transport layer 912 was formed to a thickness of 10 nm by evaporation of NPB.

Next, the light-emitting layer 913 was formed over the hole-transport layer 912.

The light-emitting layer 913 was formed by co-evaporation of 9-[4-(10-phenyl-9-anthracenyl)phenyl]-9H-carbazole (abbreviation: CzPA) and 4-(10-phenyl-9-anthryl)-4'-(9-phenyl-9H-carbazol-3-yl)triphenylamine (abbreviation: PCBAPA) to a thickness of 30 nm in a weight ratio of CzPA to PCBAPA was 1:0.1.

Next, the electron-transport layer 914 was formed over the light-emitting layer 913. The electron-transport layer 914 was formed by an evaporation method using resistance heating.

The electron-transport layer 914 of the light-emitting device 1 was formed in such a manner that tris(8-quinolinolato)aluminum(III) (abbreviation: Alq) and PyA1PQ were sequentially deposited by evaporation to thicknesses of 10 nm and 20 nm, respectively. The electron-transport layer 914 of the comparative light-emitting device 2 was formed in such a manner that Alq and PAPQ were sequentially deposited by evaporation to thicknesses of 10 nm and 20 nm, respectively. The electron-transport layer 914 of the comparative light-emitting device 3 was formed in such a manner that Alq and PA1PQ were sequentially deposited by evaporation to thicknesses of 10 nm and 20 nm, respectively.

Then, the electron-injection layer 915 was formed over the electron-transport layer 914. The electron-injection layer 915 was formed to a thickness of 1 nm by evaporation of lithium fluoride (LiF).

After that, the second electrode 903 was formed over the electron-injection layer 915. The second electrode 903 was formed to a thickness of 200 nm by an evaporation method using aluminum. In this example, the second electrode 903 functions as a cathode.

Through the above steps, the light-emitting devices each including the EL layer between the pair of electrodes were formed over the substrate 900. Note that the hole-injection layer 911, the hole-transport layer 912, the light-emitting layer 913, the electron-transport layer 914, and the electron-injection layer 915 described above are functional layers forming the EL layer in one embodiment of the present invention. Furthermore, in all the evaporation steps in the above fabrication method, evaporation was performed by a resistance-heating method.

Each of the light-emitting devices fabricated as described above was sealed using another substrate (not illustrated) in such a manner that the substrate (not illustrated) to which a sealant to be cured by ultraviolet light was applied was fixed to the substrate 900 in a glove box containing a nitrogen atmosphere, and the substrates were bonded to each other such that the sealant was attached so as to surround the light-emitting device formed over the substrate 900. In the sealing process, the sealant was irradiated with 365-nm ultraviolet light at 6 J/cm² to be cured, and the sealant was heated at 80° C. for 1 hour to be stabilized.

<<Operation Characteristics of Light-Emitting Devices>>

Figure 12:
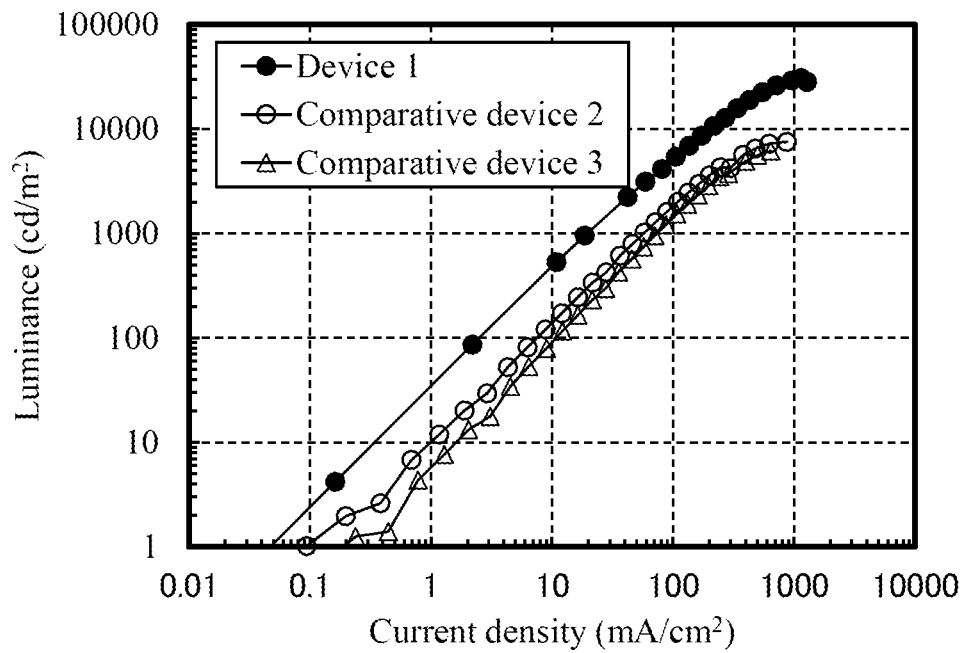
FIG. 12 shows the current density-luminance characteristics of a light-emitting device 1, a comparative light-emitting device 2, and a comparative light-emitting device 3.
Figure 13:
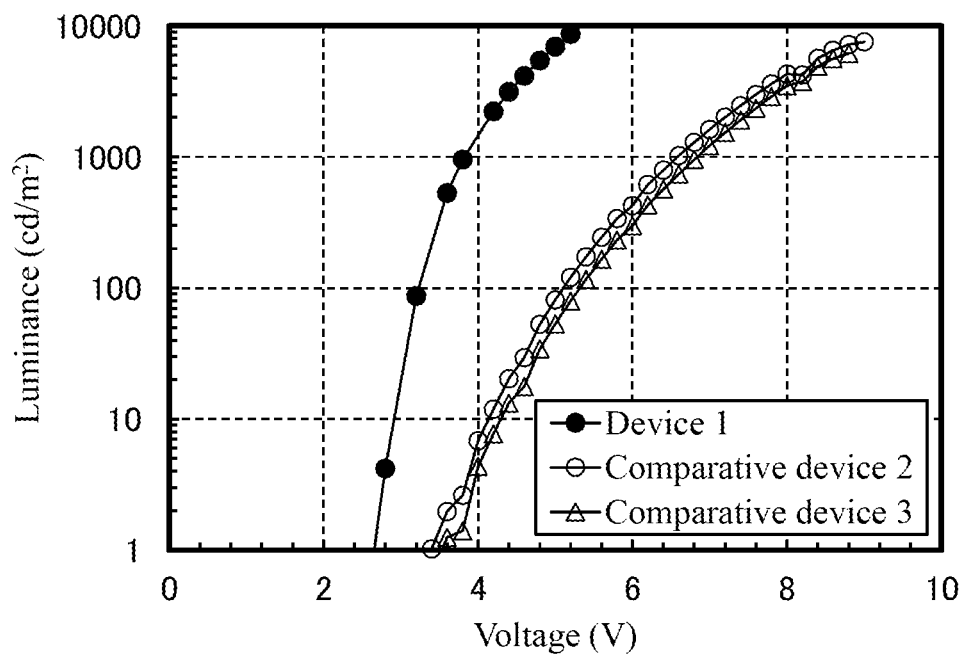
FIG. 13 shows the voltage-luminance characteristics of a light-emitting device 1, a comparative light-emitting device 2, and a comparative light-emitting device 3.
Figure 14:
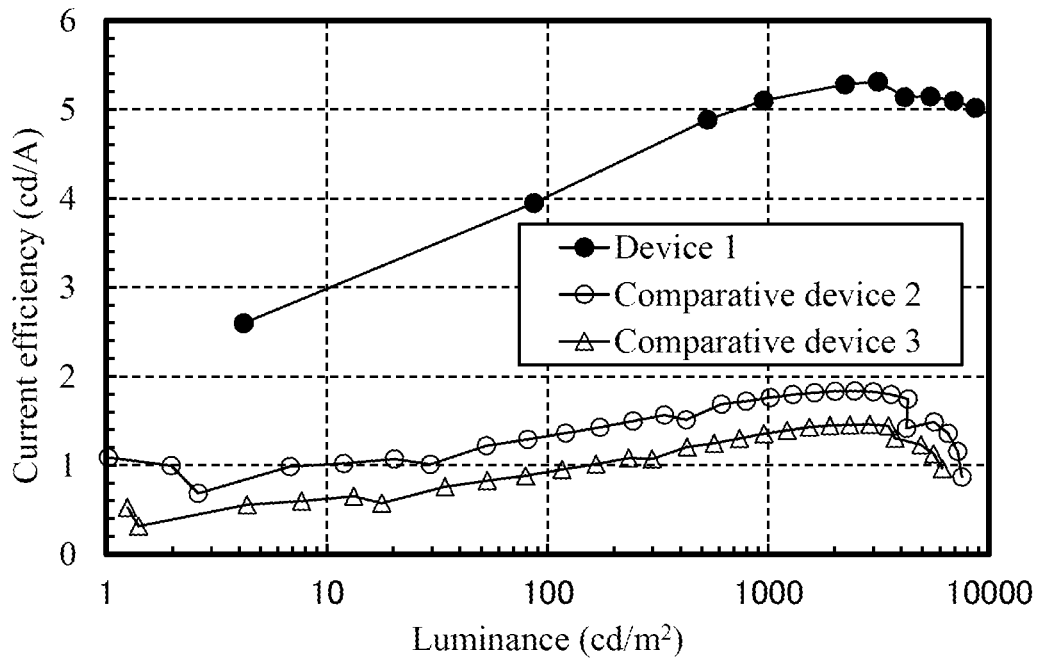
FIG. 14 shows the luminance-current efficiency characteristics of a light-emitting device 1, a comparative light-emitting device 2, and a comparative light-emitting device 3.
Figure 15:
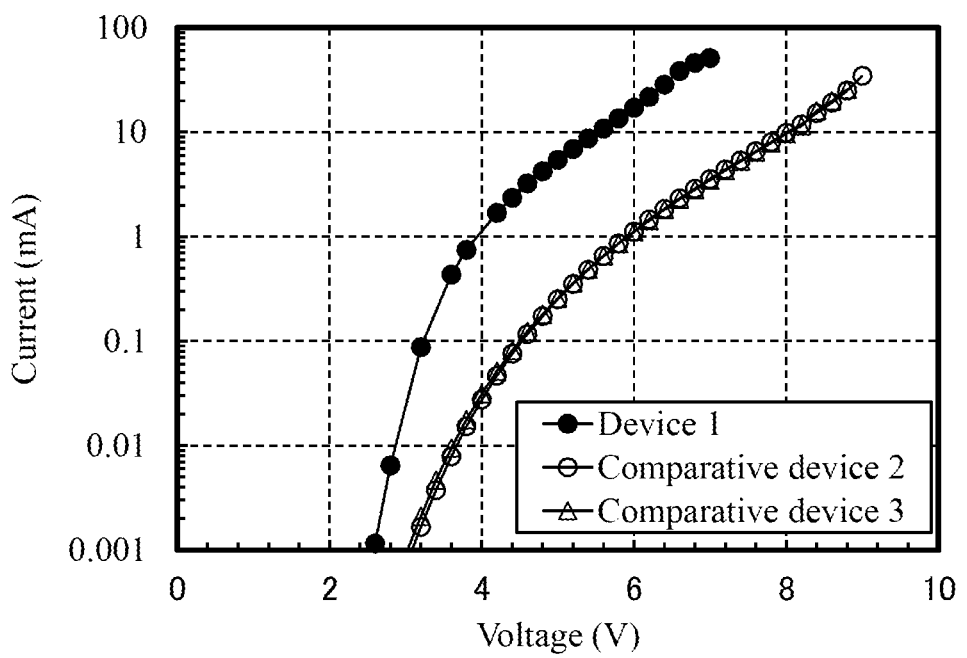
FIG. 15 shows the voltage-current characteristics of a light-emitting device 1, a comparative light-emitting device 2, and a comparative light-emitting device 3.

Operation characteristics of the fabricated light-emitting devices were measured. Note that the measurement was performed at room temperature (in an atmosphere kept at 25° C.). As the results of the operation characteristics of the light-emitting devices, the current density-luminance characteristics are shown in FIG. 12, the voltage-luminance characteristics are shown in FIG. 13, the luminance-current efficiency characteristics are shown in FIG. 14, and the voltage-current characteristics are shown in FIG. 15.

Table 2 shows the initial values of main characteristics of the light-emitting devices at around 1000 cd/m².

noxaline (abbreviation: PA1PQ), the organic compound used for the comparative light-emitting device 3 in Example 2 and represented by the following Structural Formula (200), is described specifically.

[Chemical Formula 29]

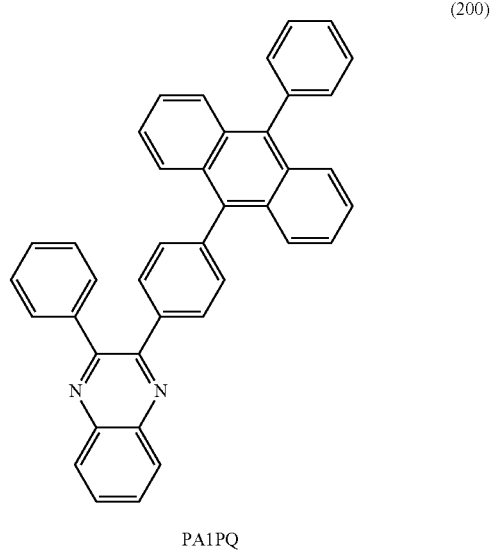

PA1PQ

TABLE 2

| | voltage (V) | current (mA) | current density (mA/cm²) | chromaticity (x, y) | luminance (cd/m²) | current efficiency (cd/A) | power efficiency (lm/W) | external quantum efficiency (%) |
|---|---|---|---|---|---|---|---|---|
| light-emitting device 1 | 3.8 | 0.75 | 19 | (0.16, 0.24) | 950 | 5.1 | 4.2 | 3.0 |
| comparative light-emitting device 2 | 6.6 | 2.3 | 58 | (0.16, 0.25) | 1000 | 1.8 | 0.84 | 0.98 |
| comparative light-emitting device 3 | 6.8 | 2.8 | 71 | (0.14, 0.27) | 960 | 1.4 | 0.63 | 0.73 |

Figure 16:
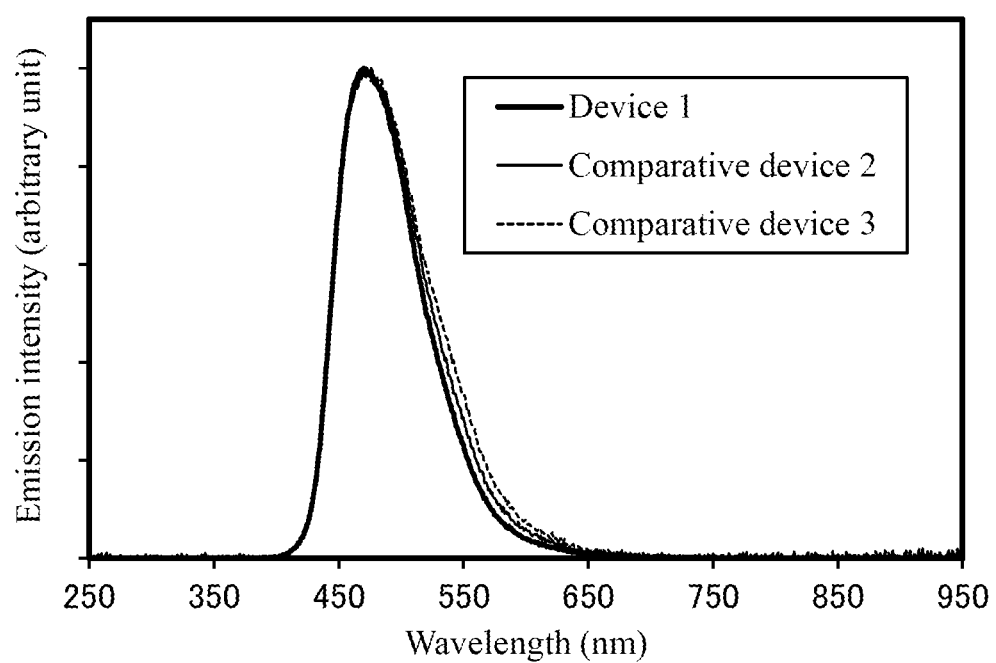
FIG. 16 shows the emission spectra of a light-emitting device 1, a comparative light-emitting device 2, and a comparative light-emitting device 3.

FIG. 16 shows emission spectra when current at a current density of 25 mA/cm² was supplied to the light-emitting devices. As shown in FIG. 16, the emission spectrum of each light-emitting device has a peak at around 470 nm, which is presumably derived from light emission of PCBAPA contained in the light-emitting layer 913.

The results shown in FIG. 12 to FIG. 15 and Table 2 show that the light-emitting device 1 of one embodiment of the present invention using PyA1PQ has current-voltage characteristics, power efficiency, and emission efficiency superior to those of the comparative light-emitting devices 2 and 3.

Figure 17:
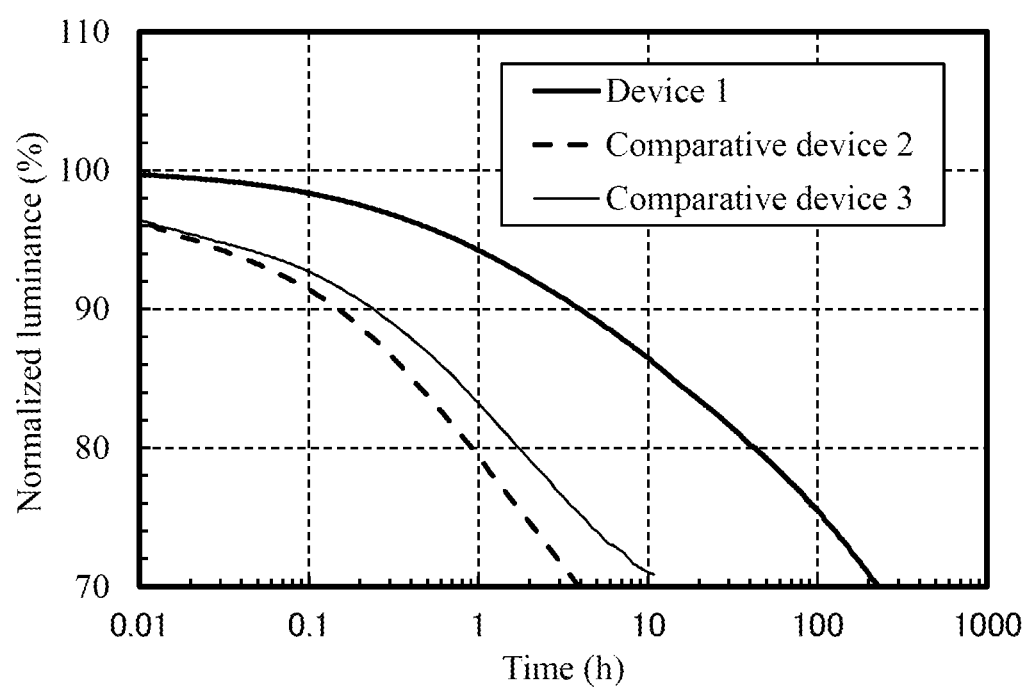
FIG. 17 shows the reliability of each of a light-emitting device 1, a comparative light-emitting device 2, and a comparative light-emitting device 3.

FIG. 17 is a graph showing a change in luminance over driving time at a luminance of 1000 cd/m². As shown in FIG. 17, the light-emitting device 1 of one embodiment of the present invention was found to be a long-lifetime light-emitting device with a small reduction in luminance over driving time.

Reference Synthesis Example

This reference synthesis example shows a synthesis example of 2-phenyl-3-[4-(10-phenyl-9-anthryl)phenyl]qui- Into a 100 mL recovery flask were added 1.0 g (3.0 mmol) of 9-bromo-10-phenylanthracene, 0.21 g (0.70 mmol) of tri(ortho-tolyl)phosphine, 1.0 g (3.0 mmol) of 4-(3-phenylquinoxalin-2-yl)phenylboronic acid, 0.85 g (6.2 mmol) of potassium carbonate, 30 mL of ethylene glycol dimethyl ether (DME), and 3.0 mL of water.

The pressure in the flask was reduced, the mixture was stirred, and then the air in the flask was replaced with nitrogen. To the mixture was added 62 mg (0.27 mmol) of palladium(II) acetate, which was refluxed under a nitrogen stream at 100° C. for 14 hours. After the reflux, water was added to the mixture in the flask, followed by extraction with toluene. The obtained solution of the extract was washed with saturated brine, and drying with magnesium sulfate was performed. The mixture was gravity filtered, and the filtrate was concentrated to give a solid. A toluene solution was added to the obtained solid, and suction filtration through Celite, Florisil, and alumina was conducted, whereby the filtrate was concentrated. The filtrate was purified by silica gel column chromatography (toluene) and recrystallized

87 with toluene/hexane, giving 0.91 g of a target pale yellow solid in a yield of 56%. Synthesis Scheme (x-1) is shown below.

[Chemical Formulae 30]

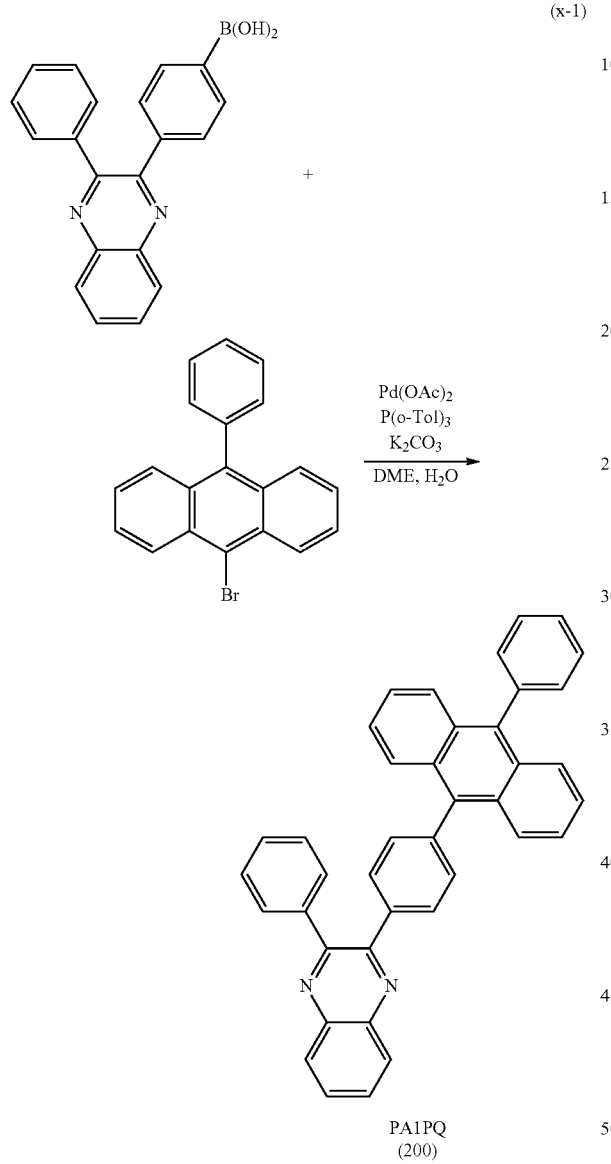

By a train sublimation method, 0.79 g of the obtained pale yellow solid was purified. The sublimation purification was performed under the conditions of the pressure being 10 Pa and the argon flow rate being 5.0 mL/min, by heating at 240° C. for 16 hours. After the purification, 0.79 g of a target pale yellow solid was obtained at a collection rate of 88%.

Figure 18:
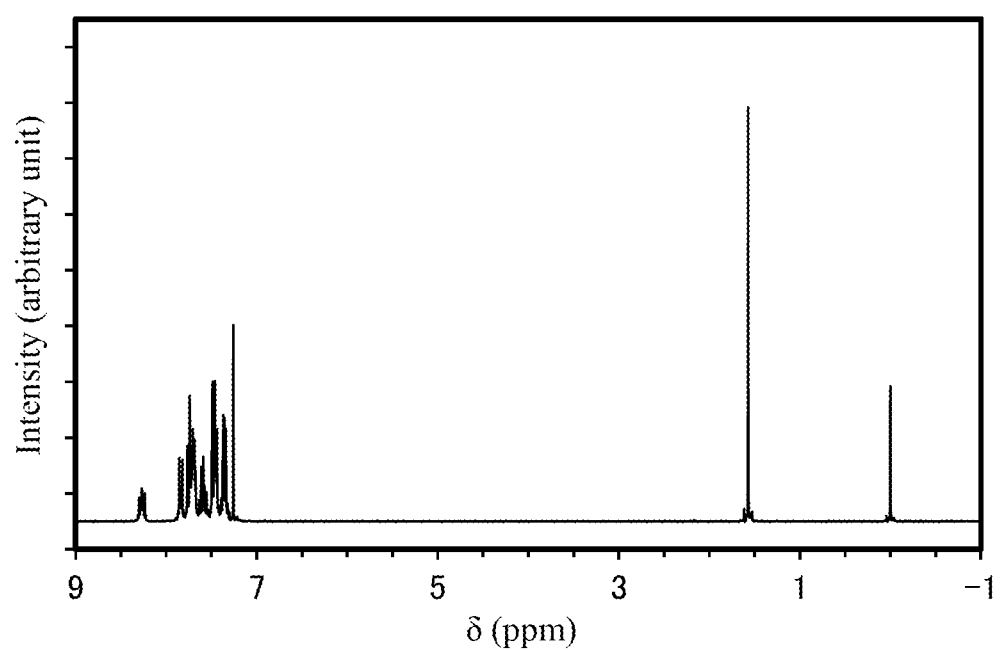
FIG. 18 shows a $^1$H-NMR chart of an organic compound represented by Structural Formula (200).

Analysis results by nuclear magnetic resonance ($^1$H-NMR) spectroscopy of the pale yellow solid obtained by the above reaction are shown below. A $^1$H-NMR chart is shown in FIG. 18. These results reveal that PA1PQ represented by Structural Formula (200) was obtained.

$^1$H NMR (CDCl3, 300 MHz): δ=7.31 m-7.40 (m, 4H), 7.43-7.77 (m, 18H), 7.81-7.87 (m, 2H), 8.24-8.30 (m, 2H).

88

Example 3

Synthesis Example 2

This example will describe a method for synthesizing 2-phenyl-3-{4-[10-(pyrimidin-5-yl)-9-anthryl]phenyl}quinoxaline (abbreviation: 1PQPmA), the organic compound of one embodiment of the present invention represented by Structural Formula (101) in Embodiment 1. The structure of 1PQPmA is shown below.

[Chemical Formula 31]

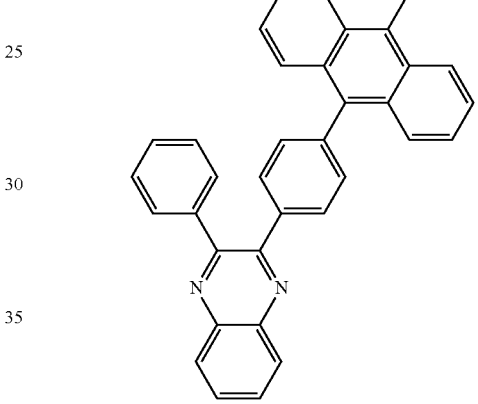

1PQPmA

Into a 50 mL three-neck flask were added 1.1 g (3.4 mmol) of 5-(10-bromo-9-anthryl)pyrimidine, 0.23 g (0.76 mmol) of tri(ortho-tolyl)phosphine, 1.3 g (3.9 mmol) of 4-(3-phenylquinoxalin-2-yl)phenylboronic acid, 1.1 g (7.7 mmol) of potassium carbonate, 35 mL of toluene, 4 mL of ethanol, and 4 mL of water. The mixture was degassed by being stirred under reduced pressure, and the air in the flask was replaced with nitrogen.

To the mixture was added 79 mg (0.35 mmol) of palladium(II) acetate, and the mixture was stirred under a nitrogen stream at 80° C. for 9 hours. After the stirring, water was added to the mixture, followed by extraction of an organic substance from an aqueous layer with toluene. The obtained solution of the extract and an organic layer were combined, washed with brine, and drying with magnesium sulfate was performed. The mixture was gravity filtered, and the filtrate was concentrated to give an oily substance. The obtained oily substance was purified by silica gel column chromatography (toluene:ethyl acetate=9:1) to give a solid. The obtained solid was purified by high performance liquid chromatography (chloroform) to give a solid. Methanol was added to the obtained solid, followed by irradiation with ultrasonic waves. The precipitated solid was collected to give 0.95 g of a target pale yellow solid in a yield of 53%. Synthesis Scheme (b-1) is shown below.

[Chemical Formulae 32]

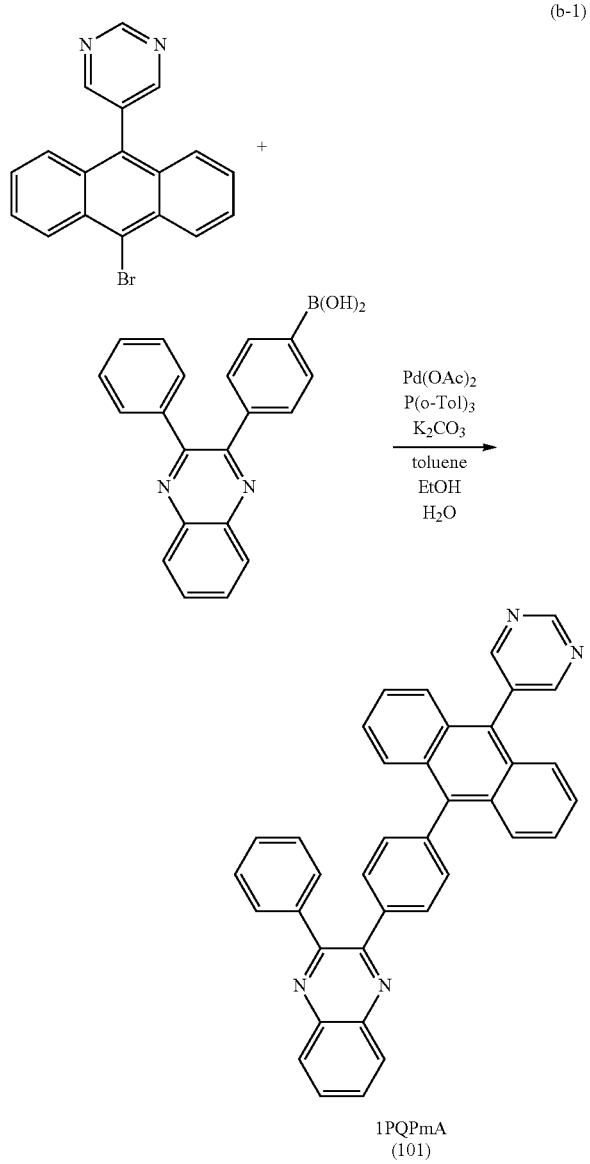

By a train sublimation method, 0.93 g of the obtained pale yellow solid was purified. The sublimation purification was performed under the conditions of reduced pressure and the argon flow rate being 5.0 mL/min, by heating at 235° C. for 15 hours. After the purification, 0.86 g of a target pale yellow solid was obtained at a collection rate of 92%.

Figure 19:
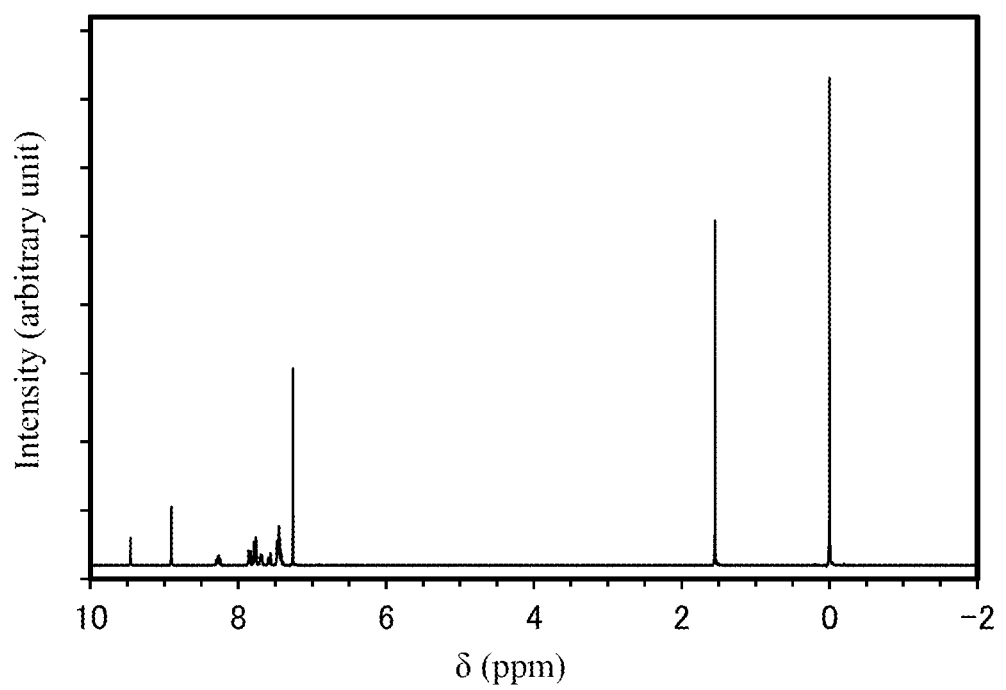
FIG. 19 shows a $^1$H-NMR chart of an organic compound represented by Structural Formula (101).

Analysis results by nuclear magnetic resonance ($^1$H-NMR) spectroscopy of the pale yellow solid obtained by the above reaction are shown below. A $^1$H-NMR chart is shown in FIG. 19. These results reveal that 1PQPmA, the organic compound of one embodiment of the present invention represented by Structural Formula (101), was obtained in this example.

$^1$H NMR (CDCl3, 300 MHz): δ=7.39-7.48 (m, 9H), 7.55-7.61 (m, 2H), 7.68-7.71 (m, 2H), 7.74-7.79 (m, 4H), 7.83-7.88 (m, 2H), 8.24-8.30 (m, 2H), 8.91 (s, 2H), 9.46 (s, 1H).

<<Physical Properties of 1PQPmA>>

Next, ultraviolet-visible absorption spectra (hereinafter simply referred to as "absorption spectra") and emission spectra of 1PQPmA in a toluene solution and a solid thin film of 1PQPmA were measured.

Figure 20:
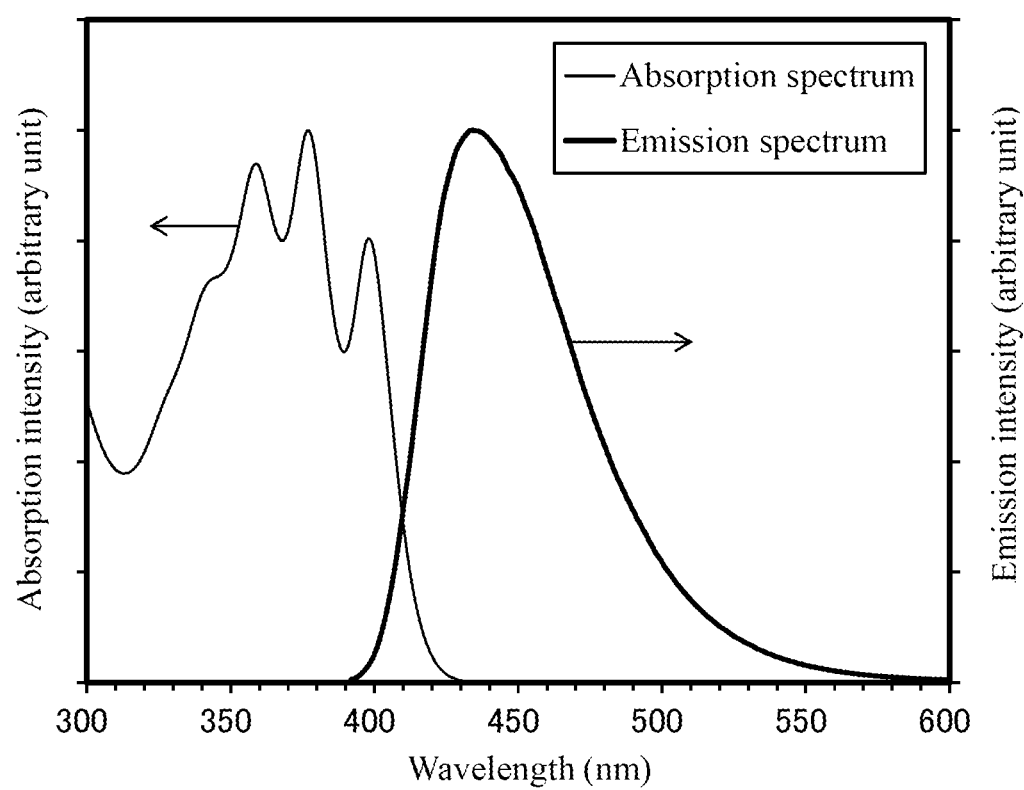
FIG. 20 shows the ultraviolet-visible absorption and emission spectra of an organic compound represented by Structural Formula (101).

The absorption spectrum of 1PQPmA in the toluene solution was measured using an ultraviolet-visible spectrophotometer (V-550, produced by JASCO Corporation). The emission spectrum of 1PQPmA in the toluene solution was measured using a fluorescence spectrophotometer (FP-8600, produced by JASCO Corporation). Note that the absorption spectrum of 1PQPmA in the toluene solution was calculated by subtraction of the measured absorption spectrum of only toluene in a quartz cell. FIG. 20 shows the obtained absorption and emission spectra of 1PQPmA in the toluene solution. The horizontal axis represents wavelength and the vertical axes represent absorption intensity and emission intensity.

From the results in FIG. 20, for the toluene solution of 1PQPmA, absorption peaks were observed at around 359 nm, 377 nm, and 398 nm, and an emission wavelength peak was observed at around 434 nm (excitation wavelength: 377 nm).

Figure 21:
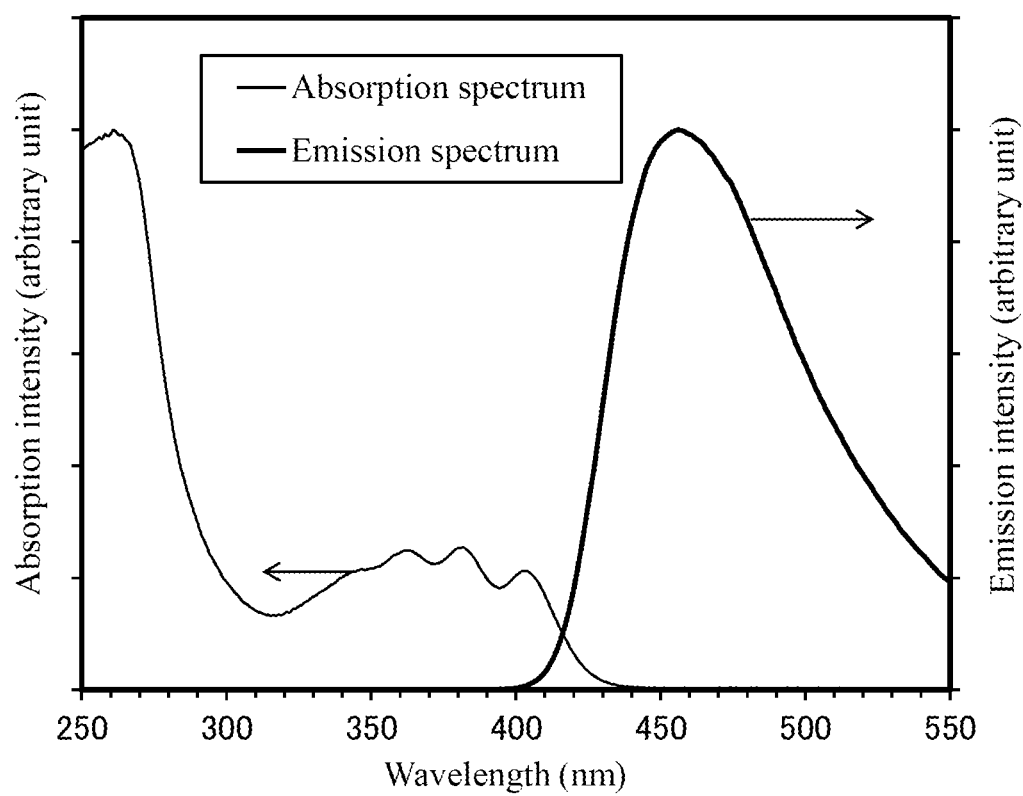
FIG. 21 shows the ultraviolet-visible absorption and emission spectra of an organic compound represented by Structural Formula (101).

The solid thin film of 1PQPmA was fabricated over a quartz substrate by a vacuum evaporation method. The absorption spectrum of the solid thin film was measured using an ultraviolet-visible spectrophotometer (V-550, produced by JASCO Corporation). The emission spectrum of the solid thin film was measured using a fluorescence spectrophotometer (FP-8600, produced by JASCO Corporation). Note that the absorption spectrum of the solid thin film was calculated by subtraction of the absorption spectrum of the quartz substrate. FIG. 21 shows the obtained absorption and emission spectra of the solid thin film of 1PQPmA. The horizontal axis represents wavelength and the vertical axes represent absorption intensity and emission intensity.

From the results in FIG. 21, for the solid thin film of 1PQPmA, absorption peaks were observed at around 362 nm, 382 nm, and 403 nm, and an emission wavelength peak was observed at around 456 nm (excitation wavelength: 380 nm).

The results reveal that 1PQPmA emits blue light. Moreover, 1PQPmA, the compound of one embodiment of the present invention, can be used as a host for a light-emitting substance or a substance which emits fluorescence in the visible region.

Example 4

Synthesis Example 3

This example will describe a method for synthesizing 2-phenyl-3-[10-(pyrazin-2-yl)-9-anthryl]quinoxaline (abbreviation: 1PQPrA), the organic compound of one embodiment of the present invention represented by Structural Formula (102) in Embodiment 1. The structure of 1PQPrA is shown below.

[Chemical Formula 33]

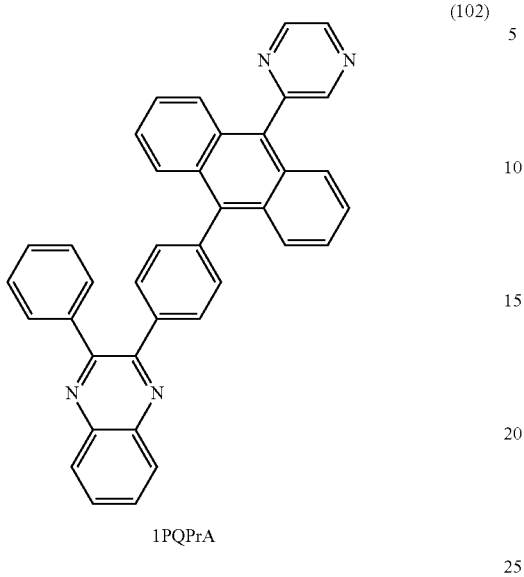

1PQPrA (102)

Into a 200 mL three-neck flask were added 0.58 g (1.7 mmol) of 2-(10-bromo-9-anthryl)pyrazine, 0.62 g (1.9 mmol) of 4-(3-phenylquinoxalin-2-yl)phenylboronic acid, 0.47 g (3.4 mmol) of potassium carbonate, 20 mL of toluene, 4 mL of ethanol, and 2 mL of water. The mixture was degassed by being stirred under reduced pressure, and the air in the flask was replaced with nitrogen.

To the mixture in the flask was added 0.10 g (0.34 mmol) of tri(ortho-tolyl)phosphine and 15 mg (68 μmol) of palladium(II) acetate, and the mixture was stirred under a nitrogen stream at 80° C. for 19 hours. After the stirring, water was added to the mixture, followed by extraction of an organic substance from an aqueous layer with toluene. The obtained solution of the extract and an organic layer were combined, washed with brine, and drying with magnesium sulfate was performed. The mixture was gravity filtered, and the filtrate was concentrated to give an oily substance. The obtained oily substance was purified by silica gel column chromatography (ethyl acetate; hexane=1:2) and recrystallized with toluene/hexane, giving 0.47 g of a target yellow solid in a yield of 52%. Synthesis Scheme (c-1) is shown below.

[Chemical Formulae 34]

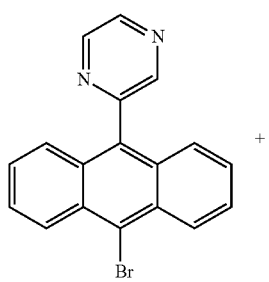

+

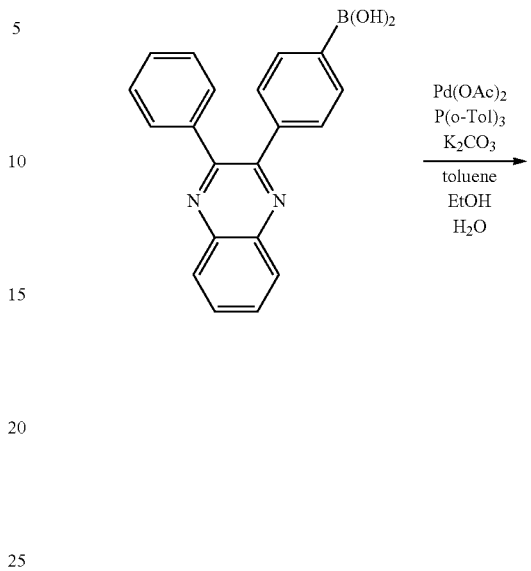

(c-1)

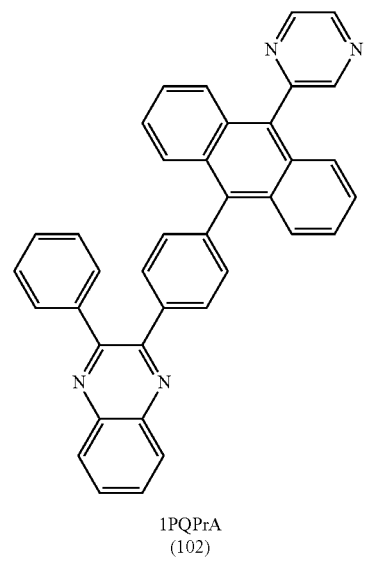

1PQPrA (102)

By a train sublimation method, 0.46 g of the obtained yellow solid was purified. The sublimation purification was performed under the conditions of the pressure being 3.1 Pa and the argon flow rate being 5.0 mL/min, by heating at 250° C. for 18 hours. After the purification, 0.37 g of a target yellow solid was obtained at a collection rate of 80%.

Figure 22:
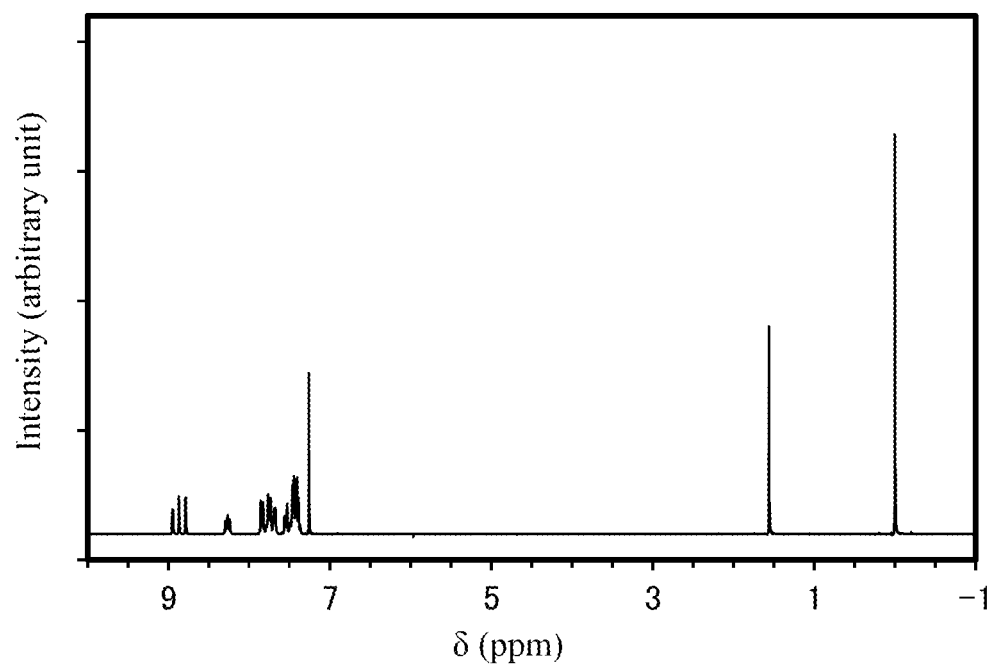
FIG. 22 shows a $^1$H-NMR chart of an organic compound represented by Structural Formula (102).

Analysis results by nuclear magnetic resonance ($^1$H-NMR) spectroscopy of the yellow solid obtained by the above reaction are shown below. A $^1$H-NMR chart is shown in FIG. 22. These results reveal that 1PQPrA, the organic compound of one embodiment of the present invention represented by Structural Formula (102), was obtained in this example.

$^1$H NMR (CDCl3, 300 MHz): δ=7.38-7.56 (m, 11H), 7.67-7.86 (m, 8H), 8.24-8.30 (m, 2H), 8.79 (d, 1H), 8.87 (d, 1H), 8.94-8.96 (m, 1H).

<<Physical Properties of 1PQPrA>>

Next, ultraviolet-visible absorption spectra (hereinafter simply referred to as "absorption spectra") and emission spectra of 1PQPrA in a toluene solution and a solid thin film of 1PQPrA were measured.

Figure 23:
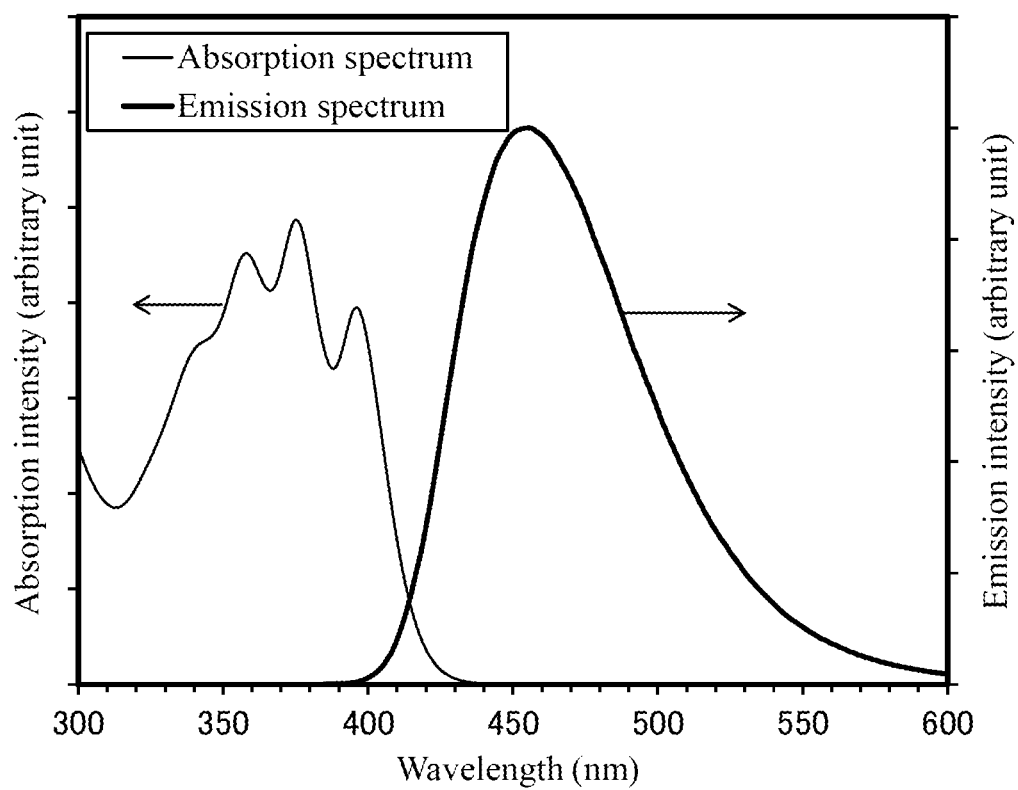
FIG. 23 shows the ultraviolet-visible absorption and emission spectra of an organic compound represented by Structural Formula (102).

The absorption spectrum of 1PQPrA in the toluene solution was measured using an ultraviolet-visible spectrophotometer (V-550, produced by JASCO Corporation). The emission spectrum of 1PQPrA in the toluene solution was measured using a fluorescence spectrophotometer (FP-8600, produced by JASCO Corporation). Note that the absorption spectrum of 1PQPrA in the toluene solution was calculated by subtraction of the measured absorption spectrum of only toluene in a quartz cell. FIG. 23 shows the obtained absorption and emission spectra of 1PQPrA in the toluene solution. The horizontal axis represents wavelength and the vertical axes represent absorption intensity and emission intensity.

From the results in FIG. 23, for the toluene solution of 1PQPrA, absorption peaks were observed at around 358 nm, 375 nm, and 396 nm, and an emission wavelength peak was observed at around 455 nm (excitation wavelength: 375 nm).

Figure 24:
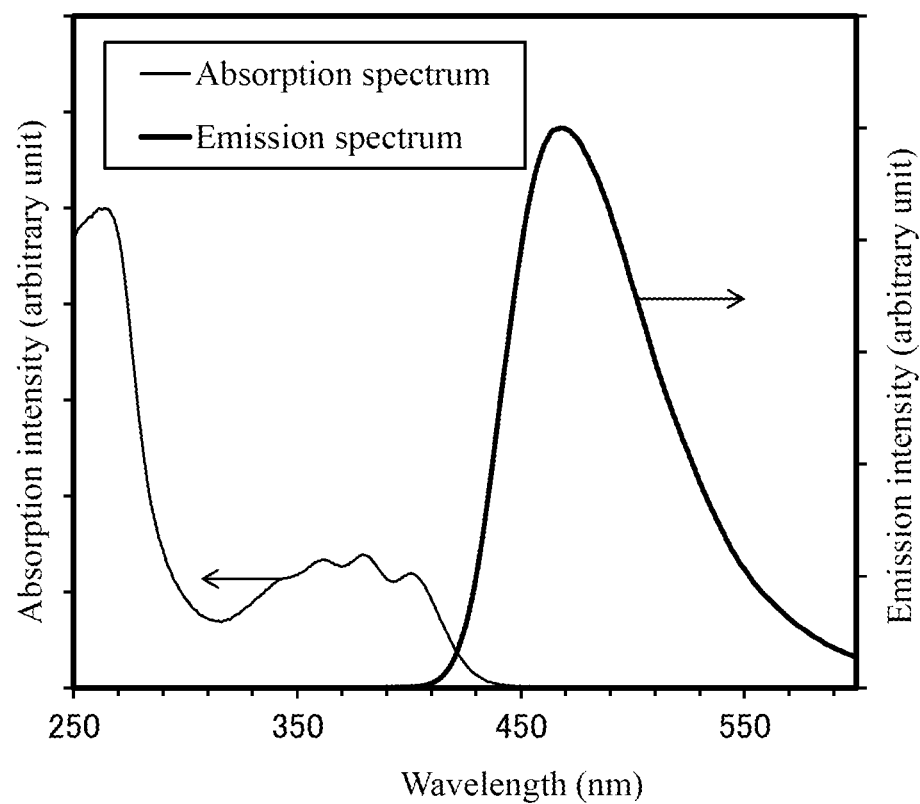
FIG. 24 shows the ultraviolet-visible absorption and emission spectra of an organic compound represented by Structural Formula (102).

The solid thin film of 1PQPrA was fabricated over a quartz substrate by a vacuum evaporation method. The absorption spectrum of the solid thin film was measured using an ultraviolet-visible spectrophotometer (V-550, produced by JASCO Corporation). The emission spectrum of the solid thin film was measured using a fluorescence spectrophotometer (FP-8600, produced by JASCO Corporation). Note that the absorption spectrum of the solid thin film was calculated by subtraction of the absorption spectrum of the quartz substrate. FIG. 24 shows the obtained absorption and emission spectra of the solid thin film of 1PQPrA. The horizontal axis represents wavelength and the vertical axes represent absorption intensity and emission intensity.

From the results in FIG. 24, for the solid thin film of 1PQPrA, absorption peaks were observed at around 362 nm, 380 nm, and 401 nm, and an emission wavelength peak was observed at around 468 nm (excitation wavelength: 360 nm).

The results reveal that 1PQPrA emits blue light. Moreover, 1PQPrA, the compound of one embodiment of the present invention, can be used as a host for a light-emitting substance or a substance which emits fluorescence in the visible region.

Example 5

Synthesis Example 4

This example will describe a method for synthesizing 2-phenyl-3-(4-{10-[4-(3-pyridyl)phenyl]-9-anthryl}phenyl)quinoxaline (abbreviation: 1PQPyPA), the organic compound of one embodiment of the present invention represented by Structural Formula (135) in Embodiment 1. The structure of 1PQPyPA is shown below.

[Chemical Formula 35]

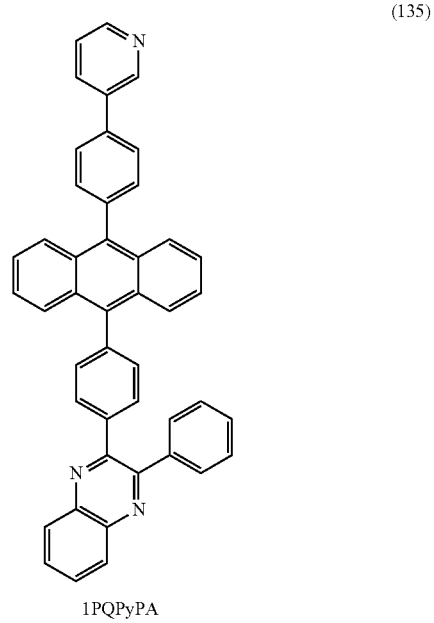

(135)

1PQPyPA

Into a 200 mL three-neck flask were added 1.8 g (4.4 mmol) of 3-[4-(10-bromo-9-anthryl)phenyl]pyridine, 1.6 g (4.8 mmol) of 4-(3-phenylquinoxalin-2-yl)phenylboronic acid, 1.2 g (8.8 mmol) of potassium carbonate, 50 mL of toluene, 10 mL of ethanol, and 5 mL of water. The mixture was degassed by being stirred under reduced pressure, and the air in the flask was replaced with nitrogen.

To the mixture in the flask were added 0.13 g (0.44 mmol) of tri(ortho-tolyl)phosphine and 20 mg (88 μmol) of palladium(II) acetate, and the mixture was stirred under a nitrogen stream at 80° C. for 20 hours. After the stirring, the precipitated solid was filtered and the collected solid and filtrate were purified separately. First, the obtained solid was dissolved in chloroform, and an insoluble matter was removed by filtration. Then, the filtrate was concentrated and purified by silica gel column chromatography (toluene:ethyl acetate=1:1).

Next, an organic substance was extracted from the filtrate with toluene and the solution of the extract and an organic layer were combined and drying with magnesium sulfate was performed. The mixture was gravity filtered, and the filtrate was concentrated and purified by silica gel column chromatography (hexane:ethyl acetate=2:1). The solids obtained through purification operations were recrystallized with toluene/hexane to give 2.1 g of a target pale yellow solid in a yield of 78%. Synthesis Scheme (d-1) is shown below.

[Chemical Formulae 36]

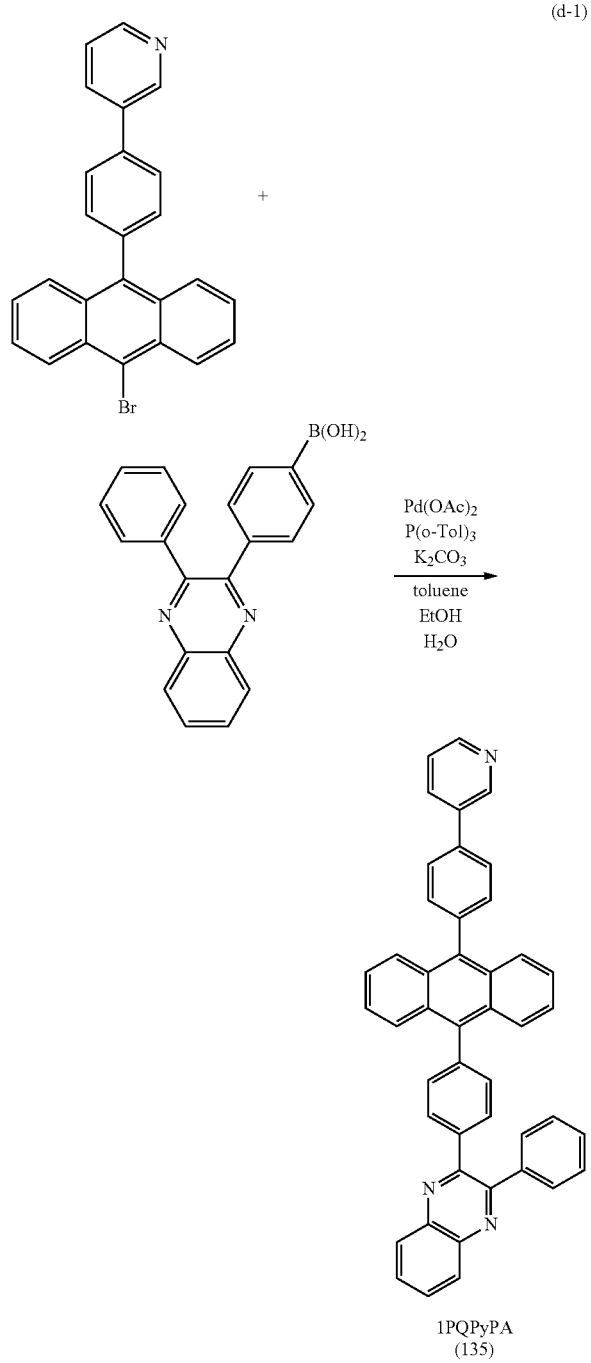

By a train sublimation method, 2.1 g of the obtained pale yellow solid was purified. The sublimation purification was performed under the conditions of the pressure being 6.2 Pa and the argon flow rate being 10 mL/min, by heating at 260° C. for 19 hours. After the purification, 1.8 g of a target pale yellow solid was obtained at a collection rate of 88%.

Figure 25:
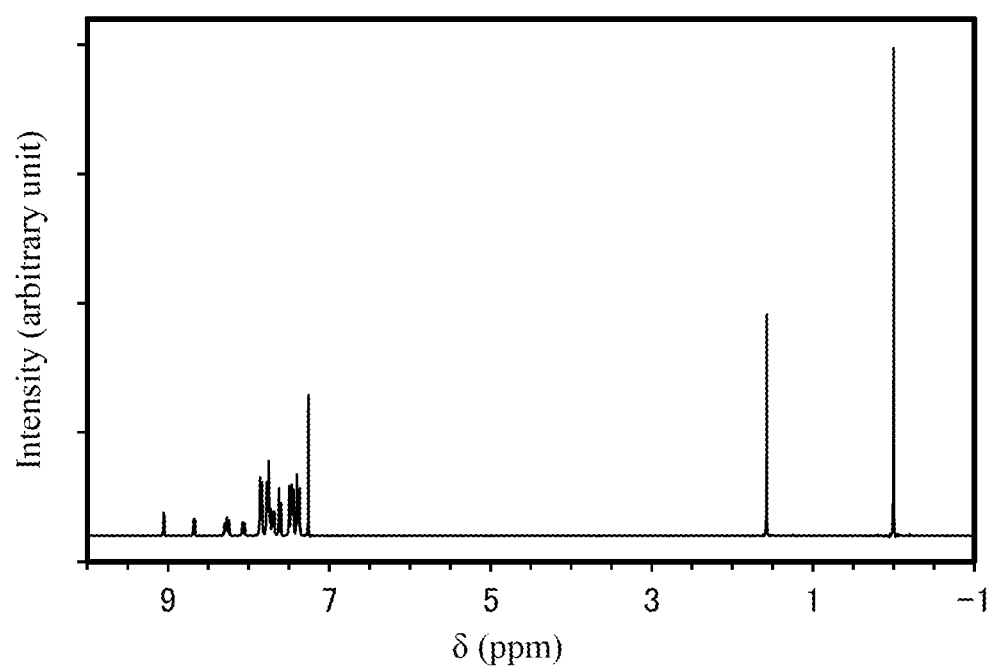
FIG. 25 shows a chart of an organic compound represented by Structural Formula (135).

Analysis results by nuclear magnetic resonance ($^1$H-NMR) spectroscopy of the pale yellow solid obtained by the above reaction are shown below. A $^1$H-NMR chart is shown in FIG. 25. These results reveal that 1PQPyPA, the organic compound of one embodiment of the present invention represented by Structural Formula (135), was obtained in this example.

$^1$H NMR (CDCl3, 300 MHz): δ=7.36-7.50 (m, 10H), 7.60 (d, 2H), 7.68-7.78 (m, 8H), 7.83-7.86 (m, 4H), 8.06 (d, 1H), 8.24-8.30 (m, 2H), 8.67 (d, 1H), 9.05 (d, 1H).

<<Physical Properties of 1PQPyPA>>

Next, ultraviolet-visible absorption spectra (hereinafter simply referred to as "absorption spectra") and emission spectra of 1PQPyPA in a toluene solution and a solid thin film of 1PQPyPA were measured.

Figure 26:
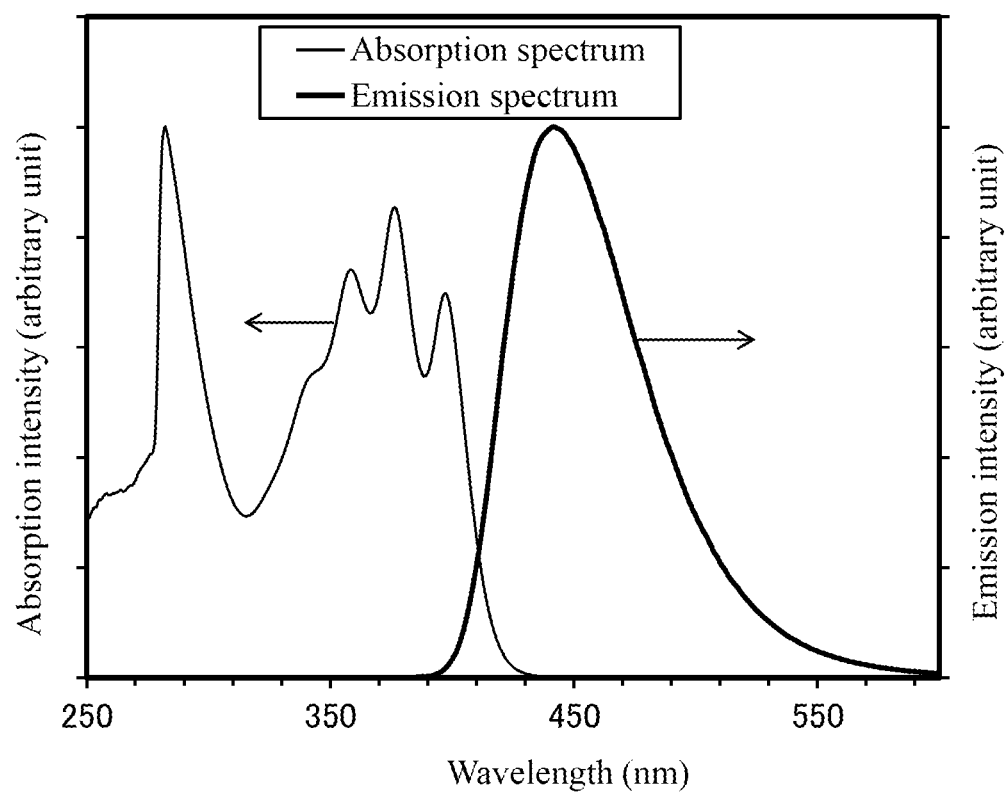
FIG. 26 shows the ultraviolet-visible absorption and emission spectra of an organic compound represented by Structural Formula (135).

The absorption spectrum of 1PQPyPA in the toluene solution was measured using an ultraviolet-visible spectrophotometer (V-550, produced by JASCO Corporation). The emission spectrum of 1PQPyPA in the toluene solution was measured using a fluorescence spectrophotometer (FP-8600, produced by JASCO Corporation). Note that the absorption spectrum of 1PQPyPA in the toluene solution was calculated by subtraction of the measured absorption spectrum of only toluene in a quartz cell. FIG. 26 shows the obtained absorption and emission spectra of 1PQPyPA in the toluene solution. The horizontal axis represents wavelength and the vertical axes represent absorption intensity and emission intensity.

From the results in FIG. 26, for the toluene solution of 1PQPyPA, absorption peaks were observed at around 358 nm, 376 nm, and 397 nm, and an emission wavelength peak was observed at around 442 nm (excitation wavelength: 375 nm).

Figure 27:
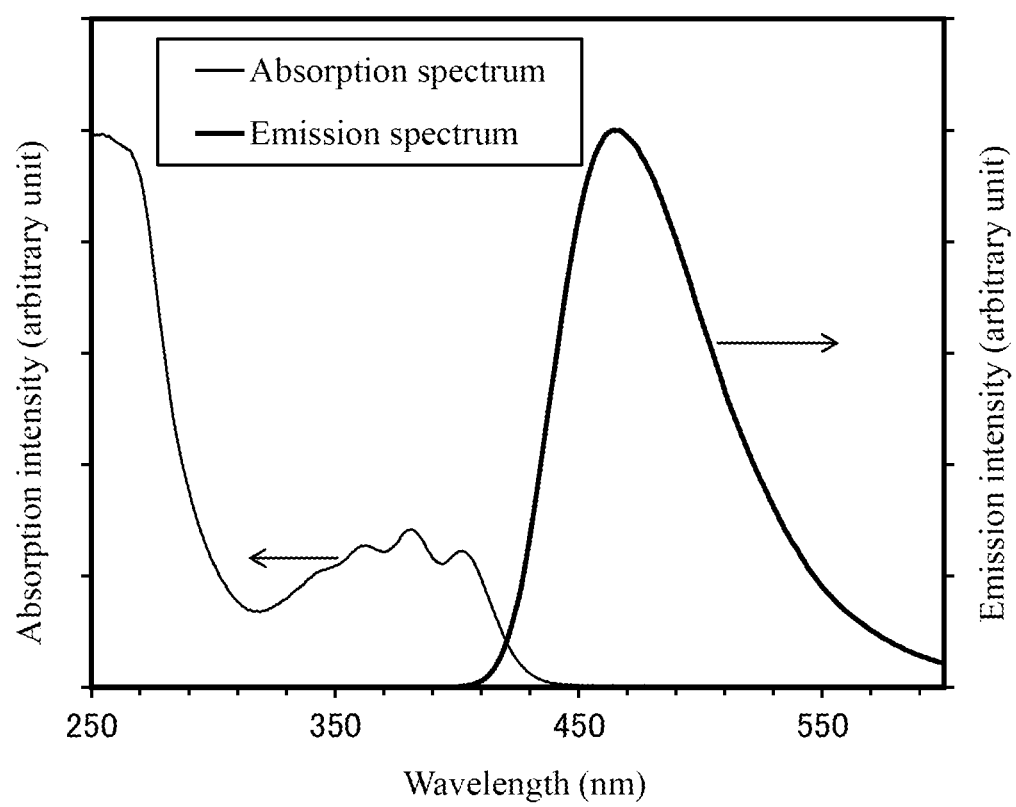
FIG. 27 shows the ultraviolet-visible absorption and emission spectra of an organic compound represented by Structural Formula (135).

The solid thin film of 1PQPyPA was fabricated over a quartz substrate by a vacuum evaporation method. The absorption spectrum of the solid thin film was measured using an ultraviolet-visible spectrophotometer (V-550, produced by JASCO Corporation). The emission spectrum of the solid thin film was measured using a fluorescence spectrophotometer (FP-8600, produced by JASCO Corporation). Note that the absorption spectrum of the solid thin film was calculated by subtraction of the absorption spectrum of the quartz substrate. FIG. 27 shows the obtained absorption and emission spectra of the solid thin film of 1PQPyPA. The horizontal axis represents wavelength and the vertical axes represent absorption intensity and emission intensity.

From the results in FIG. 27, for the solid thin film of 1PQPyPA, absorption peaks were observed at around 362 nm, 382 nm, and 402 nm, and an emission wavelength peak was observed at around 464 nm (excitation wavelength: 360 nm).

The results reveal that 1PQPyPA emits blue light. Moreover, 1PQPyPA, the compound of one embodiment of the present invention, can be used as a host for a light-emitting substance or a substance which emits fluorescence in the visible region.

Example 6

Synthesis Example 5

This example will describe a method for synthesizing 2-phenyl-3-{4-[10-(5-phenyl-3-pyridyl)-9-anthryl]phenyl}quinoxaline (abbreviation: 1PQmPPyA), the organic compound of one embodiment of the present invention represented by Structural Formula (147) in Embodiment 1. The structure of 1PQmPPyA is shown below.

[Chemical Formula 37]

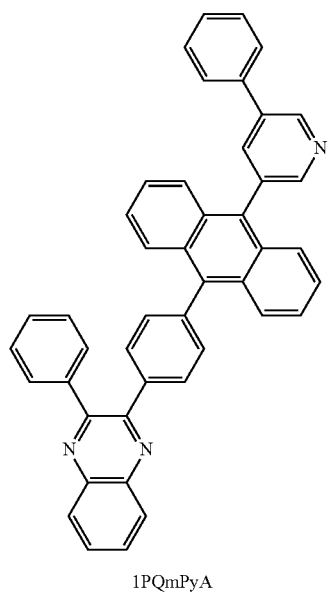

(147)

1PQmPyA

Step 1: Synthesis of 3-(9-anthryl)-5-phenylpyridine

Into a 200 mL three-neck flask were added 1.0 g (4.3 mmol) of 3-bromo-5-phenylpyridine, 2.0 g (9.2 mmol) of 9-anthraceneboronic acid, and 2.4 g (17 mmol) of potassium carbonate, and the air in the flask was replaced with nitrogen. Into the mixture were added 40 mL of tetrahydrofuran and 8 mL of water, and the mixture was degassed by being stirred under reduced pressure. Into the mixture were added 0.10 g (0.35 mmol) of tri-tert-butylphosphoniumtetrafluoroborate and 98 mg (0.11 mmol) of tris(dibenzylideneacetone)dipalladium(0), and the mixture was stirred under a nitrogen stream at 80° C. for 14 hours.

After the stirring, water was added to the mixture, followed by extraction of an aqueous layer with toluene. The obtained solution of the extract and an organic layer were combined and washed with water and brine, and an organic layer was dried with magnesium sulfate. The mixture was gravity filtered, and the filtrate was concentrated to give a solid. The solid was purified by silica gel column chromatography (toluene:ethyl acetate=9:1) and recrystallized with methanol to give 1.4 g of a target white solid in a yield of 98%. Synthesis Scheme (e-1) is shown below.

[Compound Formulae 38]

(e-1)

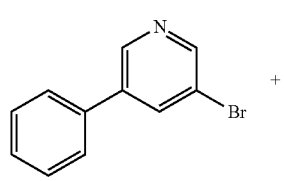

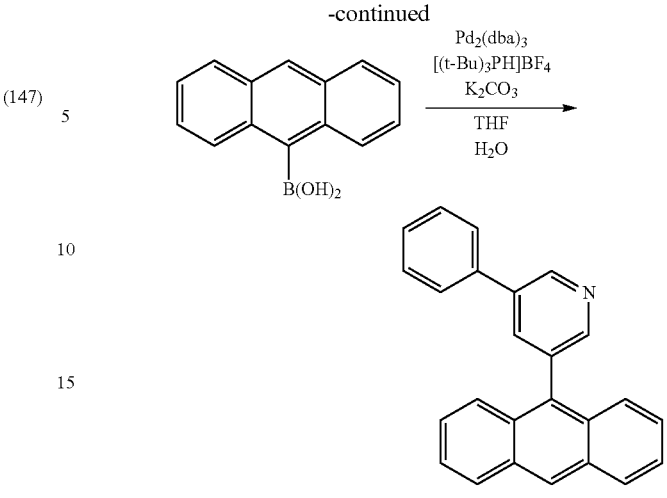

<Step 2: Synthesis of 3-(10-bromo-9-anthryl)-5-phenylpyridine>

Into a 200 mL recovery flask were added 1.4 g (4.2 mmol) of 3-(9-anthryl)-5-phenylpyridine, 40 mL of dimethylformamide, and 0.82 g (4.6 mmol) of N-bromosuccinimide, and the mixture was stirred at room temperature for 45 hours.

After the stirring, water was added to the mixture, the mixture was suction-filtered through Celite, and an aqueous layer was extracted with toluene. The obtained solution of the extract and an organic layer were combined and washed with an aqueous solution of sodium thiosulfate, an aqueous solution of sodium hydrogen carbonate, and brine, and an organic layer was dried with magnesium sulfate. The mixture was gravity filtered, and the filtrate was concentrated to give an oily substance. The oily substance was purified by silica gel column chromatography (toluene:ethyl acetate=19:1) to give 1.1 g of a target solid in a yield of 65%. Synthesis Scheme (e-2) is shown below.

[Chemical Formulae 39]

(e-2)

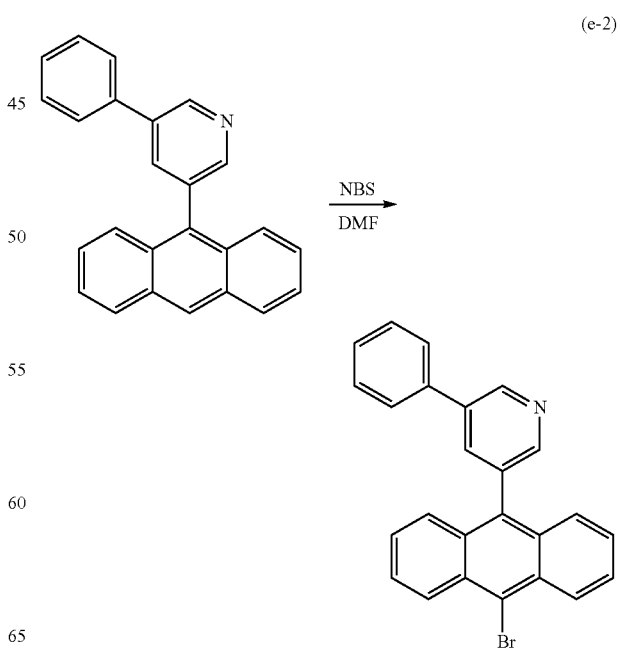

<Step 3: Synthesis of 1PQmPPyA>

Into a 100 mL three-neck flask were added 1.1 g (2.7 mmol) of 3-(10-bromo-9-anthryl)-5-phenylpyridine, 0.98 g (3.0 mmol) of 4-(3-phenylquinoxalin-2-yl)phenylboronic acid, 83 mg (0.27 mmol) of tri(ortho-tolyl)phosphine, and 0.76 g (5.5 mmol) of potassium carbonate, and the air in the flask was replaced with nitrogen. Into the mixture were added 25 mL of toluene, 5.0 mL of ethanol, and 2.5 mL of water, and the mixture was degassed by being stirred under reduced pressure. Into the mixture were added 12 mg (55 µmol) of palladium(II) acetate, and the mixture was stirred under a nitrogen stream at 80° C. for 25 hours.

After the stirring, water was added to the mixture, followed by extraction of an aqueous layer with toluene. The obtained solution of the extract and an organic layer were combined and washed with water and brine, and an organic layer was dried with magnesium sulfate. The mixture was gravity filtered, and the filtrate was concentrated to give a solid. The solid was purified by silica gel column chromatography (toluene:ethyl acetate=19:1) and recrystallized with ethyl acetate/hexane to give 0.85 g of a target pale yellow solid in a yield of 51%. Synthesis Scheme (e-3) is shown below.

[Chemical Formulae 40]

By a train sublimation method, 0.87 g of the obtained pale yellow solid was purified. The sublimation purification was performed under the conditions of the pressure being 4.5 Pa and the argon flow rate being 15.0 mL/min, by heating at 310° C. for 16 hours. After the purification, 0.50 g of a target pale yellow solid was obtained at a collection rate of 57%.

Figure 28:
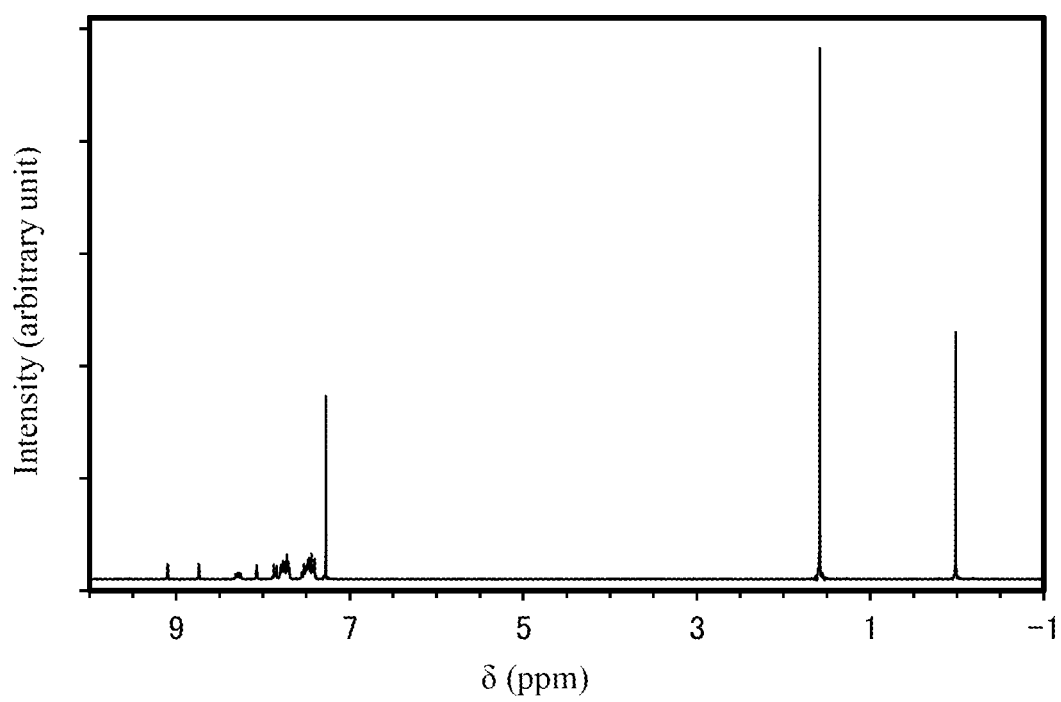
FIG. 28 shows a chart of an organic compound represented by Structural Formula (147).

Analysis results by nuclear magnetic resonance ($^1$H-NMR) spectroscopy of the pale yellow solid obtained by the above reaction are shown below. A $^1$H-NMR chart is shown in FIG. 28. These results reveal that 1PQmPPyA, the organic compound of one embodiment of the present invention represented by Structural Formula (147), was obtained in this example.

$^1$H NMR (CDCl3, 300 MHz): δ=7.38-7.57 (m, 12H), 7.67-7.82 (m, 10H), 7.83-7.90 (m, 2H), 8.07 (t, J=2, 1 Hz, 1H), 8.24-8.34 (m, 2H), 8.74 (d, J=1, 8 Hz, 1H), 9.10 (d, J=2.1 Hz, 1H).

<<Physical Properties of 1PQmPPyA>>

Next, ultraviolet-visible absorption spectra (hereinafter simply referred to as "absorption spectra") and emission spectra of 1PQmPPyA in a toluene solution and a solid thin film of 1PQmPPyA were measured.

Figure 29:
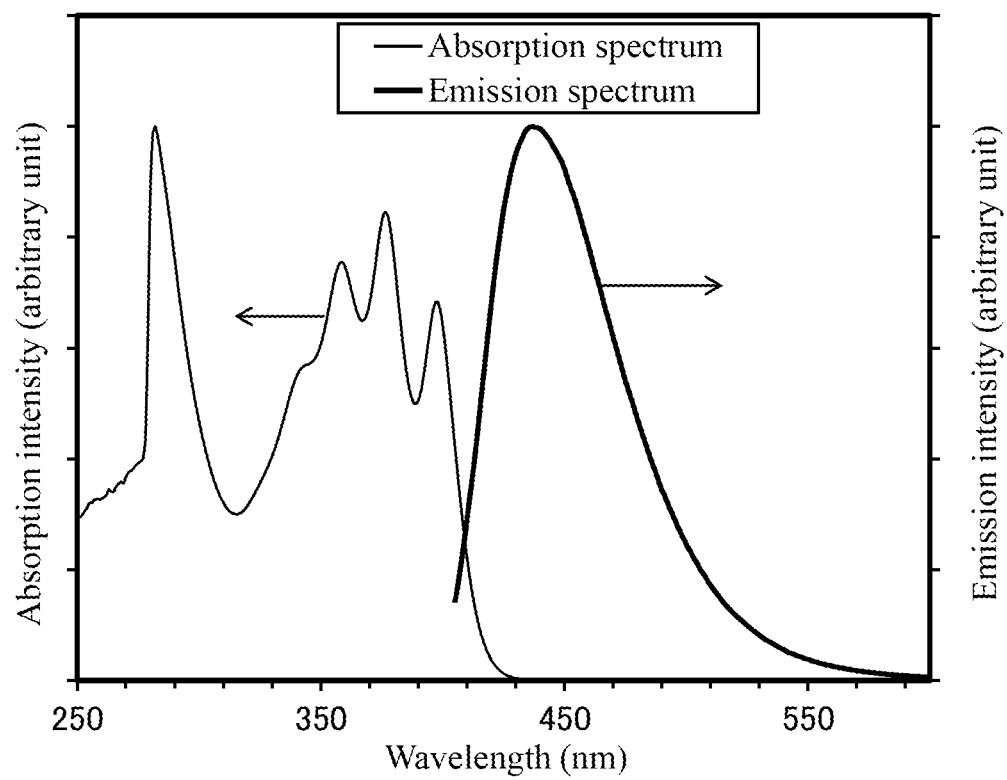
FIG. 29 shows the ultraviolet-visible absorption and emission spectra of an organic compound represented by Structural Formula (147).

The absorption spectrum of 1PQmPPyA in the toluene solution was measured using an ultraviolet-visible spectrophotometer (V-550, produced by JASCO Corporation). The emission spectrum of 1PQmPPyA in the toluene solution was measured using a fluorescence spectrophotometer (FP-8600, produced by JASCO Corporation). Note that the absorption spectrum of 1PQmPPyA in the toluene solution was calculated by subtraction of the measured absorption spectrum of only toluene in a quartz cell. FIG. 29 shows the obtained absorption and emission spectra of 1PQmPPyA in the toluene solution. The horizontal axis represents wavelength and the vertical axes represent absorption intensity and emission intensity.

From the results in FIG. 29, for the toluene solution of 1PQmPPyA, absorption peaks were observed at around 358 nm, 377 nm, and 398 nm, and an emission wavelength peak was observed at around 437 nm (excitation wavelength: 398 nm).

Figure 30:
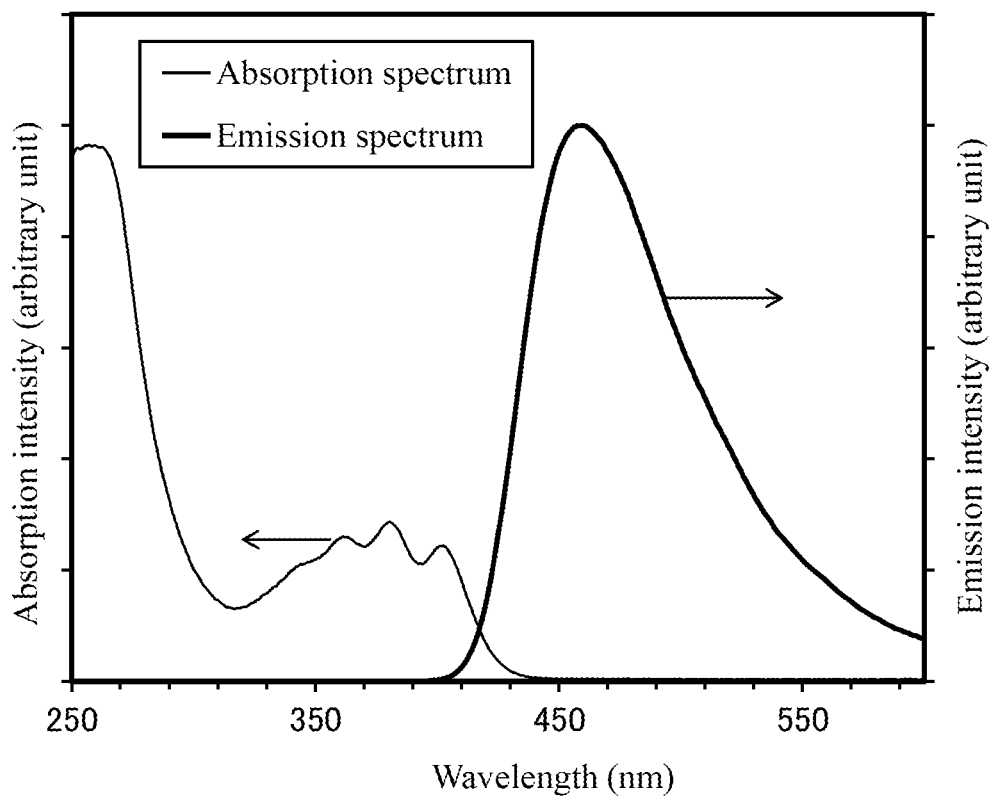
FIG. 30 shows the ultraviolet-visible absorption and emission spectra of an organic compound represented by Structural Formula (147).

The solid thin film of 1PQmPPyA was fabricated over a quartz substrate by a vacuum evaporation method. The absorption spectrum of the solid thin film was measured using an ultraviolet-visible spectrophotometer (V-550, produced by JASCO Corporation). The emission spectrum of the solid thin film was measured using a fluorescence spectrophotometer (FP-8600, produced by JASCO Corporation). Note that the absorption spectrum of the solid thin film was calculated by subtraction of the absorption spectrum of the quartz substrate. FIG. 30 shows the obtained absorption and emission spectra of the solid thin film of 1PQmPPyA. The horizontal axis represents wavelength and the vertical axes represent absorption intensity and emission intensity.

From the results in FIG. 30, for the solid thin film of 1PQmPPyA, absorption peaks were observed at around 363 nm, 381 nm, and 402 nm, and an emission wavelength peak was observed at around 460 nm (excitation wavelength: 360 nm).

The results reveal that 1PQmPPyA emits blue light. Moreover, 1PQmPPyA, the compound of one embodiment of the present invention, can be used as a host for a light-emitting substance or a substance which emits fluorescence in the visible region.

Example 7

Synthesis Example 6

This example will describe a method for synthesizing 2-phenyl-3-{4-[10-(2,6-dimethyl-3-pyridyl)-9-anthryl]phenyl}quinoxaline (abbreviation: 1PQDMePyA), the organic compound of one embodiment of the present invention represented by Structural Formula (175) in Embodiment 1. The structure of 1PQDMePyA is shown below.

[Chemical Formula 41]

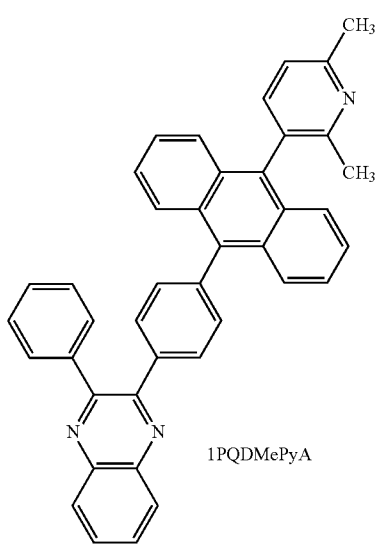

1PQDMePyA (175)

Step 1: Synthesis of 3-(9-anthryl)-2,6-dimethylpyridine

Into a 300 mL three-neck flask were added 2.4 g (13 mmol) of 2,6-dimethyl-3-bromopyridine, 3.2 g (14 mmol) of 9-anthraceneboronic acid, and 7.2 g (52 mmol) of potassium carbonate, and the air in the flask was replaced with nitrogen. Into the mixture were added 130 mL of THF and 26 mL of water, and the mixture was degassed by being stirred under reduced pressure. Into the mixture were added 0.11 g (0.39 mmol) of tri-tert-butylphosphoniumtetrafluoroborate and 0.12 g (0.13 mmol) of tris(dibenzylideneacetone)dipalladium(0), and the mixture was stirred under a nitrogen stream at 80° C. for 11 hours.

After the stirring, water was added to the mixture, followed by extraction of an aqueous layer with toluene. The obtained solution of the extract and an organic layer were combined and washed with water and brine, and an organic layer was dried with magnesium sulfate. The mixture was gravity filtered, and the filtrate was concentrated to give a solid. The solid was purified by silica gel column chromatography (toluene:ethyl acetate=9:1) to give 3.4 g of a target white solid in a yield of 92%. Synthesis Scheme (f-1) is shown below.

[Chemical Formulae 42]

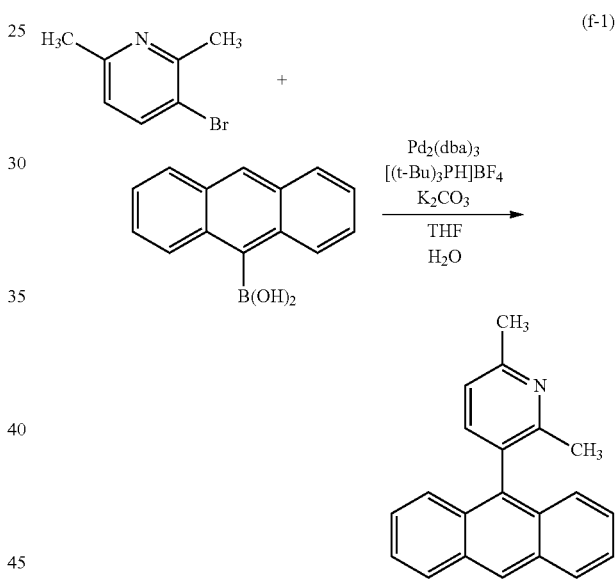

(f-1)

<Step 2: Synthesis of 3-(10-bromo-9-anthryl)-2,6-dimethylpyridine>

Into a 300 mL recovery flask were added 2.7 g (9.4 mmol) of 3-(9-anthryl)-2,6-dimethylpyridine and 100 mL of DMF, and the mixture was stirred at 0° C. Into the mixture was added 1.8 g (10 mmol) of N-bromosuccinimide, the temperature of the mixture was raised to room temperature, and the mixture was stirred for 66 hours. After the stirring, water was added to the mixture, the mixture was suction-filtered through Celite, and an aqueous layer was extracted with toluene. The obtained solution of the extract and an organic layer were combined and washed with an aqueous solution of sodium thiosulfate, an aqueous solution of sodium hydrogen carbonate, and brine, and an organic layer was dried with magnesium sulfate. The mixture was gravity filtered, and the filtrate was concentrated to give a solid. The solid was purified by silica gel column chromatography (toluene:ethyl acetate=19:1) to give 3.3 g of a target solid in a yield of 99%. Synthesis Scheme (f-2) is shown below.

[Chemical Formulae 43]

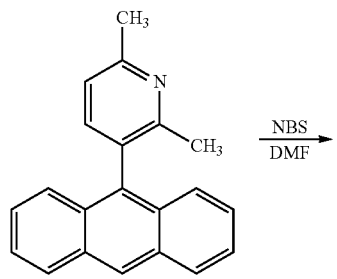

(f-2)

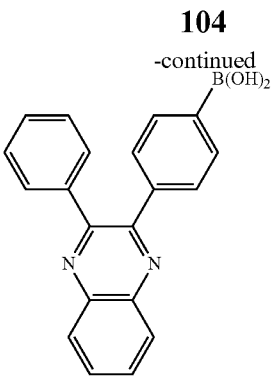

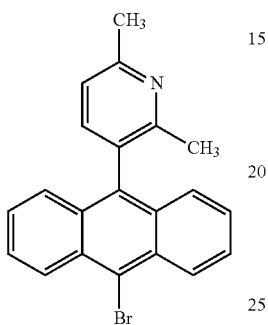

<Step 3: Synthesis of 1PQDMePyA>

Into a 100 mL three-neck flask were added 1.2 g (3.3 mmol) of 3-(10-bromo-9-anthryl)-2,6-dimethylpyridine, 1.2 g (3.7 mmol) of 4-(3-phenylquinoxalin-2-yl)phenylboronic acid, 98 mg (0.32 mmol) of tri(ortho-tolyl)phosphine, and 0.92 g (6.6 mmol) of potassium carbonate, and the air in the flask was replaced with nitrogen. Into the mixture were added 30 mL of toluene, 6.0 mL of ethanol, and 3.0 mL of water, and the mixture was degassed by being stirred under reduced pressure. Into the mixture were added 14.9 mg (66 µmol) of palladium(II) acetate, and the mixture was stirred under a nitrogen stream at 80° C. for 21 hours. After the stirring, water was added to the mixture, followed by extraction of an aqueous layer with toluene. The obtained solution of the extract and an organic layer were combined and washed with water and brine, and an organic layer was dried with magnesium sulfate. The mixture was gravity filtered, and the filtrate was concentrated to give a solid. The solid was purified by silica gel column chromatography (toluene:ethyl acetate=19:1) and recrystallized with toluene/methanol to give 1.4 g (2.5 mmol) of a target pale yellow solid in a yield of 75%. Synthesis Scheme (f-3) is shown below.

[Chemical Formulae 44]

(f-3)

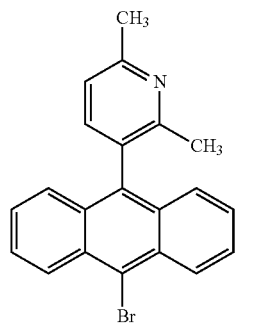

+

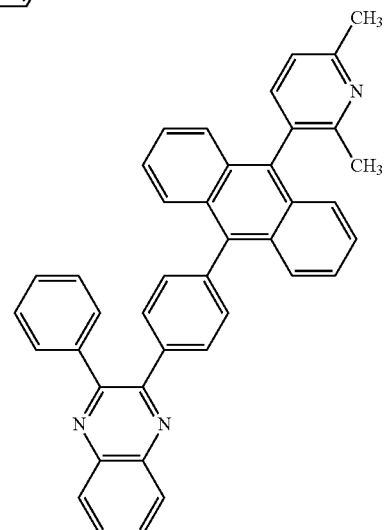

1PQDMePyA
(175)

By a train sublimation method, 1.4 g of the obtained pale yellow solid was purified. The sublimation purification was performed under the conditions of the pressure being 6.7 Pa and the argon flow rate being 5.0 mL/min, by heating at 250° C. for 16 hours. After the purification, 1.3 g of a target pale yellow solid was obtained at a collection rate of 92%.

Figure 31:
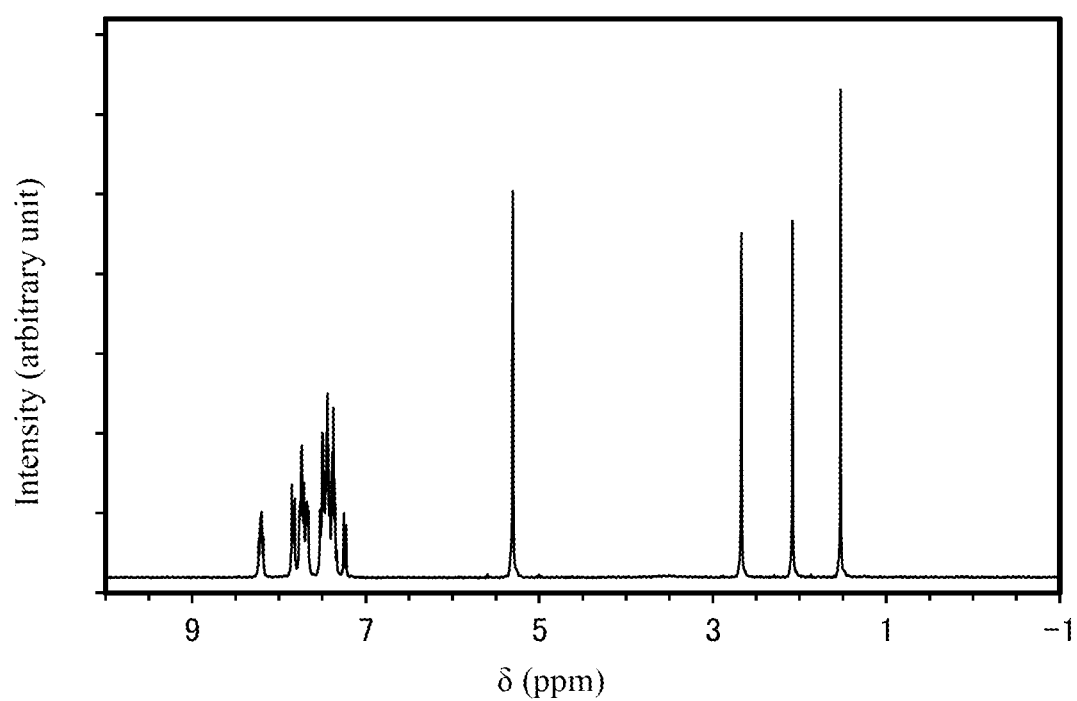
FIG. 31 shows a chart of an organic compound represented by Structural Formula (175).

Analysis results by nuclear magnetic resonance ($^1$H-NMR) spectroscopy of the pale yellow solid obtained by the above reaction are shown below. A $^1$H-NMR chart is shown in FIG. 31. These results reveal that 1PQDMePyA the organic compound of one embodiment of the present invention represented by Structural Formula (175), was obtained in this example.

$^1$H NMR (CD2Cl2, 300 MHz): δ=2.10 (s, 3H), 2.69 (s, 3H), 7.26 (d, J=7.8 Hz, 1H), 7.34-7.56 (m, 12H), 7.66-7.80 (m, 6H), 7.82-7.89 (m, 2H), 8.18-8.27 (m, 2H).

<<Physical Properties of 1PQDMePyA>>

Next, ultraviolet-visible absorption spectra (hereinafter simply referred to as "absorption spectra") and emission spectra of 1PQDMePyA in a toluene solution and a solid thin film of 1PQDMePyA were measured.

Figure 32:
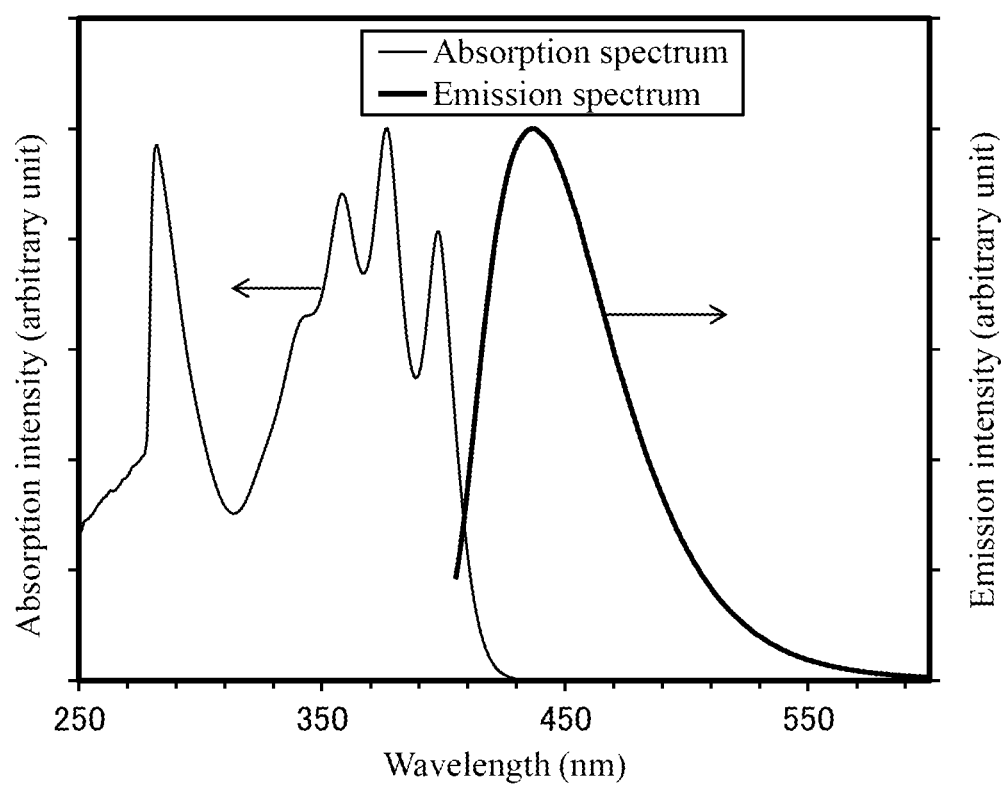
FIG. 32 shows the ultraviolet-visible absorption and emission spectra of an organic compound represented by Structural Formula (175).

The absorption spectrum of 1PQDMePyA in the toluene solution was measured using an ultraviolet-visible spectrophotometer (V-550, produced by JASCO Corporation). The emission spectrum of 1PQDMePyA in the toluene solution was measured using a fluorescence spectrophotometer (FP-8600, produced by JASCO Corporation). Note that the absorption spectrum of 1PQDMePyA in the toluene solution was calculated by subtraction of the measured absorption spectrum of only toluene in a quartz cell. FIG. 32 shows the obtained absorption and emission spectra of 1PQDMePyA in the toluene solution. The horizontal axis represents wavelength and the vertical axes represent absorption intensity and emission intensity.

From the results in FIG. 32, for the toluene solution of 1PQDMePyA, absorption peaks were observed at around 397 nm, 376 nm, and 358 nm, and an emission wavelength peak was observed at around 446 nm (excitation wavelength: 397 nm).

The results reveal that 1PQDMePyA emits blue light. Moreover, 1PQDMePyA, the compound of one embodiment of the present invention, can be used as a host for a light-emitting substance or a substance which emits fluorescence in the visible region.

Example 8

In this example, a light-emitting device 4 which is a light-emitting device of one embodiment of the present invention and a comparative light-emitting device 5 which is a light-emitting device for comparison are fabricated and element structures and properties of the devices are described. The light-emitting device 4 includes 2-phenyl-3-{4-[10-(3-pyridyl)-9-anthryl]phenyl}quinoxaline (abbreviation: PyA1PQ) (Structural Formula (100)) described in Example 1 in an electron-transport layer and the comparative light-emitting device 5 includes 2-phenyl-3-[4'-(3-pyridyl)biphenyl-4-yl]quinoxaline (abbreviation: PPy1PQ) in an electron-transport layer. Note that both of PyA1PQ used for the light-emitting device 4 and PPy1PQ used for the comparative light-emitting device 5 are quinoxaline derivatives; PyA1PQ has a structure in which a heteroaromatic ring is bonded to an anthracene skeleton bonded to a quinoxaline skeleton, and PPy1PQ has a structure in which a heteroaromatic ring is bonded to a phenylene skeleton bonded to a quinoxaline skeleton. Table 3 shows specific structures of the light-emitting devices used in this example. The chemical formulae of materials used in this example are shown below.

TABLE 3

| | first electrode | hole-injection layer | hole-transport layer | light-emitting layer | electron-transport layer | | electron-injection layer | second electrode |
|---|---|---|---|---|---|---|---|---|
| | 901 | 911 | 912 | 913 | 914 | | 915 | 903 |
| light-emitting device 4 | ITSO (70 nm) | BBABnf☐ALD-MP001Q (1:0.1, 10 nm) | BBABnf (20 nm) | PCzN2 (10 nm) | * | PyA1PQ:Liq (1:1, 25 nm) | Liq (1 nm) | Al (200 nm) |
| comparative light-emitting device 5 | | | | | | PPy1PQ:Liq (1:1, 25 nm) | | |

* αN-βNPAnth☐3, 10PCA2Nbf(IV)-02 (1:0.15, 25 nm)

[Chemical Formulae 45]

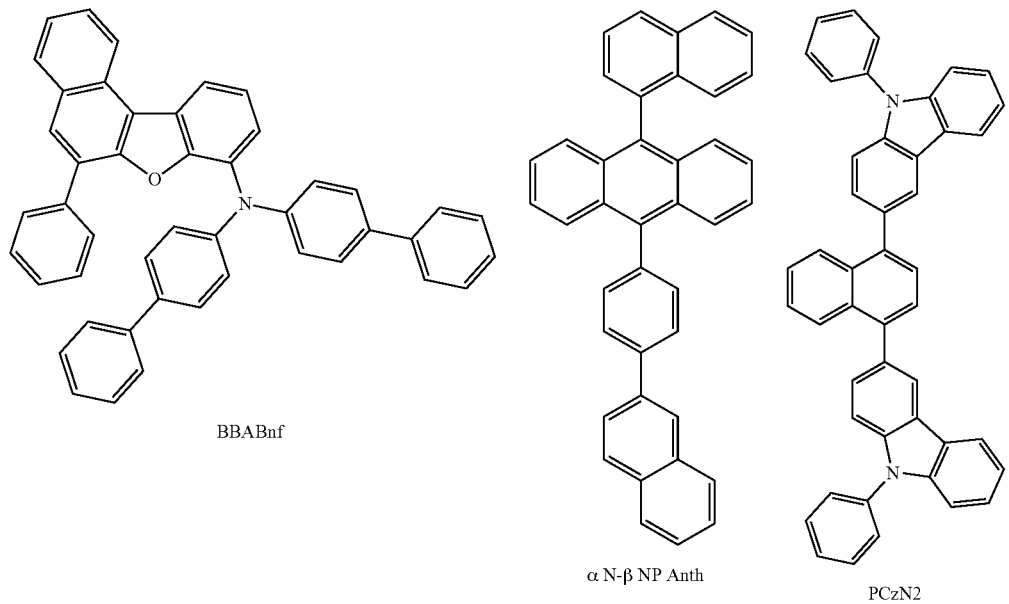

BBABnf

αN-β NP Anth

PCzN2

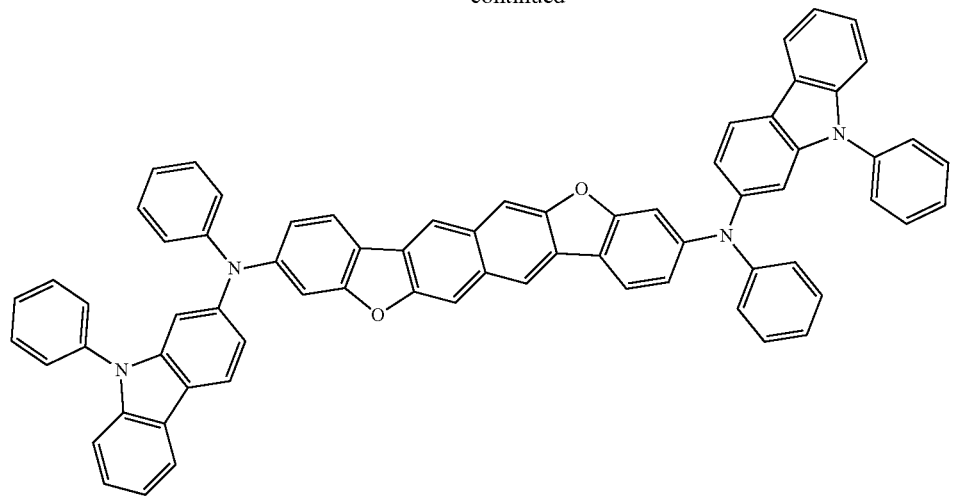

3,10PCA2Nbf(IV)-02

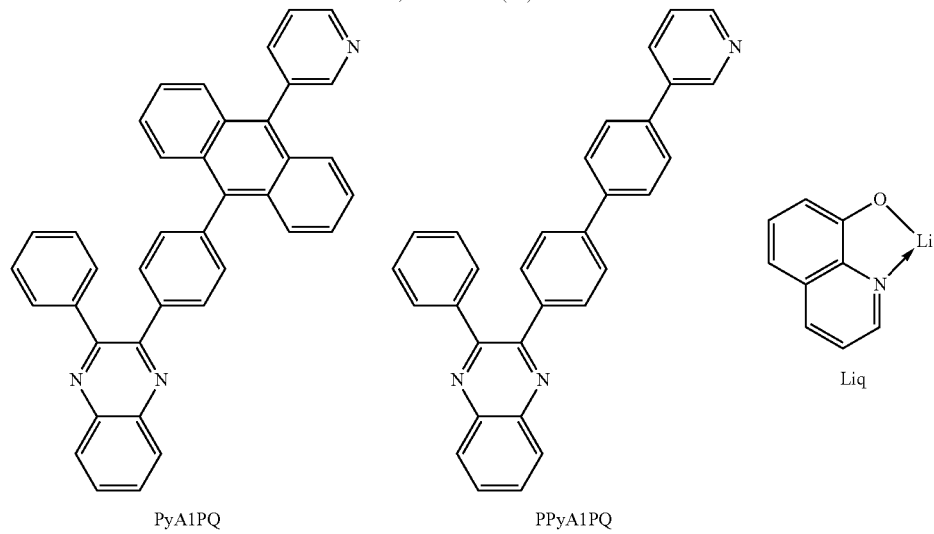

PyA1PQ      PPyA1PQ      Liq

<<Fabrication of Light-Emitting Devices>>

In each of the light-emitting devices described in this example, as in the light-emitting device described in Example 2 with reference to FIG. 11, the hole-injection layer 911, the hole-transport layer 912, the light-emitting layer 913, the electron-transport layer 914, and the electron-injection layer 915 are stacked in this order over the first electrode 901 formed over the substrate 900, and the second electrode 903 is stacked over the electron-injection layer 915.

The hole-injection layer 911 was formed by co-evaporation of N,N-bis(4-biphenyl)-6-phenylbenzo[b]naphtho[1,2-d]furan-8-amine (abbreviation: BBABnf) represented and ALD-MP001Q (produced by Analysis Atelier Corporation, material serial No. 1S20180314) to a thickness of 10 nm in a weight ratio of BBABnf to ALD-MP001Q was 1:0.01. The hole-transport layer 912 was formed by evaporating BBABnf to a thickness of 20 nm and then evaporating 3,3'-(naphthalene-1,4-diyl)bis(9-phenyl-9H-carbazole) (abbreviation: PCzN2) to a thickness of 10 nm.

The light-emitting layer 913 was formed by co-evaporation of 9-(1-naphthyl)-10-[4-(2-naphthyl)phenyl]anthracene (abbreviation: αN-(3NPAnth) and 3,10-bis[N-(9-phenyl-9H-carbazol-2-yl)-N-phenylamino]naphtho[2,3-b;6,7-b'] bisbenzofuran (abbreviation: 3,10PCA2Nbf(IV)-02) to a thickness of 25 nm in a weight ratio of αN-βNPAnth to 3,10PCA2Nbf(IV)-02 was 1:0.015.

The electron-transport layer 914 of the light-emitting device 4 was formed by co-evaporation of PyA1PQ and 8-hydroxyquinolinatolithium (abbreviation: Liq) to a thickness of 25 nm in a weight ratio of PyA1PQ to Liq was 1:1. The electron-transport layer 914 of the comparative light-emitting device 5 was formed by co-evaporation of PPy1PQ and 8-hydroxyquinolinatolithium (abbreviation: Liq) to a thickness of 25 nm in a weight ratio of PPy1PQ to Liq was 1:1.

<<Operation Characteristics of Light-Emitting Devices>>

Figure 33:
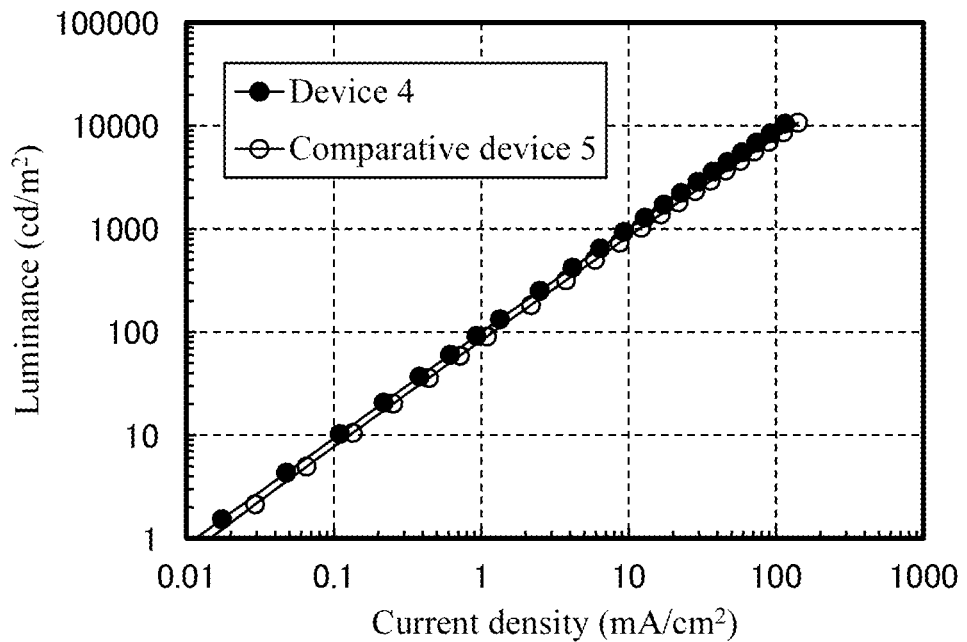
FIG. 33 shows the current density-luminance characteristics of a light-emitting device 4 and a comparative light-emitting device 5.
Figure 34:
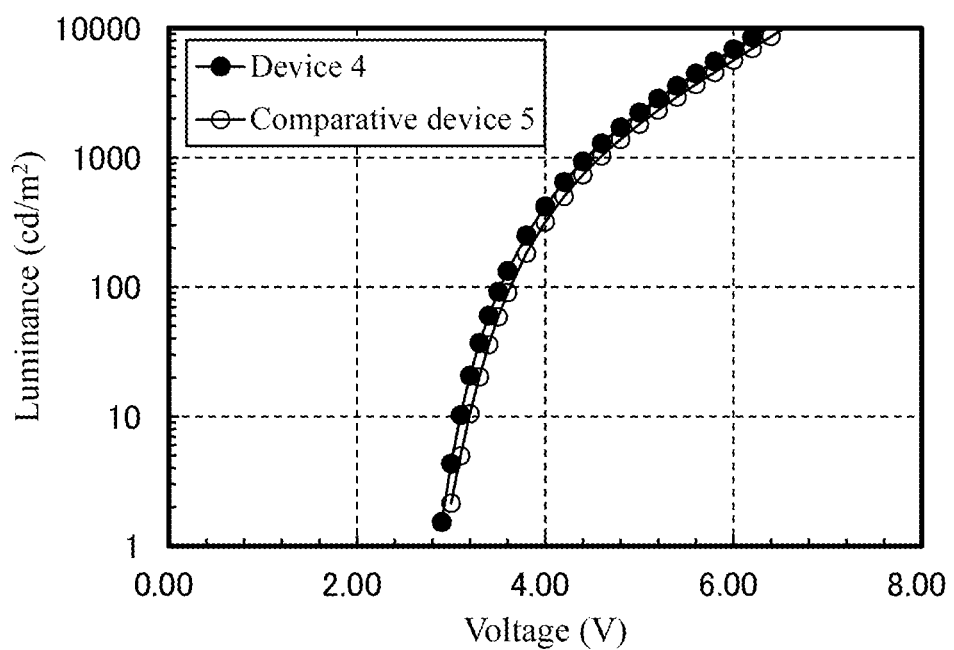
FIG. 34 shows the voltage-luminance characteristics of a light-emitting device 4 and a comparative light-emitting device 5.
Figure 35:
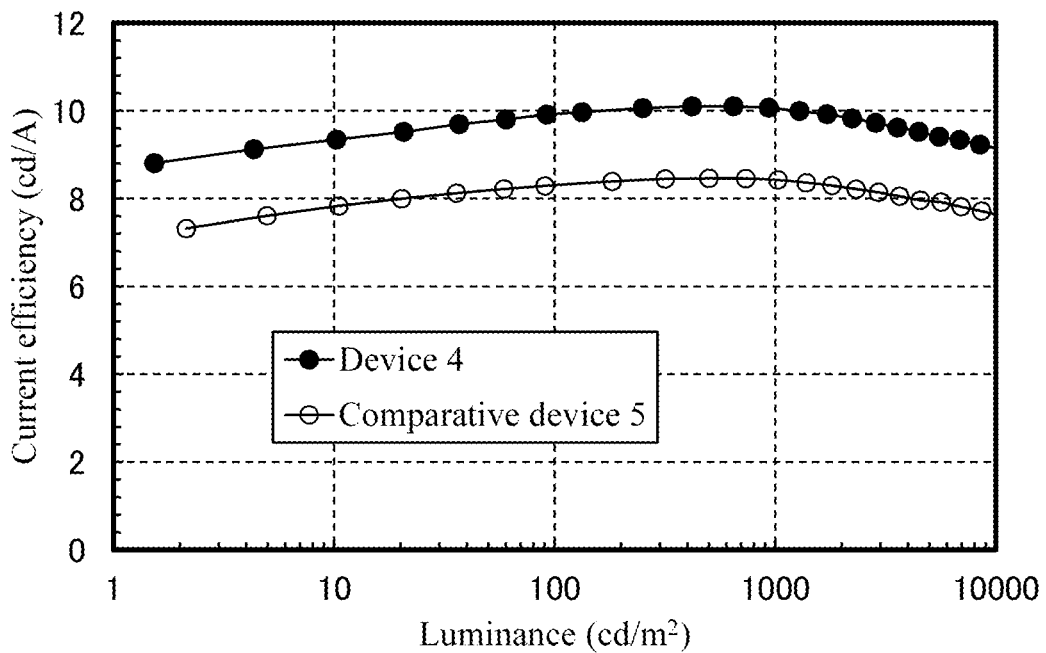
FIG. 35 shows the luminance-current efficiency characteristics of a light-emitting device 4 and a comparative light-emitting device 5.
Figure 36:
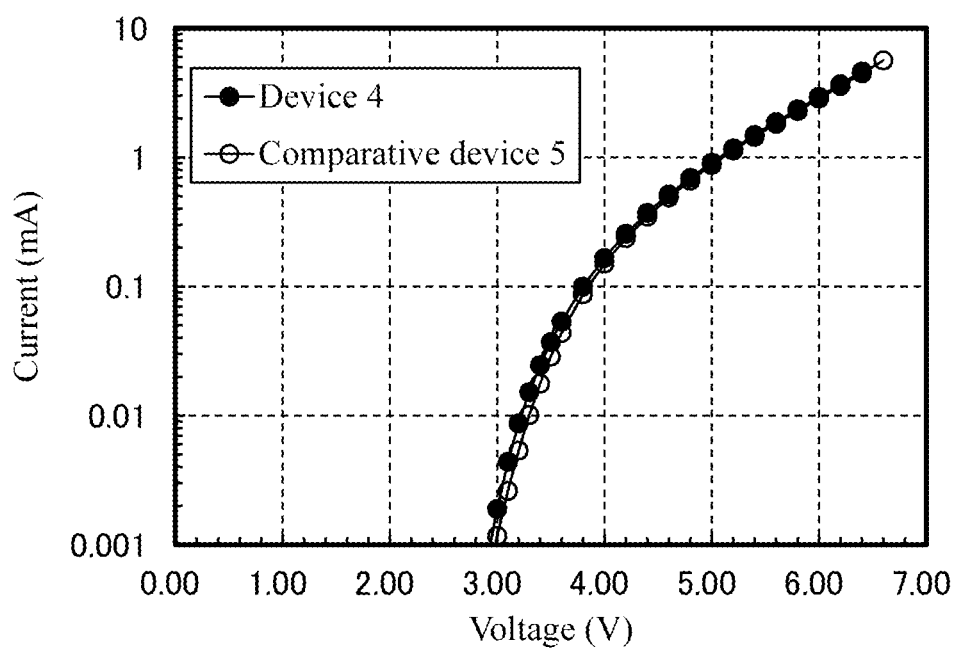
FIG. 36 shows the voltage-current characteristics of a light-emitting device 4 and a comparative light-emitting device 5.

Operation characteristics of the fabricated light-emitting devices were measured. Note that the measurement was performed at room temperature (in an atmosphere kept at 25° C.). As the results of the operation characteristics of the light-emitting devices, the current density-luminance characteristics are shown in FIG. 33, the voltage-luminance characteristics are shown in FIG. 34, the luminance-current efficiency characteristics are shown in FIG. 35, and the voltage-current characteristics are shown in FIG. 36.

Table 4 shows the initial values of main characteristics of the light-emitting devices at around 1000 cd/m$^2$.

TABLE 4

| | voltage (V) | current (mA) | current density (mA/cm$^2$) | chromaticity (x, y) | luminance (cd/m$^2$) | current efficiency (cd/A) | power efficiency (lm/W) | external quantum efficiency (%) |
|---|---|---|---|---|---|---|---|---|
| light-emitting device 4 | 4.4 | 0.37 | 9.3 | (0.14, 0.11) | 930 | 10 | 7.2 | 10 |
| comparative light-emitting device 5 | 4.6 | 0.49 | 12 | (0.14, 0.10) | 1000 | 8.4 | 5.8 | 9.4 |

Figure 37:
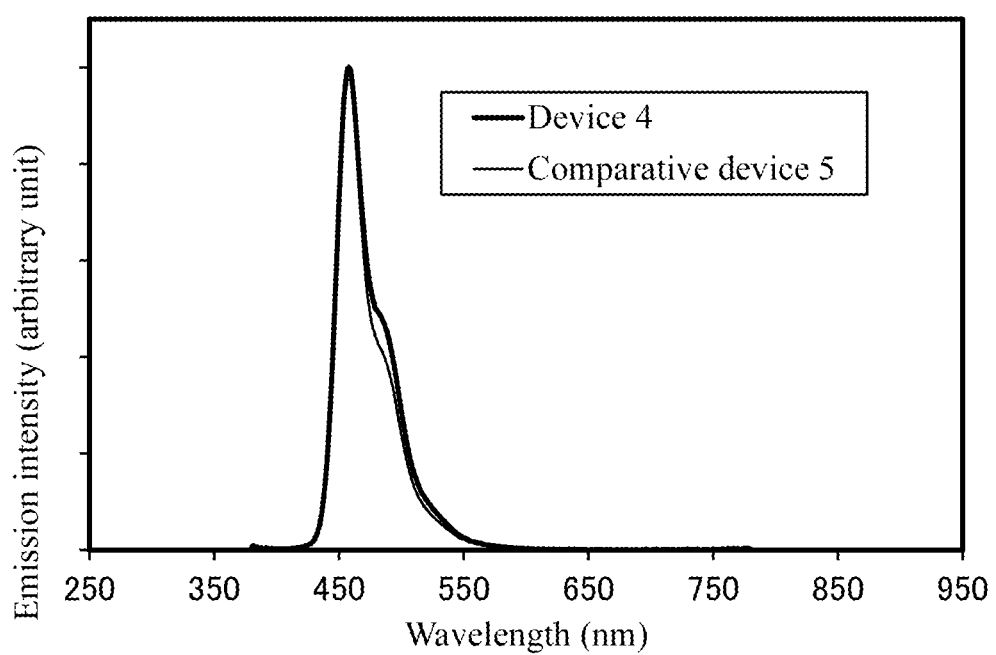
FIG. 37 shows the emission spectra of a light-emitting device 4 and a comparative light-emitting device 5.

The emission spectra of the light-emitting devices were measured at a luminance of approximately 1000 cd/m$^2$. FIG. 37 shows the emission spectra when a voltage of 4.4 V was applied to the light-emitting device 4 and a voltage of 4.6 V was applied to the comparative light-emitting device 5. As shown in FIG. 37, the emission spectrum of each light-emitting device has a peak at around 458 nm, which is presumably derived from light emission of 3,10PCA2Nbf (IV)-02 contained in the light-emitting layer 913.

The results shown in FIG. 33 to FIG. 36 and Table 4 show that the light-emitting device 4 of one embodiment of the present invention using PyA1PQ has current-voltage characteristics, power efficiency, and emission efficiency superior to those of the comparative light-emitting device 5. This is because PyA1PQ used for the light-emitting device 4 has not only the effect of facilitating electron extraction from the electron-transport layer 915 to the electron-transport layer 914 owing to the heteroaromatic ring bonded to the quinoxaline skeleton through the anthracene skeleton, but also a high transport property of injected electrons owing to having an anthracene skeleton.

Figure 38:
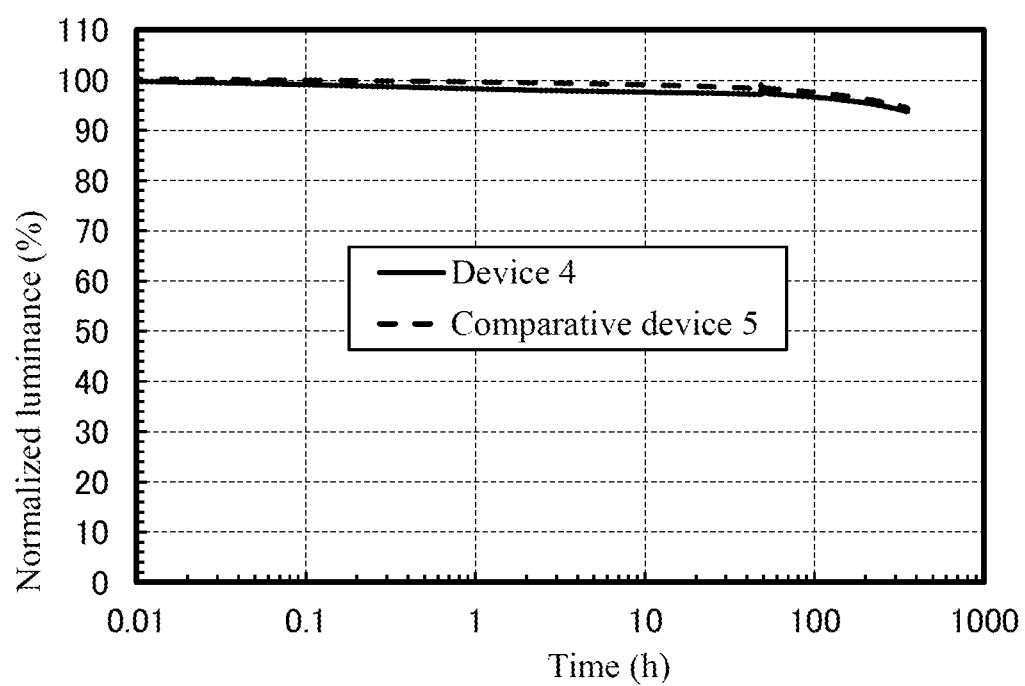
FIG. 38 shows the reliability of each of a light-emitting device 4 and a comparative light-emitting device 5.

FIG. 38 is a graph showing a change in luminance over driving time at a current density of 50 mA/cm$^2$. As shown in FIG. 38, the luminances of the light-emitting device 4 of one embodiment of the present invention and the comparative light-emitting device 5 deteriorate to the same degree over driving time. The luminance of the light-emitting device 4 of one embodiment of the present invention was higher than that of the comparative light-emitting device 5 when the luminances were measured at the same current density because the light-emitting device 4 has higher current efficiency than the comparative light-emitting device 5. However, the luminances of those devices deteriorated to the same degree over driving time.

Example 9

This example describes element structures and characteristics of light-emitting devices of embodiments of the present invention: a light-emitting device 6 in which 2-phenyl-3-{4-[10-(pyrimidin-5-yl)-9-anthryl]phenyl}quinoxaline (abbreviation: 1PQPmA) (Structural Formula (101)) described in Example 3 is used in an electron-transport layer, a light-emitting device 7 in which 2-phenyl-3-[10-(pyrazin-2-yl)-9-anthryl]quinoxaline (abbreviation: 1PQPrA) (Structural Formula (102)) described in Example 4 is used in an electron-transport layer, a light-emitting device 8 in which 2-phenyl-3-(4-{10-[4-(3-pyridyl)phenyl]-9-anthryl}phenyl) quinoxaline (abbreviation: 1PQPyPA) (Structural Formula (135)) described in Example 5 is used in an electron-transport layer, and a light-emitting device 9 in which 2-phenyl-3-{4-[10-(5-phenyl-3-pyridyl)-9-anthryl] phenyl}quinoxaline (abbreviation: 1PQmPPyA) (Structural Formula (147)) described in Example 6 is used in an electron-transport layer. Table 5 shows specific structures of the light-emitting devices used in this example. The chemical formulae of materials used in this example are shown below.

TABLE 5

| | first electrode | hole-injection layer | hole-transport layer | light-emitting layer | electron-transport layer | | electron-injection layer | second electrode |
|---|---|---|---|---|---|---|---|---|
| | 901 | 911 | 912 | 913 | 914 | | 915 | 903 |
| light-emitting device 6 | ITSO (70 nm) | BBABnf□ ALD-MP001Q (1:0.1, 10 nm) | BBABnf (20 nm) | PCzN2 (10 nm) | * | 1PQPmA□Liq (1:2, 25 nm) | Liq (1 nm) | Al (200 nm) |
| light-emitting device 7 | | | | | | 1PQPrA□Liq (1:2, 25 nm) | | |
| light-emitting device 8 | | | | | | 1PQPyPA□Liq (1:2, 25 nm) | | |
| light-emitting device 9 | | | | | | 1PQmPPyA:Liq (1:1, 25 nm) | | |

* αN-βNPAnth□3, 10PCA2Nbf(IV)-02 (1:0.15, 25 nm)

[Chemical Formulae 46]
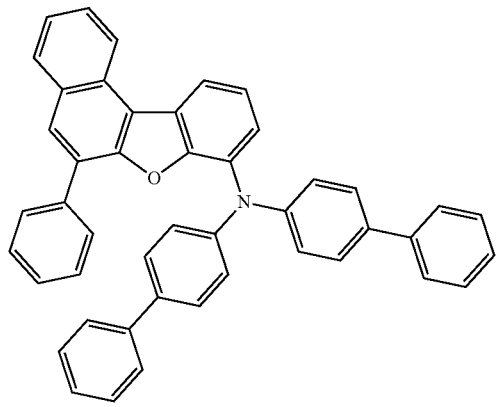
BBABnf
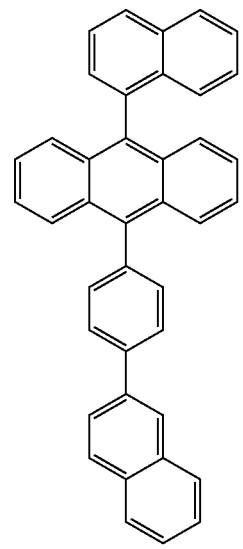
α N-β NP Anth
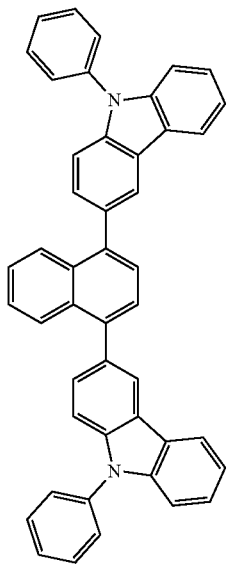
PCzN2
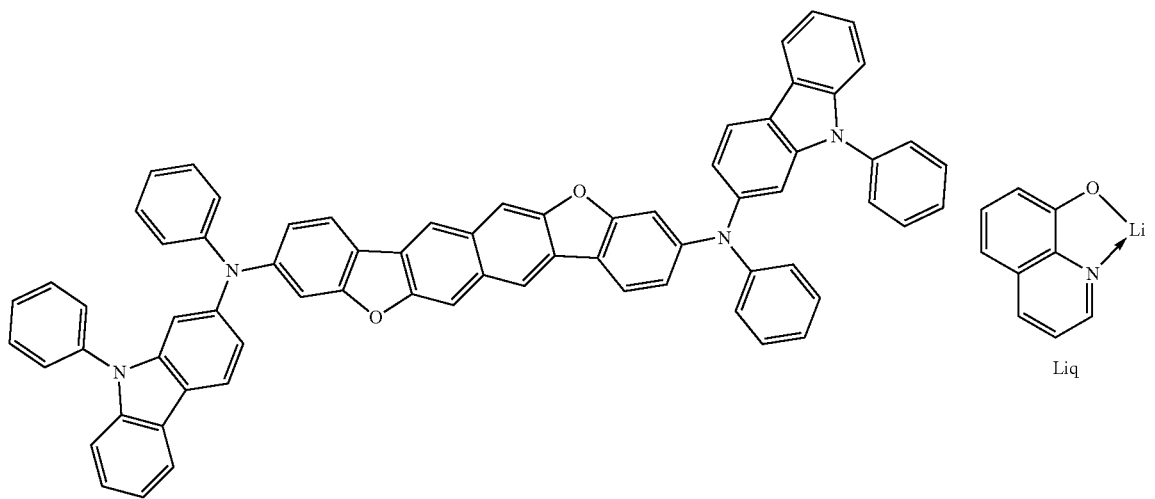
3,10PCA2Nbf(IV)-02
Liq -continued

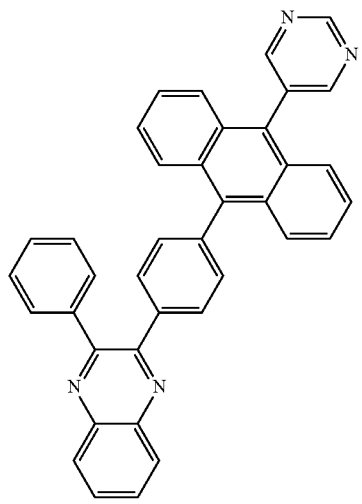

(101)

1PQPmA

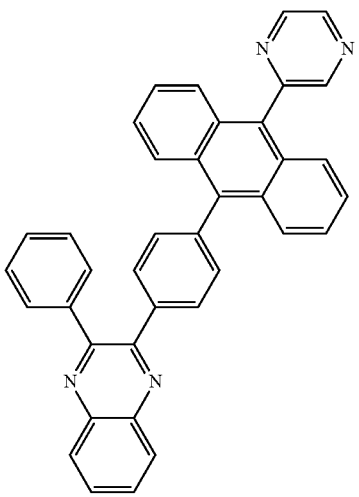

(102)

1PQPrA

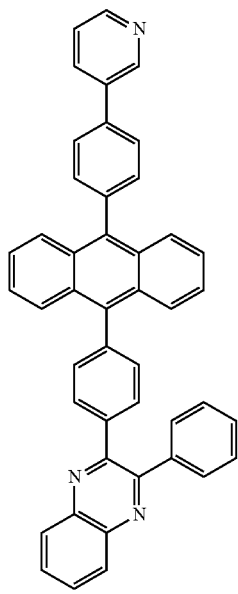

(135)

1PQPyPA

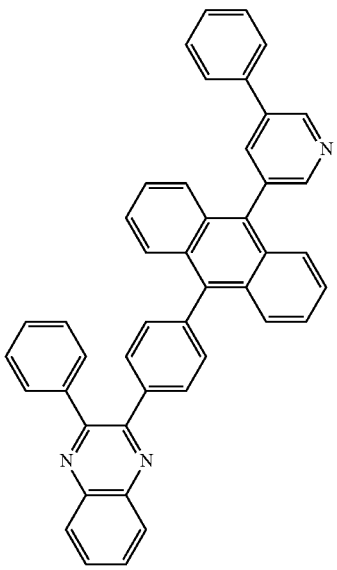

(147)

1PQmPPyA

<<Fabrication of Light-Emitting Devices>>

In each of the light-emitting devices described in this example, as in the light-emitting device described in Example 2 with reference to FIG. 11, the hole-injection layer 911, the hole-transport layer 912, the light-emitting layer 913, the electron-transport layer 914, and the electron-injection layer 915 are stacked in this order over the first electrode 901 formed over the substrate 900, and the second electrode 903 is stacked over the electron-injection layer 915.

The hole-injection layer 911 was formed by co-evaporation of N,N-bis(4-biphenyl)-6-phenylbenzo[b]naphtho[1,2-d]furan-8-amine (abbreviation: BBABnf) represented and ALD-MP001Q (produced by Analysis Atelier Corporation, material serial No. 1S20180314) to a thickness of 10 nm in a weight ratio of BBABnf to ALD-MP001Q was 1:0.01. The hole-transport layer 912 was formed by evaporating BBABnf to a thickness of 20 nm and then evapolating 3,3'-(naphthalene-1,4-diyl)bis(9-phenyl-9H-carbazol e) (abbreviation: PCzN2) to a thickness of 10 nm.

The light-emitting layer 913 was formed by co-evaporation of 9-(1-naphthyl)-10-[4-(2-naphthyl)phenyl]anthracene (abbreviation: αN-βNPAnth) and 3,10-bis[N-(9-phenyl-9H-carbazol-2-yl)-N-phenylamino]naphtho[2,3-b;6,7-b']bis-benzofuran (abbreviation: 3,10PCA2Nbf(IV)-02) to a thickness of 25 nm in a weight ratio of αN-βNPAnth to 3,10PCA2Nbf(IV)-02 was 1:0.015.

The electron-transport layer 914 of the light-emitting device 6 was formed by co-evaporation of 1PQPmA and Liq to a thickness of 25 nm in a weight ratio of 1PQPmA to Liq was 1:2. The electron-transport layer 914 of the light-emitting device 7 was formed by co-evaporation of 1PQPrA and 8-hydroxyquinolinatolithium (abbreviation: Liq) to a thickness of 25 nm in a weight ratio of 1PQPrA to Liq was 1:2. The electron-transport layer 914 of the light-emitting device 8 was formed by co-evaporation of 1PQPyPA and 8-hydroxyquinolinatolithium (abbreviation: Liq) to a thickness of 25 nm in a weight ratio of 1PQPyA to Liq was 1:2. The electron-transport layer 914 of the light-emitting device 9 was formed by co-evaporation of 1PQmPPyA and 8-hydroxyquinolinatolithium (abbreviation: Liq) to a thickness of 25 nm in a weight ratio of 1PQmPPyA to Liq was 1:1.

<<Operation Characteristics of Light-Emitting Devices>>

Operation characteristics of the fabricated light-emitting devices were measured. Note that the measurement was performed at room temperature (in an atmosphere kept at 25° C.). Table 6 shows the initial values of main characteristics of the light-emitting devices at around 1000 cd/m².

TABLE 6

| | voltage (V) | current (mA) | current density (mA/cm²) | chromaticity (x, y) | luminance (cd/m²) | current efficiency (cd/A) | power efficiency (lm/W) | external quantum efficiency (%) |
|---|---|---|---|---|---|---|---|---|
| light-emitting device 6 | 4.8 | 0.48 | 12 | (0.13, 0.12) | 1100 | 9.6 | 6.3 | 9.7 |
| light-emitting device 7 | 4.4 | 0.37 | 9.3 | (0.14, 0.11) | 910 | 9.8 | 7.0 | 10 |
| light-emitting device 8 | 4.7 | 0.36 | 9.0 | (0.14, 0.10) | 870 | 9.7 | 6.5 | 11 |
| light-emitting device 9 | 5.0 | 0.43 | 11 | (0.14, 0.11) | 880 | 8.1 | 5.1 | 8.5 |

The results shown in Table 6 show that the light-emitting devices 6 to 9 of one embodiment of the present invention has favorable operation characteristics such as current-voltage characteristics, power efficiency, and emission efficiency.

Figure 39:
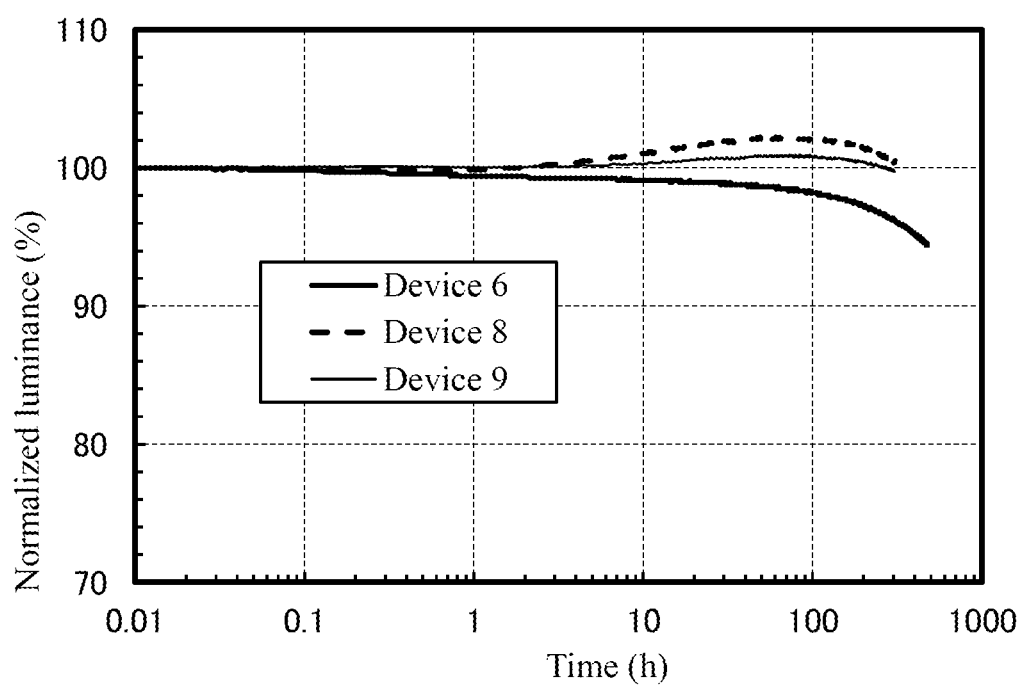
FIG. 39 shows the reliability of each of a light-emitting device 6, a light-emitting device 7, a light-emitting device 8, and a light-emitting device 9.

FIG. 39 is a graph showing a change in luminance of the light-emitting devices over driving time at a current density of 50 mA/cm². As shown in FIG. 39, the light-emitting devices 6 to 9 of one embodiment of the present invention were found to be long-lifetime light-emitting devices with a small reduction in luminance over driving time.

REFERENCE NUMERALS

101: first electrode, 102: second electrode, 103: EL layer, 111: hole-injection layer, 112: hole-transport layer, 113: light-emitting layer, 114: electron-transport layer, 115: electron-injection layer, 103a, 103b: EL layer, 104: charge-generation layer, 111a, 111b: hole-injection layer, 112a, 112b: hole-transport layer, 113a, 113b: light-emitting layer, 114a, 114b: electron-transport layer, 115a, 115b: electron-injection layer, 200R, 200G, 200B: optical path length, 201: first substrate, 202: transistor (FET), 203R, 203G, 203B, 203W: light-emitting device, 204: EL layer, 205: second substrate, 206R, 206G, 206B: color filter, 206R', 206G', 206B': color filter, 207: first electrode, 208: second electrode, 209: black layer (black matrix), 210R, 210G: conductive layer, 301: first substrate, 302: pixel portion, 303: driver circuit portion (source line driver circuit), 304a, 304b: driver circuit portion (gate line driver circuit), 305: sealant, 306: second substrate, 307: lead wiring, 308: FPC, 309: FET, 310: FET, 311: FET, 312: FET, 313: first electrode, 314: insulator, 315: EL layer, 316: second electrode, 317: light-emitting device, 318: space, 901: first electrode, 902: EL layer, 903: second electrode, 911: hole-injection layer, 912: hole-transport layer, 913: light-emitting layer, 914: electron-transport layer, 915: electron-injection layer, 4000: lighting device, 4001: substrate, 4002: light-emitting device, 4003: substrate, 4004: first electrode, 4005: EL layer, 4006: second electrode, 4007: electrode, 4008: electrode, 4009: auxiliary wiring, 4010: insulating layer, 4011: sealing substrate, 4012: sealant, 4013: desiccant, 4200: lighting device, 4201: substrate, 4202: light-emitting device, 4204: first electrode, 4205: EL layer, 4206: second electrode, 4207: electrode, 4208: electrode, 4209: auxiliary wiring, 4210: insulating layer, 4211: sealing substrate, 4212: sealant, 4213: barrier film, 4214: planarization film, 5101: light, 5102: wheel, 5103: door, 5104: display portion, 5105: steering wheel, 5106: gear lever, 5107: seat, 5108: inner rearview mirror, 5109: windshield, 7000: housing, 7001: display portion, 7002: second display portion, 7003: speaker, 7004: LED lamp, 7005: operation key, 7006: connection terminal, 7007: sensor, 7008: microphone, 7009: switch, 7010: infrared port, 7011: recording medium reading portion, 7014: antenna, 7015: shutter button, 7016: image receiving portion, 7018: stand, 7022, 7023: operation button, 7024: connection terminal, 7025: band, 7026: microphone, 7029: sensor, 7030: speaker, 7052, 7053, 7054: information, 9310: portable information terminal, 9311: display portion, 9312: display region, 9313: hinge, 9315: housing.

This application is based on Japanese Patent Application Serial No. 2019-055331 filed with Japan Patent Office on Mar. 22, 2019, the entire contents of which are hereby incorporated by reference.

The invention claimed is:

1. An organic compound represented by Formula (G1),

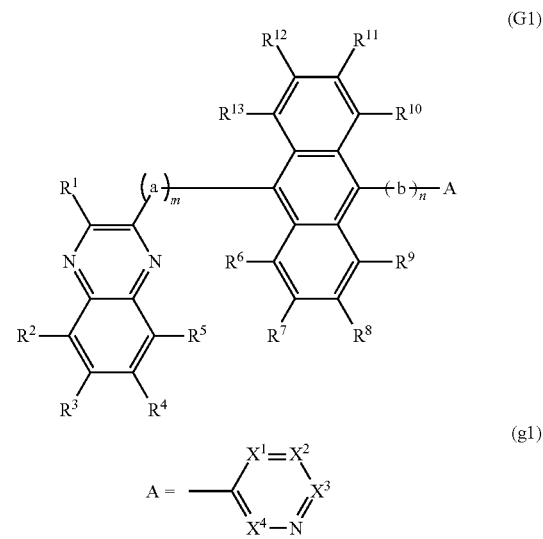

wherein each of a and b independently represents a substituted or unsubstituted arylene group having 6 to 13 carbon atoms in a ring, wherein each of m and n is independently 0, 1 or 2, wherein each of $R^1$ to $R^{13}$ independently represents any one of hydrogen, an alkyl group having 1 to 6 carbon atoms, a substituted or unsubstituted cyclic alkyl group having 3 to 7 carbon atoms in a ring, and a substituted or unsubstituted aryl group having 6 to 13 carbon atoms in a ring, wherein A is represented by Formula (g1), wherein each of $X^1$ to $X^4$ independently represents N or $CR^{14}$, and wherein $R^{14}$ represents any one of hydrogen, an alkyl group having 1 to 6 carbon atoms, a substituted or unsubstituted cyclic alkyl group having 3 to 7 carbon atoms in a ring, and a substituted or unsubstituted aryl group having 6 to 13 carbon atoms in a ring.

2. The organic compound according to claim 1, wherein the organic compound is represented by Formula (G2):

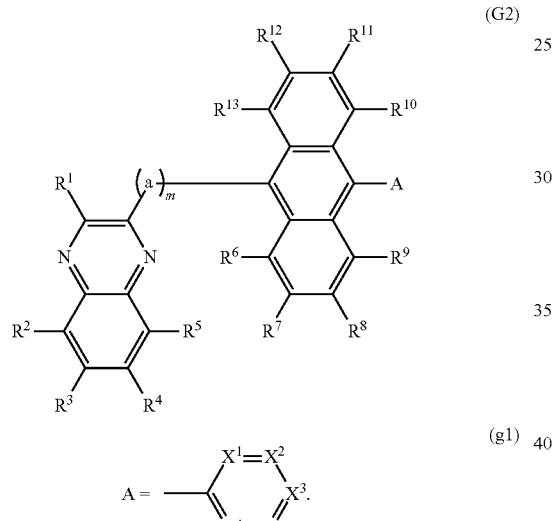

(G2)

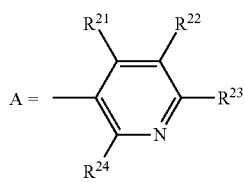

(g1)

3. The organic compound according to claim 1, wherein the organic compound is represented by Formula (G3):

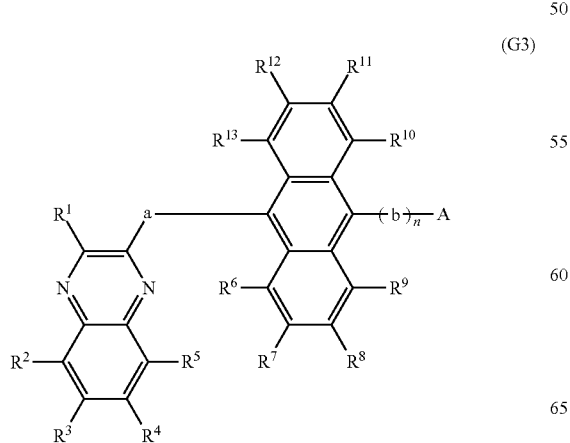

(G3)

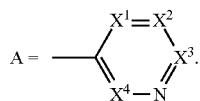

(g1)

4. The organic compound according to claim 1, wherein m is 2, and wherein the two arylene groups a are the same.

5. The organic compound according to claim 1, wherein n is 2, and wherein the two arylene groups b are the same.

6. The organic compound according to claim 1, wherein a represents a substituted or unsubstituted phenylene group.

7. The organic compound according to claim 1, wherein Formula (g1) is represented by any one of Formulae (g1-1) to (g1-3), and

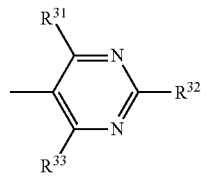

(g1-1)

(g1-2)

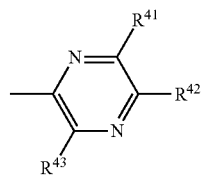

(g1-3)

wherein each of $R^{21}$ to $R^{24}$, $R^{31}$ to $R^{33}$, and $R^{41}$ to $R^{43}$ independently represents any one of hydrogen, an alkyl group having 1 to 6 carbon atoms, a substituted or unsubstituted cyclic alkyl group having 3 to 7 carbon atoms in a ring, and a substituted or unsubstituted aryl group having 6 to 13 carbon atoms in a ring.

8. The organic compound according to claim 1, wherein Formula (g1) is represented by any one of Formulae (g1-4) to (g1-6):

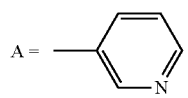

(g1-4)

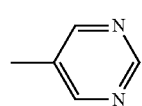

(g1-5)

(g1-6)
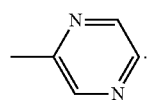
9. The organic compound according to claim 1, wherein the organic compound is represented by any one of Formulae (100), (101), (102), (135), (147) and (175):
(100)
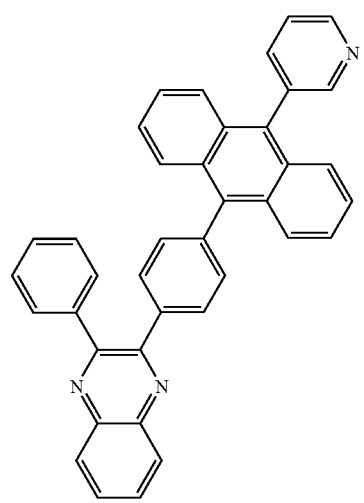
(101)
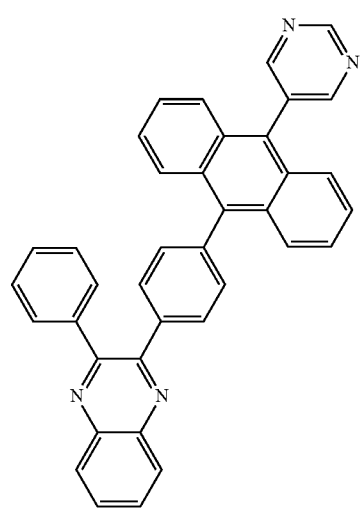
(102)
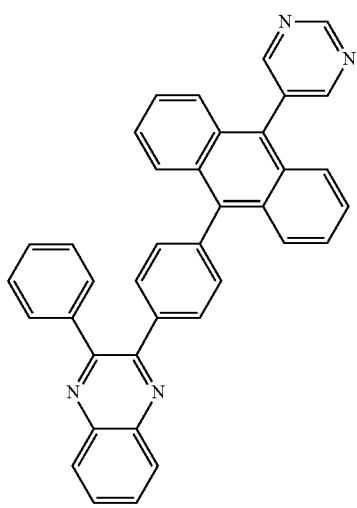
(135)
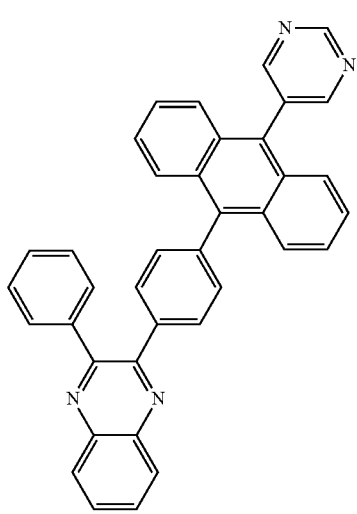
(147)
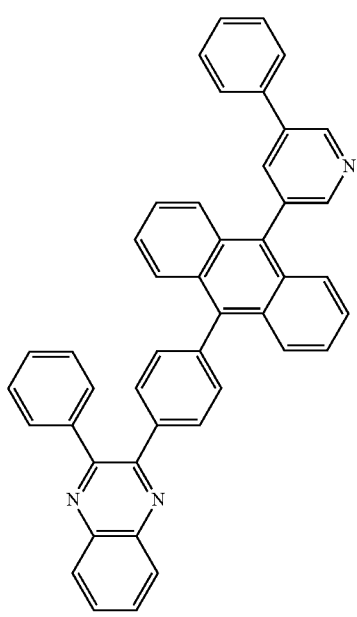

-continued

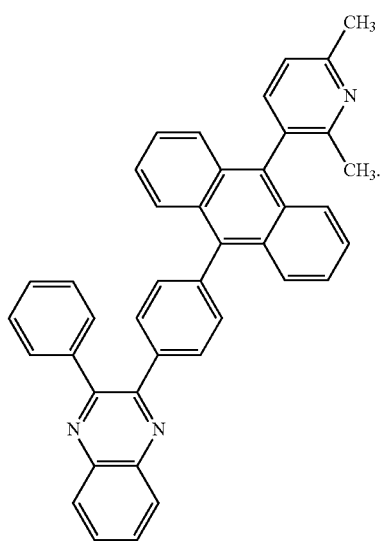

(175)

10. A light-emitting device comprising the organic compound according to claim 1.

11. A light-emitting device comprising:
a first electrode;
an electroluminescence layer over the first electrode, the electroluminescence layer comprising the organic compound according to claim 1; and
a second electrode over the electroluminescence layer.

12. A light-emitting device comprising:
a first electrode;
a light-emitting layer over the first electrode;
an electron-transport layer over the light-emitting layer, the electron-transport layer comprising the organic compound according to claim 1; and
a second electrode over the electron-transport layer.

13. A light-emitting device comprising:
a first electrode;
a light-emitting layer over the first electrode, the light-emitting layer comprising a fluorescent material;
an electron-transport layer over the light-emitting layer, the electron-transport layer comprising the organic compound according to claim 1; and
a second electrode over the electron-transport layer.

14. A light-emitting apparatus comprising:
the light-emitting device according to claim 11; and
at least one of a transistor and a substrate.

15. An electronic device comprising:
the light-emitting apparatus according to claim 14; and
at least one of a microphone, a camera, an operation button, an external connection portion and a speaker.

16. A lighting device comprising:
the light-emitting device according to claim 11; and
at least one of a housing, a cover and a stand.

17. An organic compound represented by Formula (G3),

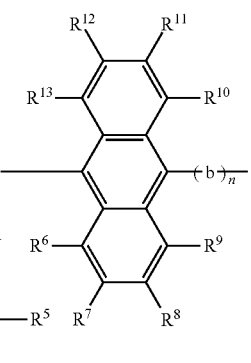
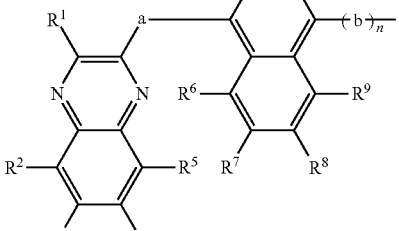

(G3)

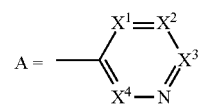

(g1)

wherein a and b each represent a substituted or unsubstituted arylene group having 6 to 13 carbon atoms in a ring,
wherein n represents 0,
wherein $R^1$ to $R^{13}$ each independently represent hydrogen, an alkyl group having 1 to 6 carbon atoms, a substituted or unsubstituted cyclic alkyl group having 3 to 7 carbon atoms in a ring, or a substituted or unsubstituted aryl group having 6 to 13 carbon atoms in a ring,
wherein A is represented by Formula (g1),
wherein $X^1$ to $X^4$ each independently represent N or $CR^{14}$, and
wherein $R^{14}$ represents any one of hydrogen, an alkyl group having 1 to 6 carbon atoms, a substituted or unsubstituted cyclic alkyl group having 3 to 7 carbon atoms in a ring, and a substituted or unsubstituted aryl group having 6 to 13 carbon atoms in a ring.

18. The organic compound according to claim 17, wherein a represents a substituted or unsubstituted phenylene group.

19. The organic compound according to claim 17,
wherein Formula (g1) is represented by any one of Formulae (g1-1) to (g1-3), and

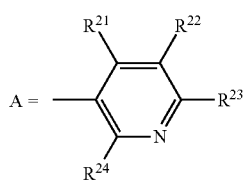

(g1-1)

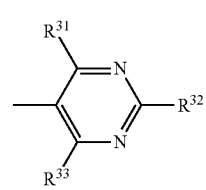

(g1-2)

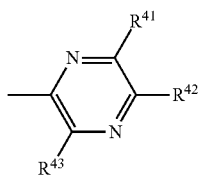
(g1-3)

wherein each of $R^{21}$ to $R^{24}$, $R^{31}$ to $R^{33}$, and $R^{41}$ to $R^{43}$ independently represents any one of hydrogen, an alkyl group having 1 to 6 carbon atoms, a substituted or unsubstituted cyclic alkyl group having 3 to 7 carbon atoms in a ring, and a substituted or unsubstituted aryl group having 6 to 13 carbon atoms in a ring.

20. The organic compound according to claim 17, wherein Formula (g1) is represented by any one of Formulae (g1-4) to (g1-6):

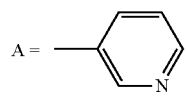
(g1-4)

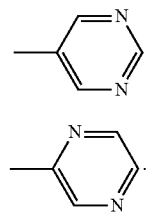
(g1-5)

(g1-6)

21. A light-emitting device comprising the organic compound according to claim 17.

22. A light-emitting device comprising:
a first electrode;
a light-emitting layer over the first electrode;
an electron-transport layer over the light-emitting layer, the electron-transport layer comprising the organic compound according to claim 17; and
a second electrode over the electron-transport layer.

23. A light-emitting apparatus comprising:
the light-emitting device according to claim 21; and
at least one of a transistor and a substrate.

24. An electronic device comprising:
the light-emitting apparatus according to claim 23; and
at least one of a microphone, a camera, an operation button, an external connection portion and a speaker.

* * * * *